(12) United States Patent
Tanaka et al.

(10) Patent No.: US 11,649,262 B2
(45) Date of Patent: May 16, 2023

(54) METHOD FOR PROMOTING EFFICIENCY OF PURIFICATION OF FC REGION-CONTAINING POLYPEPTIDE

(71) Applicant: Chugai Seiyaku Kabushiki Kaisha, Tokyo (JP)

(72) Inventors: Nobuyuki Tanaka, Tokyo (JP); Rumiko Momose, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 559 days.

(21) Appl. No.: 16/061,454

(22) PCT Filed: Dec. 27, 2016

(86) PCT No.: PCT/JP2016/088820
§ 371 (c)(1),
(2) Date: Jun. 12, 2018

(87) PCT Pub. No.: WO2017/115773
PCT Pub. Date: Jul. 6, 2017

(65) Prior Publication Data
US 2019/0330268 A1 Oct. 31, 2019

(30) Foreign Application Priority Data
Dec. 28, 2015 (JP) .............................. JP2015-255726

(51) Int. Cl.
| C07K 1/22 | (2006.01) |
| C07K 16/06 | (2006.01) |
| C07K 16/36 | (2006.01) |
| C07K 16/40 | (2006.01) |

(52) U.S. Cl.
CPC ................ *C07K 1/22* (2013.01); *C07K 16/36* (2013.01); *C07K 16/40* (2013.01); *C07K 2317/31* (2013.01)

(58) Field of Classification Search
CPC combination set(s) only.
See application file for complete search history.

(56) References Cited

U.S. PATENT DOCUMENTS

| 4,208,479 | A | 6/1980 | Zuk et al. |
| 4,444,878 | A | 4/1984 | Paulus |
| 4,474,893 | A | 10/1984 | Reading |
| 5,126,250 | A | 6/1992 | McDonough et al. |
| 5,322,678 | A | 6/1994 | Morgan et al. |
| 5,496,549 | A | 3/1996 | Yamazaki et al. |
| 5,585,097 | A | 12/1996 | Bolt et al. |
| 5,591,828 | A | 1/1997 | Bosslet et al. |
| 5,624,821 | A | 4/1997 | Winter et al. |
| 5,639,641 | A | 6/1997 | Pedersen et al. |
| 5,648,260 | A | 7/1997 | Winter et al. |
| 5,670,373 | A | 9/1997 | Kishimoto |
| 5,744,446 | A | 4/1998 | Lollar et al. |
| 5,795,965 | A | 8/1998 | Tsuchiya et al. |
| 5,837,821 | A | 11/1998 | Wu |
| 5,859,205 | A | 1/1999 | Adair et al. |
| 5,877,291 | A | 3/1999 | Mezes et al. |
| 5,945,311 | A | 8/1999 | Lindhofer et al. |
| 5,990,286 | A | 11/1999 | Khawli et al. |
| 6,005,091 | A | 12/1999 | Blackburn et al. |
| 6,010,902 | A | 1/2000 | Ledbetter et al. |
| 6,025,165 | A | 2/2000 | Whitlow et al. |
| 6,126,980 | A | 10/2000 | Smith et al. |
| 6,129,914 | A | 10/2000 | Weiner |
| 6,132,992 | A | 10/2000 | Ledbetter et al. |
| 6,183,744 | B1 | 2/2001 | Goldenberg |
| 6,323,000 | B2 | 11/2001 | Briggs et al. |
| 6,329,511 | B1 | 12/2001 | Vasquez et al. |
| 6,342,220 | B1 | 1/2002 | Adams et al. |
| 6,368,596 | B1 | 4/2002 | Ghetie et al. |
| 6,485,943 | B2 | 11/2002 | Stevens et al. |
| 6,677,436 | B1 | 1/2004 | Sato et al. |
| 6,683,157 | B2 | 1/2004 | Briggs et al. |
| 6,699,686 | B1 | 3/2004 | Brocard et al. |
| 6,723,319 | B1 | 4/2004 | Ito et al. |
| 6,737,056 | B1 | 5/2004 | Presta |
| 6,884,879 | B1 | 4/2005 | Baca et al. |
| 6,913,747 | B1 | 7/2005 | Co et al. |
| 7,018,632 | B2 | 3/2006 | Lindhofer et al. |
| 7,033,590 | B1 | 4/2006 | Scheiflinger et al. |
| 7,052,873 | B2 | 5/2006 | Tsuchiya |

(Continued)

FOREIGN PATENT DOCUMENTS

| AU | 755822 | 3/1999 |
| AU | 2009290162 | 4/2010 |

(Continued)

OTHER PUBLICATIONS

Alignment of Fc domain sequences of catumaxomab and SEQ ID Nos. 23, 24, 25 and 26 (cited in oppositions filed against European Patent No. 2 647 707 on May 31, 2019 and Jun. 12, 2019), 2 pages.
An et al., "IgG2m4, an engineered antibody isotype with reduced Fc function," mAbs, Nov.-Dec. 2009, 1(6):572-9.
Aschermann et al., "The other side of immunoglobulin G: suppressor of inflammation," Clin Exp Immunol, May 2010, 160(2):161-7. doi: 10.1111/j.1365-2249.2009.04081.x. Epub Dec. 16, 2009.
Brennan et al., "Safety and immunotoxicity assessment of immunomodulatory monoclonal antibodies," mAbs, May-Jun. 2010, 2(3):233-55, Epub May 23, 2010.
Chelius et al., "Structural and functional characterization of the trifunctional antibody catumaxomab," mAbs, May-Jun. 2010, 2(3):309-19, Epub May 16, 2010.

(Continued)

*Primary Examiner* — Daniel E Kolker
*Assistant Examiner* — James L Rogers
(74) *Attorney, Agent, or Firm* — Fish & Richardson P.C.

(57) ABSTRACT

It was discovered that, by preparing an Fc region of an Fc region-containing polypeptide in which the first polypeptide chain of the Fc region binds to a Protein A resin, but the second polypeptide chain of the Fc region does not bind to the resin or shows weak binding to it, the amount of the Fc region-containing polypeptide bound per volume of the resin is increased, and more efficient purification of the above-mentioned Fc region-containing polypeptide is possible.

21 Claims, 1 Drawing Sheet
Specification includes a Sequence Listing.

(56) References Cited

U.S. PATENT DOCUMENTS

| | | | |
|---|---|---|---|
| 7,122,637 B2 | 10/2006 | Presta | |
| 7,217,797 B2 | 5/2007 | Hinton et al. | |
| 7,276,585 B2 | 10/2007 | Lazar et al. | |
| 7,538,196 B2 | 5/2009 | Jung | |
| 7,732,149 B2 | 6/2010 | Kojima et al. | |
| 8,062,635 B2 | 11/2011 | Hattori et al. | |
| 8,217,147 B2 | 7/2012 | Stavenhagen et al. | |
| 8,592,562 B2 | 11/2013 | Kannan et al. | |
| 8,597,911 B2 | 12/2013 | Miyazaki et al. | |
| 8,735,545 B2 | 5/2014 | Lazar et al. | |
| 8,765,124 B2 | 7/2014 | Saito et al. | |
| 9,096,651 B2 | 8/2015 | Igawa et al. | |
| 9,109,010 B2 * | 8/2015 | Hickman | A61P 3/10 |
| 9,228,017 B2 | 1/2016 | Igawa et al. | |
| 9,334,331 B2 | 5/2016 | Igawa et al. | |
| 9,670,269 B2 | 6/2017 | Igawa et al. | |
| 9,688,762 B2 | 6/2017 | Igawa et al. | |
| 9,828,429 B2 | 11/2017 | Igawa et al. | |
| 10,011,858 B2 | 7/2018 | Igawa et al. | |
| 10,022,319 B2 | 7/2018 | Igawa et al. | |
| 10,066,018 B2 | 9/2018 | Igawa et al. | |
| 10,150,808 B2 | 12/2018 | Kuramochi et al. | |
| 10,253,091 B2 | 4/2019 | Igawa et al. | |
| 10,435,458 B2 | 10/2019 | Kuramochi et al. | |
| 10,450,381 B2 | 10/2019 | Igawa et al. | |
| 10,759,870 B2 | 9/2020 | Teranishi et al. | |
| 10,934,344 B2 | 3/2021 | Igawa et al. | |
| 11,046,784 B2 | 6/2021 | Igawa et al. | |
| 11,066,483 B2 | 7/2021 | Nezu et al. | |
| 11,124,576 B2 | 9/2021 | Igawa et al. | |
| 11,142,587 B2 | 10/2021 | Igawa et al. | |
| 11,168,344 B2 | 11/2021 | Igawa et al. | |
| 11,248,053 B2 | 2/2022 | Igawa et al. | |
| 11,332,533 B2 | 5/2022 | Igawa et al. | |
| 2001/0001663 A1 | 5/2001 | Kishimoto et al. | |
| 2001/0006796 A1 | 7/2001 | Briggs et al. | |
| 2002/0028178 A1 | 3/2002 | Hanna et al. | |
| 2002/0062010 A1 | 5/2002 | Arathoon et al. | |
| 2002/0142374 A1 | 10/2002 | Gallo et al. | |
| 2002/0147326 A1 | 10/2002 | Chaiklin et al. | |
| 2002/0155537 A1 | 10/2002 | Carter et al. | |
| 2002/0164339 A1 | 11/2002 | Do et al. | |
| 2002/0164668 A1 | 11/2002 | Durham et al. | |
| 2002/0187150 A1 | 12/2002 | Mihara et al. | |
| 2002/0193571 A1 | 12/2002 | Carter et al. | |
| 2002/0197706 A1 | 12/2002 | Nadkarni et al. | |
| 2003/0073161 A1 | 4/2003 | Briggs et al. | |
| 2003/0078385 A1 | 4/2003 | Arathoon et al. | |
| 2003/0082612 A1 | 5/2003 | Snodgrass et al. | |
| 2003/0148409 A1 | 8/2003 | Rossi et al. | |
| 2003/0187225 A1 | 10/2003 | Penichet et al. | |
| 2003/0190311 A1 | 10/2003 | Dall'Acqua et al. | |
| 2003/0207346 A1 | 11/2003 | Arathoon et al. | |
| 2003/0219441 A1 | 11/2003 | Thorpe et al. | |
| 2003/0224397 A1 | 12/2003 | Lowman et al. | |
| 2004/0002587 A1 | 1/2004 | Watkins et al. | |
| 2004/0071706 A1 | 4/2004 | Ito et al. | |
| 2004/0081651 A1 | 4/2004 | Karpusas et al. | |
| 2004/0091475 A1 | 5/2004 | Tsuchiya et al. | |
| 2004/0219643 A1 | 11/2004 | Winter et al. | |
| 2004/0236080 A1 | 11/2004 | Aburatani et al. | |
| 2004/0242847 A1 | 12/2004 | Fukushima et al. | |
| 2005/0095243 A1 | 5/2005 | Chan et al. | |
| 2005/0118174 A1 | 6/2005 | Presta | |
| 2005/0130224 A1 | 6/2005 | Saito et al. | |
| 2005/0142133 A1 | 6/2005 | Lazar et al. | |
| 2005/0142635 A1 | 6/2005 | Tsuchiya et al. | |
| 2005/0158825 A1 | 7/2005 | Power et al. | |
| 2005/0164352 A1 | 7/2005 | Lauder | |
| 2005/0191293 A1 | 9/2005 | Deshpande et al. | |
| 2005/0244403 A1 | 11/2005 | Lazar et al. | |
| 2005/0261229 A1 | 11/2005 | Gillies | |
| 2005/0266425 A1 | 12/2005 | Zauderer et al. | |
| 2006/0019342 A1 | 1/2006 | Dall Acqua et al. | |
| 2006/0024298 A1 | 2/2006 | Lazar et al. | |
| 2006/0057149 A1 | 3/2006 | Johnson et al. | |
| 2006/0058511 A1 | 3/2006 | Tanikawa et al. | |
| 2006/0063228 A1 | 3/2006 | Kasaian et al. | |
| 2006/0074225 A1 | 4/2006 | Chamberlain | |
| 2006/0134105 A1 | 6/2006 | Lazar | |
| 2006/0134709 A1 | 6/2006 | Stavenhagen et al. | |
| 2006/0134805 A1 | 6/2006 | Berg et al. | |
| 2006/0141456 A1 | 6/2006 | Edwards et al. | |
| 2006/0159673 A1 | 7/2006 | Kojima | |
| 2006/0160184 A1 | 7/2006 | Hoogenboom et al. | |
| 2006/0194280 A1 | 8/2006 | Dillon et al. | |
| 2006/0204493 A1 | 9/2006 | Huang et al. | |
| 2006/0235208 A1 | 10/2006 | Lazar et al. | |
| 2006/0269989 A1 | 11/2006 | Miyazaki et al. | |
| 2006/0275282 A1 | 12/2006 | Moore et al. | |
| 2006/0292147 A1 | 12/2006 | Yoshizaki et al. | |
| 2007/0036785 A1 | 2/2007 | Kishimoto et al. | |
| 2007/0041978 A1 | 2/2007 | Hattori et al. | |
| 2007/0054354 A1 | 3/2007 | Humphreys et al. | |
| 2007/0059312 A1 | 3/2007 | Baca et al. | |
| 2007/0087381 A1 | 4/2007 | Kojima | |
| 2007/0110757 A1 | 5/2007 | Wei et al. | |
| 2007/0134234 A1 | 6/2007 | Smith et al. | |
| 2007/0148163 A1 | 6/2007 | Takahashi et al. | |
| 2007/0148164 A1 | 6/2007 | Farrington et al. | |
| 2007/0148167 A1 | 6/2007 | Strohl | |
| 2007/0178092 A1 | 8/2007 | Bolt et al. | |
| 2007/0212357 A1 | 9/2007 | Pons et al. | |
| 2007/0224188 A1 | 9/2007 | Allan et al. | |
| 2007/0231329 A1 | 10/2007 | Lazar et al. | |
| 2007/0254831 A1 | 11/2007 | Mezo et al. | |
| 2007/0287170 A1 | 12/2007 | Davis et al. | |
| 2008/0063635 A1 | 3/2008 | Takahashi et al. | |
| 2008/0075712 A1 | 3/2008 | Hattori et al. | |
| 2008/0166756 A1 | 7/2008 | Tsuchiya et al. | |
| 2008/0206229 A1 | 8/2008 | Ono et al. | |
| 2008/0317758 A9 | 12/2008 | Presta | |
| 2009/0117097 A1 | 5/2009 | Igawa et al. | |
| 2009/0208416 A1 | 8/2009 | Moretta et al. | |
| 2009/0221803 A1 | 9/2009 | Dall'Acqua et al. | |
| 2009/0263392 A1 | 10/2009 | Igawa et al. | |
| 2009/0324589 A1 | 12/2009 | Igawa et al. | |
| 2010/0003254 A1 | 1/2010 | Hattori et al. | |
| 2010/0004429 A1 | 1/2010 | Kai et al. | |
| 2010/0008907 A1 | 1/2010 | Nishimoto et al. | |
| 2010/0015133 A1 | 1/2010 | Igawa et al. | |
| 2010/0055092 A1 | 3/2010 | Hasegawa et al. | |
| 2010/0105874 A1 | 4/2010 | Schuurman et al. | |
| 2010/0178298 A1 | 7/2010 | Lindhofer | |
| 2010/0221252 A1 | 9/2010 | Bigler et al. | |
| 2010/0239577 A1 | 9/2010 | Igawa et al. | |
| 2010/0286374 A1 | 11/2010 | Kannan et al. | |
| 2010/0291072 A1 | 11/2010 | Lowman et al. | |
| 2010/0298542 A1 | 11/2010 | Igawa et al. | |
| 2010/0331527 A1 | 12/2010 | Davis et al. | |
| 2011/0021755 A1 | 1/2011 | Lazar et al. | |
| 2011/0076275 A1 | 3/2011 | Igawa et al. | |
| 2011/0111406 A1 | 5/2011 | Igawa et al. | |
| 2011/0123532 A1 | 5/2011 | Gurney et al. | |
| 2011/0129459 A1 | 6/2011 | Kuramochi et al. | |
| 2011/0236374 A1 | 9/2011 | Shitara et al. | |
| 2011/0245473 A1 | 10/2011 | Igawa et al. | |
| 2011/0287009 A1 | 11/2011 | Scheer et al. | |
| 2012/0009188 A1 | 1/2012 | Behrens | |
| 2012/0010387 A1 | 1/2012 | Niwa et al. | |
| 2012/0028304 A1 | 2/2012 | Dahiyat et al. | |
| 2012/0065379 A1 | 3/2012 | Igawa et al. | |
| 2012/0071634 A1 | 3/2012 | Igawa et al. | |
| 2012/0149876 A1 | 6/2012 | Von Kreudenstein | |
| 2012/0237517 A1 | 9/2012 | Hattori et al. | |
| 2012/0238729 A1 | 9/2012 | Kuramochi et al. | |
| 2013/0011866 A1 | 1/2013 | Igawa et al. | |
| 2013/0018174 A1 | 1/2013 | Igawa et al. | |
| 2013/0030156 A1 | 1/2013 | Apostolou et al. | |
| 2013/0039913 A1 | 2/2013 | Labrijn et al. | |
| 2013/0052196 A1 | 2/2013 | Apostolou et al. | |
| 2013/0085199 A1 | 4/2013 | Tamori et al. | |
| 2013/0101581 A1 | 4/2013 | Kuramochi et al. | |
| 2013/0115208 A1 | 5/2013 | Ho et al. | |

(56) References Cited

U.S. PATENT DOCUMENTS

| | | |
|---|---|---|
| 2013/0195849 A1 | 8/2013 | Spreter et al. |
| 2013/0330345 A1 | 12/2013 | Igawa et al. |
| 2014/0037632 A1 | 2/2014 | Igawa et al. |
| 2014/0051833 A1 | 2/2014 | Fischer et al. |
| 2014/0112883 A1 | 4/2014 | Ponath et al. |
| 2014/0112914 A1 | 4/2014 | Nezu et al. |
| 2014/0154270 A1* | 6/2014 | Wang ............... B01D 15/3809 424/177.1 |
| 2014/0303356 A1 | 10/2014 | Gramer et al. |
| 2014/0370018 A1 | 12/2014 | Igawa et al. |
| 2014/0370020 A1 | 12/2014 | Kuramochi et al. |
| 2014/0377253 A1 | 12/2014 | Harding et al. |
| 2015/0118184 A1 | 4/2015 | Kawai |
| 2015/0274809 A1 | 10/2015 | Igawa et al. |
| 2015/0284465 A1 | 10/2015 | Igawa et al. |
| 2015/0297820 A1* | 10/2015 | Kawai ............... A61M 1/3679 210/690 |
| 2015/0315278 A1 | 11/2015 | Igawa et al. |
| 2015/0337053 A1 | 11/2015 | McCarthy et al. |
| 2016/0024147 A1* | 1/2016 | Tustian ............... C07K 16/065 530/387.3 |
| 2016/0159915 A1 | 6/2016 | Igawa et al. |
| 2016/0222129 A1 | 8/2016 | Igawa et al. |
| 2016/0229908 A1 | 8/2016 | Igawa et al. |
| 2016/0229915 A1 | 8/2016 | Igawa et al. |
| 2017/0022293 A1 | 1/2017 | Igawa et al. |
| 2017/0145111 A1 | 5/2017 | Hattori et al. |
| 2017/0267783 A1 | 9/2017 | Nezu et al. |
| 2017/0275332 A1 | 9/2017 | Igawa et al. |
| 2017/0283483 A1 | 10/2017 | Igawa et al. |
| 2017/0342154 A1 | 11/2017 | Igawa et al. |
| 2018/0002443 A1 | 1/2018 | Hattori et al. |
| 2018/0051307 A1 | 2/2018 | Igawa et al. |
| 2018/0057607 A1 | 3/2018 | Igawa et al. |
| 2018/0142027 A1 | 5/2018 | Igawa et al. |
| 2018/0162902 A1 | 6/2018 | Igawa et al. |
| 2018/0244800 A1 | 8/2018 | Hattori et al. |
| 2018/0244805 A1 | 8/2018 | Nezu et al. |
| 2018/0344630 A1 | 12/2018 | Igawa et al. |
| 2019/0062368 A1 | 2/2019 | Igawa et al. |
| 2019/0062638 A1 | 2/2019 | Igawa et al. |
| 2019/0112390 A1 | 4/2019 | Hattori et al. |
| 2019/0211081 A1 | 7/2019 | Igawa et al. |
| 2019/0315884 A1 | 10/2019 | Igawa et al. |
| 2019/0352334 A1 | 11/2019 | Igawa et al. |
| 2019/0352421 A1 | 11/2019 | Adams et al. |
| 2019/0359728 A1 | 11/2019 | Hattori et al. |
| 2020/0087380 A1 | 3/2020 | Teranishi et al. |
| 2020/0123256 A1 | 4/2020 | Hoshino et al. |
| 2020/0207805 A1 | 7/2020 | Igawa et al. |
| 2020/0223940 A1 | 7/2020 | Teranishi et al. |
| 2020/0277402 A1 | 9/2020 | Hattori et al. |
| 2020/0354473 A1 | 11/2020 | Teranishi et al. |
| 2021/0040147 A1 | 2/2021 | Igawa et al. |
| 2021/0107994 A1 | 4/2021 | Shima et al. |
| 2021/0107995 A1 | 4/2021 | Hattori et al. |
| 2021/0189006 A1 | 6/2021 | Saeki et al. |
| 2021/0292360 A1 | 9/2021 | Igawa et al. |
| 2021/0324109 A1 | 10/2021 | Igawa et al. |
| 2021/0380717 A1 | 12/2021 | Hattori et al. |
| 2022/0010030 A1 | 1/2022 | Igawa et al. |
| 2022/0064264 A1 | 3/2022 | Igawa et al. |
| 2022/0213217 A1 | 7/2022 | Hattori et al. |
| 2022/0251225 A1 | 8/2022 | Igawa et al. |
| 2022/0267470 A1 | 8/2022 | Igawa et al. |
| 2022/0267822 A1 | 8/2022 | Igawa et al. |
| 2022/0041756 A1 | 10/2022 | Nezu et al. |

FOREIGN PATENT DOCUMENTS

| | | |
|---|---|---|
| CA | 2 203 182 | 5/1996 |
| CA | 2 331 641 | 11/1999 |
| CA | 2 019 559 | 1/2002 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 700 986 | 4/2009 |
| CN | 1842540 | 10/2006 |
| CN | 101198698 | 6/2008 |
| CN | 101883588 | 11/2010 |
| CN | 102471378 | 5/2012 |
| CN | 102782131 | 11/2012 |
| CN | 102858366 | 1/2013 |
| CN | 102946906 | 2/2013 |
| CN | 103298937 | 9/2013 |
| CN | 101874042 | 9/2018 |
| DE | 198 19 846 | 11/1999 |
| EP | 0 369 566 | 5/1990 |
| EP | 437 622 | 7/1991 |
| EP | 0 329 185 | 4/1994 |
| EP | 0 637 593 | 2/1995 |
| EP | 0 404 097 | 9/1996 |
| EP | 0 774 511 | 5/1997 |
| EP | 0 783 893 | 7/1997 |
| EP | 811 691 | 12/1997 |
| EP | 1 069 185 | 1/2001 |
| EP | 1 220 923 | 7/2002 |
| EP | 1 327 681 | 7/2003 |
| EP | 1 378 520 | 1/2004 |
| EP | 1 510 943 | 3/2005 |
| EP | 0 979 281 | 7/2005 |
| EP | 1 605 058 | 12/2005 |
| EP | 1 674 111 | 6/2006 |
| EP | 1 693 448 | 8/2006 |
| EP | 1 701 979 | 9/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 2 006 3 81 | 12/2008 |
| EP | 2 009 101 | 12/2008 |
| EP | 2 031 064 | 3/2009 |
| EP | 1 505 148 | 4/2009 |
| EP | 2 107 115 | 10/2009 |
| EP | 2 194 006 | 6/2010 |
| EP | 2 194 066 | 6/2010 |
| EP | 2 196 541 | 6/2010 |
| EP | 2 202 245 | 6/2010 |
| EP | 2 206 775 | 7/2010 |
| EP | 2 236 604 | 10/2010 |
| EP | 2 275 443 | 1/2011 |
| EP | 1 688 488 | 8/2011 |
| EP | 2 354 161 | 8/2011 |
| EP | 2 409 991 | 1/2012 |
| EP | 1 688 488 B9 | 3/2012 |
| EP | 2 445 936 | 5/2012 |
| EP | 2 238 985 | 8/2012 |
| EP | 2 522 724 | 11/2012 |
| EP | 2 526 963 | 11/2012 |
| EP | 2 543 727 | 1/2013 |
| EP | 2 543 730 A | 1/2013 |
| EP | 2 576 621 | 4/2013 |
| EP | 2 644 698 | 10/2013 |
| EP | 2 647 707 | 10/2013 |
| EP | 2 698 431 A | 2/2014 |
| EP | 2 905 290 | 8/2015 |
| EP | 2 914 634 | 9/2015 |
| EP | 3 059 246 A | 8/2016 |
| JP | S63-52890 | 3/1988 |
| JP | 2-028200 | 1/1990 |
| JP | 2-145187 | 6/1990 |
| JP | H03-500644 | 2/1991 |
| JP | 5-184383 | 7/1993 |
| JP | 5-199894 | 8/1993 |
| JP | 5-203652 | 8/1993 |

(56) References Cited

FOREIGN PATENT DOCUMENTS

| | | |
|---|---|---|
| JP | 5-213775 | 8/1993 |
| JP | 5-304992 | 11/1993 |
| JP | 07-67688 | 3/1995 |
| JP | 7-503622 | 4/1995 |
| JP | 8-500979 | 2/1996 |
| JP | 8-510555 | 11/1996 |
| JP | 09-506001 | 6/1997 |
| JP | 10-505231 | 5/1998 |
| JP | 10-165184 | 6/1998 |
| JP | 10-511085 | 10/1998 |
| JP | 11-500915 | 1/1999 |
| JP | 11-500916 | 1/1999 |
| JP | 11-71288 | 3/1999 |
| JP | 11-504007 | 4/1999 |
| JP | 11-506310 | 6/1999 |
| JP | 3032287 | 4/2000 |
| JP | 2001-506135 | 5/2001 |
| JP | 2001-513999 | 9/2001 |
| JP | 2001-518930 | 10/2001 |
| JP | 2001-523971 | 11/2001 |
| JP | 2002-514406 | 5/2002 |
| JP | 2002-518041 | 6/2002 |
| JP | 2002-543822 | 12/2002 |
| JP | 2002-544173 | 12/2002 |
| JP | 2003-055398 | 2/2003 |
| JP | 2003-509049 | 3/2003 |
| JP | 2003-515323 | 5/2003 |
| JP | 2004-086862 | 3/2004 |
| JP | 2004-511426 | 4/2004 |
| JP | 2004-321100 | 11/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2005-537009 | 12/2005 |
| JP | 2008-512995 | 5/2008 |
| JP | 2008-523140 | 7/2008 |
| JP | 2008-538920 | 11/2008 |
| JP | 2009-500458 | 1/2009 |
| JP | 2009-527499 | 7/2009 |
| JP | 2010-522701 | 7/2010 |
| JP | 2010-532369 | 10/2010 |
| JP | 2011-508604 | 3/2011 |
| JP | 2012-510281 | 5/2012 |
| JP | 2012-515160 | 7/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 2015-510764 | 4/2015 |
| JP | 5717624 | 5/2015 |
| JP | 2015-130883 | 7/2015 |
| JP | 5787446 | 9/2015 |
| JP | 2016-69329 | 5/2016 |
| JP | 6534615 | 6/2019 |
| KR | 2008/0013875 | 2/2008 |
| KR | 2010/0074221 | 7/2010 |
| KR | 2012/0123055 | 11/2012 |
| KR | 2013/0102113 | 9/2013 |
| KR | 2013/0102640 | 9/2013 |
| KR | 2013/0130765 | 12/2013 |
| KR | 10-1960109 | 3/2019 |
| MX | 9905856 A | 7/2000 |
| MX | 349057 | 7/2020 |
| NO | 20062087 | 7/2006 |
| RU | 94028282 | 7/1996 |
| RU | 2232773 | 7/2004 |
| RU | 2266298 | 12/2005 |
| RU | 2339696 | 11/2008 |
| RU | 2355705 | 5/2009 |
| TW | 2007/14313 | 4/2007 |
| TW | 2007/22517 | 6/2007 |
| TW | I452135 | 9/2014 |
| TW | I452136 | 9/2014 |
| TW | 2016/00112 | 1/2016 |
| WO | WO 89/01343 | 2/1989 |
| WO | WO 91/01335 | 2/1991 |
| WO | WO 91/08770 | 6/1991 |
| WO | WO 92/19759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/14710 | 6/1995 |
| WO | WO 95/33844 | 12/1995 |
| WO | WO 96/01653 | 1/1996 |
| WO | WO 96/04925 | 2/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 96/33208 | 10/1996 |
| WO | WO 96/34892 | 11/1996 |
| WO | WO 97/09351 | 3/1997 |
| WO | WO 97/10354 | 3/1997 |
| WO | WO 97/31108 | 8/1997 |
| WO | WO 98/03546 | 1/1998 |
| WO | WO 98/28331 | 7/1998 |
| WO | WO 98/41641 | 9/1998 |
| WO | WO 98/42378 | 10/1998 |
| WO | WO 98/50431 | 11/1998 |
| WO | WO 99/02567 | 1/1999 |
| WO | WO 99/03495 | 1/1999 |
| WO | WO 99/10494 | 3/1999 |
| WO | WO 99/018212 | 4/1999 |
| WO | WO 99/51743 | 10/1999 |
| WO | WO 99/58572 | 11/1999 |
| WO | WO 99/67359 | 12/1999 |
| WO | WO 00/018806 | 4/2000 |
| WO | WO 00/42072 | 7/2000 |
| WO | WO 00/044788 | 8/2000 |
| WO | WO 00/067795 | 11/2000 |
| WO | WO 00/069462 | 11/2000 |
| WO | WO 01/019992 | 3/2001 |
| WO | WO 01/030854 | 5/2001 |
| WO | WO 01/036486 | 5/2001 |
| WO | WO 01/044282 | 6/2001 |
| WO | WO 01/064713 | 9/2001 |
| WO | WO 01/066737 | 9/2001 |
| WO | WO 01/070775 | 9/2001 |
| WO | WO 01/074388 | 10/2001 |
| WO | WO 01/079494 | 10/2001 |
| WO | WO 01/082899 | 11/2001 |
| WO | WO 01/090192 | 11/2001 |
| WO | WO 01/097858 | 12/2001 |
| WO | WO 02/004021 | 1/2002 |
| WO | WO 02/006838 | 1/2002 |
| WO | WO 02/022212 | 3/2002 |
| WO | WO 02/030463 | 4/2002 |
| WO | WO 02/033072 | 4/2002 |
| WO | WO 02/033073 | 4/2002 |
| WO | WO 02/060919 | 8/2002 |
| WO | WO 02/072605 | 9/2002 |
| WO | WO 02/078612 | 10/2002 |
| WO | WO 03/000883 | 1/2003 |
| WO | WO 03/012069 | 2/2003 |
| WO | WO 03/020949 | 3/2003 |
| WO | WO 03/033654 | 4/2003 |
| WO | WO 03/035835 | 5/2003 |
| WO | WO 03/042231 | 5/2003 |
| WO | WO 03/074679 | 9/2003 |
| WO | WO 03/087163 | 10/2003 |
| WO | WO 03/091424 | 11/2003 |
| WO | WO 03/104425 | 12/2003 |
| WO | WO 03/105757 | 12/2003 |
| WO | WO 2004/003019 | 1/2004 |
| WO | WO 2004/009618 | 1/2004 |

(56) References Cited

FOREIGN PATENT DOCUMENTS

| | | |
|---|---|---|
| WO | WO 2004/016740 | 2/2004 |
| WO | WO 2004/019966 | 3/2004 |
| WO | WO 2004/020579 | 3/2004 |
| WO | WO 2004/033499 | 4/2004 |
| WO | WO 2004/035607 | 4/2004 |
| WO | WO 2004/060919 | 7/2004 |
| WO | WO 2004/065611 | 8/2004 |
| WO | WO 2004/068931 | 8/2004 |
| WO | WO 2004/081048 | 9/2004 |
| WO | WO 2004/087763 | 10/2004 |
| WO | WO 2004/096273 | 11/2004 |
| WO | WO 2004/097041 | 11/2004 |
| WO | WO 2004/099249 | 11/2004 |
| WO | WO 2004/111233 | 12/2004 |
| WO | WO 2004/113387 | 12/2004 |
| WO | WO 2005/005604 | 1/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/056604 | 6/2005 |
| WO | WO 2005/056606 | 6/2005 |
| WO | WO 2005/059106 | 6/2005 |
| WO | WO 2005/062916 | 7/2005 |
| WO | WO 2005/063815 | 7/2005 |
| WO | WO 2005/067620 | 7/2005 |
| WO | WO 2005/092925 | 10/2005 |
| WO | WO 2005/107784 | 11/2005 |
| WO | WO 2005/112564 | 12/2005 |
| WO | WO 2005/118635 | 12/2005 |
| WO | WO 2005/121180 | 12/2005 |
| WO | WO 2005/123126 | 12/2005 |
| WO | WO 2006/004663 | 1/2006 |
| WO | WO 2006/019447 | 2/2006 |
| WO | WO 2006/020114 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047340 | 5/2006 |
| WO | WO 2006/047350 | 5/2006 |
| WO | WO 2006/050491 | 5/2006 |
| WO | WO 2006/065208 | 6/2006 |
| WO | WO 2006/067913 | 6/2006 |
| WO | WO 2006/071877 | 7/2006 |
| WO | WO 2006/075668 | 7/2006 |
| WO | WO 2006/105338 | 10/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/121852 | 11/2006 |
| WO | WO 2007/009065 | 1/2007 |
| WO | WO 2007/024535 | 3/2007 |
| WO | WO 2007/060411 | 5/2007 |
| WO | WO 2007/108559 | 9/2007 |
| WO | WO 2007/114319 | 10/2007 |
| WO | WO 2007/114325 | 10/2007 |
| WO | WO 2007/142325 | 12/2007 |
| WO | WO 2007/143168 | 12/2007 |
| WO | WO 2007/145941 | 12/2007 |
| WO | WO 2007/147901 | 12/2007 |
| WO | WO 2008/043822 | 4/2008 |
| WO | WO 2008/090960 | 7/2008 |
| WO | WO 2008/092117 | 7/2008 |
| WO | WO 2008/119353 | 10/2008 |
| WO | WO 2008/145141 | 12/2008 |
| WO | WO 2008/145142 | 12/2008 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/080252 | 7/2009 |
| WO | WO 2009/080253 | 7/2009 |
| WO | WO 2009/084659 | 7/2009 |
| WO | WO 2009/089004 | 7/2009 |
| WO | WO 2009/100309 | 8/2009 |
| WO | WO 2009/120922 | 10/2009 |
| WO | WO 2009/125825 | 10/2009 |
| WO | WO 2009/134776 | 11/2009 |
| WO | WO 2009/139822 | 11/2009 |
| WO | WO 2010/034441 | 4/2010 |
| WO | WO 2010/035769 | 4/2010 |
| WO | WO 2010/063746 | 6/2010 |
| WO | WO 2010/064090 | 6/2010 |
| WO | WO 2010/080065 | 7/2010 |
| WO | WO 2010/085682 | 7/2010 |
| WO | WO 2010/102251 | 9/2010 |
| WO | WO 2010/106180 | 9/2010 |
| WO | WO 2010/107109 | 9/2010 |
| WO | WO 2010/107110 | 9/2010 |
| WO | WO 2010/115589 | 10/2010 |
| WO | WO 2010/120561 | 10/2010 |
| WO | WO 2010/151792 | 12/2010 |
| WO | WO 2011/090088 | 2/2011 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2011/147986 | 12/2011 |
| WO | WO 2012/020096 | 2/2012 |
| WO | WO 2012/067176 | 5/2012 |
| WO | WO 2012/073985 | 6/2012 |
| WO | WO 2012/145238 | 10/2012 |
| WO | WO 2013/060867 | 5/2013 |
| WO | WO 2013/124450 | 8/2013 |
| WO | WO 2013/131866 | 9/2013 |
| WO | WO 2013/136186 | 9/2013 |
| WO | WO 2013/157954 | 10/2013 |
| WO | WO 2014/028354 | 2/2014 |
| WO | WO 2014/054804 | 4/2014 |
| WO | WO 2014/067011 | 5/2014 |
| WO | WO 2015/046467 | 4/2015 |
| WO | WO 2015/063339 | 5/2015 |
| WO | WO 2015/194233 | 12/2015 |
| WO | WO 2016/125495 | 8/2016 |
| WO | WO 2016/159213 | 10/2016 |
| WO | WO 2016/164708 | 10/2016 |
| WO | WO 2016/166014 | 10/2016 |
| WO | WO 2016/171202 | 10/2016 |
| WO | WO 2017/115773 | 7/2017 |
| WO | WO 2017/129585 | 8/2017 |
| WO | WO 2017/188356 | 11/2017 |
| WO | WO 2018/181870 | 10/2018 |
| WO | WO 2019/088143 | 5/2019 |
| WO | WO 2021/201202 | 10/2021 |

OTHER PUBLICATIONS

Annex 1, submitted by the patentee during examination proceedings on Sep. 18, 2015 (cited in oppositions filed against European Patent No. 2 647 707 on May 31, 2019 and Jun. 12, 2019), 5 pages.
Das et al., "Producing Bispecific and Bifunctional Antibodies," Methods Mol Med, 2005, 109:329-46.

(56) References Cited

OTHER PUBLICATIONS

Demanet et al., "Treatment of murine B cell lymphoma with bispecific monoclonal antibodies (anti-idiotype x anti-CD3)," J Immunol, Aug. 1, 1991, 147(3):1091-7.

English translation of EP 11845786 (cited in oppositions filed against European Patent No. 2 647 707 on May 31, 2019 and Jun. 12, 2019), 123 pages.

Graca, The Immune Synapse as a Novel Target for Therapy, 2008, pp. 59-61.

Haagen et al., "Evaluation of Fcγ receptor mediated T-cell activation by two purified CD3 x CD19 bispecific monoclonal antibodies with hybrid Fc domains," Ther Immunol, Oct. 1994, 1(5):279-87.

Haagen et al., "Interaction of human monocyte Fc gamma receptors with rat IgG2b. A new indicator for the Fc gamma RIIa (R-H131) polymorphism," J Immunol, Feb. 15, 1995, 154(4):1852-60.

Hezareh et al., "Effector Function Activities of a Panel of Mutants of a Broadly Neutralizing Antibody against Human Immunodeficiency Virus Type 1," J Virol, Dec. 2001, 75(24):12161-8.

Hoseini et al., "Immunotherapy of hepatocellular carcinoma using chimeric antigen receptors and bispecific antibodies," Cancer Lett, Jul. 28, 2017, 399:44-52. doi: 10.1016/j.canlet.2017.04.013. Epub Apr. 17, 2017.

Ishiguro et al., "An anti-glypican 3/CD3 bispecific T cell-redirecting antibody for treatment of solid tumors," Sci Transl Med, Oct. 4, 2017, 9(410), pii: eaal4291. doi:10.1126/scitranslmed.aal4291.

Kasthuri et al., "Role of Tissue Factor in Cancer," J Clin Oncol, Oct. 10, 2009, 27(29):4834-8. doi: 10.1200/JCO.2009.22.6324. Epub Sep. 8, 2009.

King, Applications and Engineering of Monoclonal Antibodies, 2005, pp. 146-147.

Kontermann, "The Role of the Fc Region," Bispecific Antibodies, 2011, 296-8.

Link et al., "Anti-CD-3-Based Bispecific Antibody Designed for Therapy of Human B-Cell Malignancy Can Induce T-Cell Activation by Antigen-Dependent and Antigen-Independent Mechanisms," Int J Cancer, Jul. 17, 1998, 77(2):251-6.

Little, Recombinant Antibodies for Immunotherapy, 2009, pp. 133-134.

Matzku et al., Antibodies in Diagnosis and Therapy, Technologies, Mechanisms and Clinical Data, 1999, p. 7.

Nelson et al., "5.2 Complementary Interactions between Proteins and Ligands: The Immune System and Immunoglobulins," Lehninger, Principles of Biochemistiy, 5th Ed., 2008, p. 171.

Nimmerjahn et al., "Fcγ Receptors as Regulators of Immune Responses," Nat Rev Immunol, Jan. 2008, 8(1):34-47.

Nitta et al., "Bispecific F(ab')2 monomer prepared with anti-CD3 and anti-tumor monoclonal antibodies is most potent in induction of cytolysis of human T cells," Eur J Immunol, Aug. 1989, 19(8):1437-41.

Oganesyan et al., "Structural characterization of a human Fc fragment engineered for lack of effector functions," Acta Crystallogr D Biol Crystallogr, Jun. 2008, 64(Pt 6):700-4. doi: 10.1107/S0907444908007877. Epub May 14, 2008.

Parren et al., "Induction of T-cell proliferation by recombinant mouse and chimeric mouse/human anti-CD3 monoclonal antibodies," Res Immunol, Nov.-Dec. 1991, 142(9):749-63.

Ravetch et al., "Fc Receptors," Annu Rev Immunol, Apr. 1991, 9:457-92.

Routledge et al., "A humanized monovalent CD3 antibody which can activate homologous complement," Eur J Immunol, Nov. 1991, 21(11):2717-25.

Salnikov et al., "Targeting of cancer stem cell marker EpCAM by bispecific antibody EpCAMxCD3 inhibits pancreatic carcinoma," J Cell Mol Med, Sep. 2009, 13(9B):4023-33. doi: 10.1111/j.1582-4934.2009.00723.x.

Segal et al., "Production of Bispecific Antibodies," Current Protocols in Immunology, 1995, Unit 2.13.1-2.13.16.

Sequence alignments (cited in oppositions filed against European Patent No. 2 647 707 on May 31, 2019 and Jun. 12, 2019), 6 pages.

Strauss et al., "Without Prior Stimulation, Tumor-associated Lymphocytes from Malignant Effusions Lyse Autologous Tumor Cells in the Presence of Bispecific Antibody HEA125xOKT3," Clin Cancer Res, Jan. 1999, 5(1):171-80.

Xu et al., "In Vitro Characterization of Five Humanized OKT3 Effector Function Variant Antibodies," Cell Immunol, Feb. 25, 2000, 200(1):16-26.

U.S. Appl. No. 16/815,089, Igawa el al., filed Mar. 11, 2020.
U.S. Appl. No. 16/448,088, Igawa et al., filed Jun. 21, 2019.
U.S. Appl. No. 16/155,673, Igawa el al., filed Oct. 9, 2018 (abandoned).
U.S. Appl. No. 16/825,513, Hattori et al., filed Mar. 20, 2020.
U.S. Appl. No. 12/295,039, Igawa et al., filed Jan. 20, 2009.
U.S. Appl. No. 15/490,936, Igawa et al., filed Apr. 19, 2017.
U.S. Appl. No. 13/990,088, Nezu el al., filed Dec. 19, 2013.

ALPROLIX Intravenous, 2019, 16 pages (with English translation).

Astermark et al., "A randomized comparison of bypassing agents in hemophilia complicated by an inhibitor: the FEIBA NovoSeven Comparative (FENOC) Study," Blood, Jan. 15, 2007, 109(2):546-51. Epub Sep. 21, 2006.

Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.

Coppola et al., "Acquired Inhibitors of Coagulation Factors: Part I—Acquired Hemophilia A" Semin Thromb Hemost, Jul. 2012, 38(5):433-46. doi: 10.1055/s-0032-1315757. Epub Jun. 27, 2012.

Franchini et al., "Acquired haemophilia A: A 2013 update," Thromb Haemost, Dec. 2013, 110(6):1114-20. doi:10.1160/TH13-05-0363. Epub Sep. 5, 2013.

Guidelines for the management of hemophilia, World Federation of Hemophilia, 2005, 52 pages.

Hagiwara et al., "Effect of Emicizumab in improving coagulation ability in the presence of minor amount of Factor IX," Japanese Journal of Thrombosis and Hemostasis, 2017, 28(2):190 0-012 (with English translation).

U.S. Appl. No. 16/815,089, Igawa et al., filed Mar. 11, 2020.

"Hemostatic Therapy Guideline for Inhibitor-negative Hemophilia Patients," Japanese Journal of Thrombosis and Hemostasis, 2013, 24(6):619-639 (with English translation).

"Hemostatic Therapy Guideline for Inhibitor-positive Hemophilia Patients," Japanese Journal of Thrombosis and Hemostasis, 2013, 24(6):640-658 (with English translation).

Kruse-Jarres, "Inhibitors: our greatest challenge. Can we minimize the incidence?," Haemophilia, Jan. 2013, 19(Suppl 1):2-7. doi: 10.1111/hae. 12049.

Lillicrap, "von Willebrand disease: advances in pathogenetic understanding, diagnosis, and therapy," Blood, Nov. 28, 2013, 122(23):3735-40. doi: 10.1182/blood-2013-06-498303. Epub Sep. 24, 2013.

Minami et al., "Bispecific Antibody ACE910 Improves Coagulation Function in Plasma of Patients with Factor XI Deficiency," Japanese Journal of Thrombosis and Hemostasis, 2015, 26(2):188 0-024 (with English translation).

Miyata, "Factor IX Abnormality—Molecular defects of Factor IX," Japanese Journal of Thrombosis and Hemostasis, 1991, 2(1):1-11 (with English translation).

Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-213. doi: 10. 1111/jth.12474.

Muto et al., "Anti-factor IXa/X bispecific antibody ACE910 prevents joint bleeds in a long-term primate model of acquired hemophilia A," Blood, Nov. 13, 2014, 124(20):3165-71. doi: 10.1182/blood-2014-07-585737. Epub Oct. 1, 2014.

Nishimura et al., "Factor IX Fukuoka. Substitution of ASN$^{92}$ by His in the second epidermal growth factor-like domain results in defective interaction with factors VIIIa/X," Journal of Biological Chemistry, 1993, 268(32):24041-24046.

Nogami, "Bispecific Antibody that Substitutes for Factor VIII in the Treatment of Childhood. Hemophilia A," The Japanese Journal of Pediatric Hematology/Oncology, 2016, 53(2):69-74 (with English translation).

(56) References Cited

OTHER PUBLICATIONS

Shima, "The Forefront and Prospects of Hemophilia Treatment," J Jpn Pediatr Soc, Mar. 1, 2017, 121(3):543-552 (with English translation).
Shima et al., "Factor VIII—Mimetic Function of Humanized Bispecific Antibody in Hemophilia. A," N Eng J Med, May 26, 2016, 374(21):2044-2053. doi: 10.1056/NEJMoa1511769.
Tarantino et al., "Safety of human plasma-derived clotting factor products and their role in haemostasis in patients with haemophilia meeting report," Haemophilia, Sep. 2007, 13(5):663-9.
Uchida et al., "A first-in-human phase 1 study of ACE910, a novel factor VIII—m016 imetic bispecific antibody, in healthy subjects," Blood, Mar. 31, 2016, 127(13):1633-1641. doi: 10.1182/blood-2015-06-650226. Epub Dec. 1, 2015.
Chandramohan et al., "Antibody, T-cell and dendritic cell immunotherapy for malignant brain tumors," Future Oncol, Jul. 2013, 9(7):977-90. doi: 10.2217/fon.13.47.
Davie, "A Brief Historical Review of the Waterfall/Cascade of Blood Coagulation," J Biol Chem, Dec. 19, 2003, 278(51):50819-32, Epub Oct. 21, 2003.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Declaration of Dr. Anette Henriksen, signed Apr. 17, 2019 (submitted by the Opponent during EPO opposition procedure for EP 2 006 381), 4 pages.
Fischer et al., "Bispecific Antibodies: Molecules That Enable Novel Therapeutic Strategies," Pathobiology, May 2007, 74(1):3-14.
Granted claims of EP 2 275 443 (submitted on May 24, 2019 by the Patentee during EPO Opposition Procedure for EP 2 202 245), 1 page.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
Wing et al., "Mechanism of First-Dose Cytokine-Release Syndrome by CAMPATH 1-H: Involvement of CD16 (FcγRIII) and CD11a/CD18 (LFA-1) on NK Cells," J Clin Invest, Dec. 15, 1996, 98(12):2819-26.
U.S. Appl. No. 13/257,145, Igawa et al., filed Nov. 22, 2011.
U.S. Appl. No. 16/155,673, Igawa et al., filed Oct. 9, 2018 (agandoned).
U.S. Appl. No. 13/582,073, Kuramochi et al., filed Dec. 20, 2012.
U.S. Appl. No. 15/132,996, Igawa et al., filed Apr. 19, 2016.
U.S. Appl. No. 16/226,798, Hattori et al., filed Dec. 20, 2018.
U.S. Appl. No. 13/990,008, Nezu et al., filed Dec. 19, 2013.
Barrabes et al., "Effect of sialic acid content on glycoprotein pI analyzed by two-dimensional electrophoresis," Electrophoresis, Sep. 2010, 31(17):2903-12. doi: 10.1002/elps.200900764.
Bodelon et al., "Immunoglobulin domains in *Escherichia coli* and other enterobacteria: from pathogenesis to applications in antibody technologies," FEMS Microbiol Rev, Mar. 2013, 37(2):204-50. doi: 10.1111/j.1574-6976.2012.00347.x. Epub Jul. 23, 2012.
InvivoGen, "Review: Immunoglobulin G," 2011, 1 page (downloaded on Jul. 1, 2019 from www.invivogen.com/sites/default/files/invivogen/old/docs/reviews/review-ImmunoglobulinG-invivogen.pdf).
Mariuzza, "The Structural Basis of Antigen-Antibody Recognition," Annu Rev Biophys Biophys Chem., Jun. 1987, 16:139-159.
U.S. Appl. No. 16/448,008, Igawa et al., filed Jun. 21, 2019.
U.S. Appl. No. 15/228,965, Igawa et al., filed Oct. 7, 2016 (abandoned).
U.S. Appl. No. 16/536,385, Hattori et al., filed Aug. 9, 2019.
U.S. Appl. No. 14/018,117, Igawa et al., filed Sep. 5, 2013 (abandoned).
U.S. Appl. No. 14/019,712, Igawa et al., filed Sep. 66, 2013 (abandoned).
Do et al., "A rapid method for determining dynamic binding capacity of resins for the purification of proteins," Protein Expr Purif, Aug. 2008, 60(2):147-50. doi: 10.1016/j.pep.2008.04.009. Epub May 3, 2008.
Pabst et al., "Engineering of novel Staphylococcal Protein A ligands to enable milder elution pH and high dynamic binding capacity," J Chromatogr A, Oct 3, 2014, 1362:180-5. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
U.S. Appl. No. 17/076,938, Igawa et al., filed Oct. 22, 2020.
Carpenter et al., "Non-Fc Receptor-Binding Humanized Anti-CD3 Antibodies Induce Apoptosis of Activated Human T Cells," J Immunol, Dec 1, 2000, 165(11):6205-6213. doi: 10.4049/jimmunol.165.11.6205.
EPO opposition preliminary decision in opposition of EP 2 647 707, dated May 13, 2020, 23 pages.
Adlersberg et al., "The Immunoglobulin Hinge (Interdomain) Region," Ric Clin Lab, Jul.-Sep. 1976, 6(3)491-205.
Astermark et al., "A randomized comparison of bypassing agents in hemophilia complicated by an inhibitor: the FEIBA NovoSeven Comparative (FENOC) Study," Blood, Jan. 15, 2007, 109(2):546-551. Epub Sep. 21, 2006.
Bi et al., "Treatment of hepatocellular carcinoma with a GPC3-targeted bispecific T cell engager," Oncotarget, May 16, 2017, 8(32):52866-52876. doi: 10.18632/oncotarget.17905. eCollection Aug. 8, 2017.
Chernajovsky et al., "Historical Development of Monoclonal Antibody Therapeutics," Therapeutic Antibodies, 2008, pp. 3-7.
Coppola et al., "Acquired Inhibitors of Coagulation Factors: Part I—Acquired Hemophilia A," Semin Thromb Hemost, Jul. 2012, 38(5):433-446, doi: 10.1055/s-0032-1315757. Epub Jun. 27, 2012.
English translation of JP Appn. 2010-266760, dated Aug. 9, 2018 (submitted by Opponent 3 on Mar. 26, 2020 in opposition of EP 2 647 707), 279 pages.
Examination report of EP Appn. 18192844.1 dated May 12, 2019 (submitted by Opponents on Mar. 26, 2020 in opposition of EP 2 647 707), 6 pages.
Franchini et al., "Acquired haemophilia A: A 2013 update," Thromb Haemost, Dec. 2013, 110(6):1114-1120, doi: 10.1160/TH13-05-0363. Epub Sep. 5, 2013.
Guidelines for the Management of Hemophilia, 2005, World Federation of Hemophilia, 52 pages.
Harada et al., "In vitro toxicological support to establish specification limit for anti-CD3 monospecific impurity in a bispecific T cell engager drug, ERY974," Toxicol In Vitro, Aug. 2020, 66:104841, doi: 10.1016/j.tiv.2020.104841. Epub Apr. 1, 2020.
Iwata et al., "Daily ascending dosing in cynomolgus monkeys to mitigate cytokine release syndrome induced by ERY22, surrogate for T-cell redirecting bispecific antibody ERY974 for cancer immunotherapy," Toxicol Appl Pharmacol, Sep. 15, 2019, 379:114657. doi: 10.1016/j.taap.2019.114657. Epub Jul. 19, 2019.
Lejeune et al., "Bispecific, T-Cell-Recruiting Antibodies in B-Cell Malignancies," Frontiers in Immunology, May 7, 2020, 11:762, 20 pages.
Lillicrap, "von Willebrand disease: advances in pathogenetic understanding, diagnosis, and therapy," Blood, Nov. 28, 2013, 122(23):3735-3740. doi: 10.1182/blood-2013-06-498303. Epub Sep. 24, 2013.
Mueller et al., "Humanized Porcine VCAM-Specific Monoclonal Antibodies with Chimeric IgG2/G4 Constant Regions Block Human Leukocyte Binding to Porcine Endothelial Cells," Mol Immunol, Apr. 1997, 34(6):441-452.
Nishimura et al., "Factor IX Fukuoka—Substitution of ASN$^{92}$ by His in the second epidermal growth factor-like domain results in defective interaction with factors VIIIa/X," Journal of Biological Chemistry, Nov. 15, 1993, 268(32)24041-24046.
Runcie et al., "Bi-specific and tri-specific antibodies—the next big thing in solid tumor therapeutics," Molecular Medicine, Sep. 24, 2018, 24(1):50, 15 pages.

(56) References Cited

OTHER PUBLICATIONS

Shima, "The Forefront and Prospects of Hemophilia Treatment," The Journal of the Japan Pediatric Society, Mar. 1, 2017, 121(3):543-552 (with English translation).

Shima et al., "Factor VIII—Mimetic Function of Humanized Bispecific Antibody in Hemophilia A," The New England Journal of Medicine, May 2016, 374(21):2044-2053. doi: 10.1056/NEJMoa1511769.

Shiraiwa et al., "Engineering a bispecific antibody with a common light chain: Identification and optimization of an anti-CD3 epsilon and anti-GPC3 bispecific antibody, ERY974," Methods, Feb. 1, 2019, 154:10-20, doi: 10.1016/j.ynneth.2018.10.005, Epub Oct. 13, 2018.

Szoor et al., "T Cell-Activating Mesenchymal Stem Cells as a Biotherapeutic for HCC," Mol Ther Oncolytics, Jul. 28, 2017, 6:69-79, doi: 10.1016/j.onnto.2017.07.002. eCollection Sep. 15, 2017.

Tarantino et al., "Safety of human plasma-derived clotting factor products and their role in haemostasis in patients with haemophilia: meeting report," Haemophilia, Sep. 2007, 13(5):663-669.

Uchida et al., "A first-in-human phase 1 study of ACE910, a novel factor VIII-mimetic bispecific antibody, in healthy subjects," Blood, Mar. 2016, 127(13):1633-1641. doi: 10.1182/blood-2015-06-650226, Epub Dec. 1, 2015.

Waaijer et al., "Preclinical PET imaging of bispecific antibody ERY974 targeting CD3 and glypican 3 reveals that tumor uptake correlates to T cell infiltrate" J Immunother Cancer, Mar. 2020, 8(1):e000548. doi: 10.1136/jitc-2020-000548.

Wenig al., "Structure of the streptococcal endopeptidase IdeS, a cysteine proteinase with strict specificity for IgG," Proc Natl Acad Sci USA, Dec. 14, 2004, 101:17371-17376.

Yu et al., "T cell-redirecting bispecific antibodies in cancer immunotherapy: recent advances," Jour Cancer Research and Clinical Oncology, Apr. 2019, 145:941-956.

Yu et al., "A novel targeted GPC3/CD3 bispecific antibody for the treatment hepatocellular carcinoma," Can Biol Ther, Jul. 2, 2020, 21(7):597-603. doi: 10.1080/15384047.2020.1743158. Epub Apr. 2, 2020; abstract.

U.S. Appl. No. 16/155,673, Igawa et al., filed Oct. 9, 2018.
U.S. Appl. No. 15/288,965, Igawa et al., filed Oct. 7, 2016.
U.S. Pat. No. 9,670,269, Igawa et al., dated Jun. 6, 2017.

Choi et al., "Crystal structures of immunoglobulin Fc heterodimers reveal the molecular basis for heterodimer formation," Mol Immunol, Jun. 2015, 65(2):377-83. doi: 10.1016/j.molimm.2015.2.017. Epub Mar. 2, 2015.

Feige et al., "How antibodies fold," Trends Biochem Sci, Apr. 2010, 35(4):189-98. doi: 10.1016/j.tibs.2009.11.005. Epub Dec. 21, 2009.

Goulet et al., "Kinetic mechanism of controlled Fab-arm exchange for the formation of bispecific immunoglobulin G1 antibodies," J Biol Chem, Jan. 12, 2018, 293(2):651-661. doi: 10.1074/jbc.RA117.000303, Epub Nov. 17, 2017.

Rispens et al., "Mechanism of Immunoglobulin G4 Fab-arm Exchange," J Am Chem Soc, Jul. 6, 2011, 133(26):10302-11. doi: 10.1021/ja203638y. Epub Jun. 15, 2011.

Labrijn et al., "Therapeutic IgG4 antibodies engage in Fab-arm exchange with endogenous human IgG4 in vivo" Nat Biotechnol, Aug. 2009, 27(8):767-771.

Lund et al., "Multiple interactions of IgG with its core oligosaccharide can modulate recognition by complement and human Fc gamma receptor I and influence the synthesis of its oligosaccharide chains," The Journal of Immunology, Dec. 1, 1996, 157(11):4963-4969.

Wu et al., "Humanization of a Murine Monoclonal Antibody by Simultaneous Optimization of Framework and CDR Residues," J Mol Biol, Nov. 19, 1999, 294(1):151-162.

Dall'Acqua et al., "Contribution of Domain Interface Residues to the Stability of Antibody $C_H3$ Domain Homodimers," Biochemistry, Jun. 30, 1998, 37(26):9266-9273. doi: 10.1021/bi980270i. PMID: 9649307.

Declaration of Christian Beil, signed Jun. 18, 2020, submitted by the opponent in Opposition of EP 3 050 963, 6 pages.

Helguera et al., "Antibody-Cytokine Fusion Proteins for the Therapy of Cancer," Methods Mol Med, 2005, 109:347-374. doi: 10.1385/1-59259-862-5:347. PMID: 15585931.

Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.

Otomo et al., "Structure of the heterodimeric complex between CAD domains of CAD and ICAD," Nat Struct Biol, Aug. 2000, 7(8):658-662, doi: 10.1038/77957. PMID: 10932250.

Raghavan et al., "Fc Receptors and Their Interactions with Immunoglobulins," Annu Rev Cell Dev Biol, Nov. 1996, 12:181-220.

Reference table: IMGT exon, EU and Kabat numbering of residues within the human IgG1 sequence; retrieved from http://www.imgt.org/IMGTScientificChart/Numbering/Hu_IGHGnber.html on Jun. 1, 2020, 4 pages (cited by the opponents in the Opposition procedure in the corresponding European Patent No. 3 050 963, which was notified to the patentee on Jul. 3, 2020).

USPTO Non-Final Office Action in U.S. Appl. No. 11/910,128, dated Nov. 28, 2016, 17 pages.

U.S. Appl. No. 14/680,250, Igawa et al., filed Apr. 7, 2015.
U.S. Appl. No. 13/497,269, Kuramochi et al., filed Jun. 1, 2012.
U.S. Appl. No. 14/921,590, Hattori et al., filed Oct. 23, 2015.
U.S. Appl. No. 15/172,727, Hattori et al., filed Jun. 3, 2016.

"National Haemophilia Foundation (NHF) Medical and Scientific Advisory Council (MASAC) Recommendations Concerning Prophylaxis," Medical Bulletin, No. 193, 1 page (1994).

Abe et al., "Novel Protein A Resin: Synthetic Polymer Matrix Design Impact on Antibody Binding Capacity," JSR Technical Review, No. 119, 2012, pp. 1-5 [online], retrieved on Feb. 17, 2017 (Feb. 17, 2017)], retrieved from Internet:<URL:http//www.jsr.co.jp/pdf/rdtec119-1.pdf> (with English translation).

Abe et al., "Purification of monoclonal antibodies with light-chain heterogeneity produced by mouse hybridomas raised with NS-1 myelomas: application of hydrophobic interaction high-performance liquid chromatography," J Biochem Biophys Methods, 27:215-227 (1993).

Abe et al., "Surrogate thrombopoietin," Immunology Letters, 61:73-78 (1998).

Adams et al., "Humanization of a recombinant monoclonal antibody to produce a therapeutic HER dimerization inhibitor, pertuzumab," Cancer Immunol, Immunother, 55:717-727 (2006).

Alarcon et al., "The CD3-γ and CD3-δ subunits of the T cell antigen receptor can be expressed within distinct functional TDR/CD3 complexes," EMBO J, Apr. 1991, 10(4):903-12.

Algonomics—Tripole® applications [online] [retrieved on Feb. 29, 2012], Retrieved from the Internet:http://web.archive.org/web20090221052902/http://www.algonomics.com/proteinengineering/tripole_applications.php, 2 pages (Feb. 21, 2009).

Allard et al., "Antigen binding properties of highly purified bispecific antibodies," Mol Immunol, Oct. 1992, 29(10):1219-27.

Allen et al., "Interchain disulfide bonding in human IgG2 antibodies probed by site-directed mutagenesis," Biochemistiy, 48(17):3755-66 (2009).

Almagro et al., "Humanization of antibodies," Front Biosci, 13:1619-33 (2008).

Amann et al., "Therapeutic window of an EpCAM/CD3-specific BiTE antibody in mice is determined by a subpopulation of EpCAM-expressing lymphocytes that is absent in humans," Cancer Immunol Immunother, Jan. 2009, 58(1):95-109, Epub Jul. 2, 2008.

Amersdorfer et al., GenPept Accession No. AAC26541, "anti BoNT/A Hc scFv antibody [synthetic construct]," 1 page (Aug. 1, 2001).

Amersham Biosciences, "Affinity Chromatography: Principles and Methods," Edition AD, 2002, pp. 16-18, 137.

Amersham Biosciences, "Protein Purification Handbook, " Edition AC, 2001, 98 pages.

Andris-Widhopf et al., "Methods for the generation of chicken monoclonal antibody fragments by phage display," Journal of Immunological Methods, 242:159-181 (2000).

Angal et al., "A single amino acid substitution abolishes the heterogeneity of chimeric mouse/human (IgG4) antibody," Mol Immunol, 30:105-108 (1993).

(56) References Cited

OTHER PUBLICATIONS

Armour et al., "Recombinant human IgG molecules lacking Fcgamma receptor I binding and monocyte triggering activities," Eur J Immunol, 29(8):2613-24 (1999).
Arndt et al., "Factors influencing the dimer to monomer transition of an antibody single-chain Fv fragment," Biochemistiy, 37(37)42918-26 (1998).
Arndt et al., "Generation of a highly stable, internalizing anti-DC22 single-chain Fv fragment for targeting non-Hodgkin's lymphoma," Int J Cancer, 107(5):822-829 (2003).
Arndt et al., "Helix-stabilized Fv (hsFv) antibody fragments: substituting the constant domains of a Fab fragment for a heterodimeric coiled-coil domain," J Mol Biol, 312:221-228 (2001).
Asano et al., Diabody-based Recombinant Formats of Humanized IgG-like Bispecific Antibody With Effective Retargeting of Lymphocytes to Tumor Cells, J Immunother, Oct. 2008, 31(8):752-61 (Abstract only).
Asano et al., "Highly effective recombinant format of a humanized IgG-like bispecific antibody for cancer immunotherapy with retargeting of lymphocytes to tumor cells," J Biol Chem, Sep. 21, 2007, 282(38):27659-65, Epub Jul. 19, 2007.
Aslan et al., "Engineering a novel, stable dimeric streptavidin with lower isoelectric point," J Biotechnol, 128(2):213-25 (2007).
Asselta et al., "Factor V Deficiency," Semin Thromb Hemost, Jun. 2009, 35:382-389.
Association of Hemophilia Clinic Directors of Canada, "Hemophilia and Von Willebrand's disease: 2. Management Association of Hemophilia Clinic Directors of Canada," Canadian Medical Association Journal, 153(2):147-157 (1995).
Atwell et al., "Stable heterodimers from remodeling the domain interface of a homodimer using a phage display library," J Mol Biol, 270:26-35 (1997).
Baerga-Ortiz et al., "Two different proteins that compete for binding to thrombin have opposite kinetic and thermodynamic profiles," Protein Sci, 13(1):166-76 (2004).
Bajaj et al., "A Monoclonal Antibody to Factor IX That Inhibits the Factor VIII:Ca Potentiation of Factor X Activation," J Biol Chem, Sep. 25, 1985, 260(21):11574-11580.
Baker et al., "Conversion of a T cell antagonist into an agonist by repairing a defect in the TCR/peptide/MHC interface: implications for TCR signaling," Immunity, 13:475-484 (2000).
Ballmaier et al., "c-mpl mutations are the cause of congenital amegakaryocytic thrombocytopenia," Blood, 97:139-146 (2001).
Bargou et al., "Tumor regression in cancer patients by very low doses of a T cell-engaging antibody," Science, 321(5891):974-7 (2008).
Bartelds et al., "Clinical response to adalimumab: relationship to anti-adalimumab antibodies and serum adalimumab concentrations in rheumatoid arthritis," Ann Rheum Dis, 66:921-926 (2007).
Batra et al., "Pharmacokinetics and biodistribution of genetically engineered antibodies," Curr Opin Biotechnol, Dec. 2002, 13(6):603-8.
Bayry et al., "Immuno affinity purification of foot and mouth disease virus type specific antibodies using recombinant protein adsorbed to polystyrene wells," J Virol Methods, 81:21-30 (1999).
Bebbington et al., "High-Level Expression of a Recombinant Antibody from Myeloma Cells Using a Glutamine Synthetase Gene as an Amplifiable Selectable Marker," Biotechnology (NY), Feb. 1992, 10:169-175.
Bender et al., "Immunogenicity, efficacy and adverse events of adalimumab in RA patients," Rheumatol Int, 27:269-274 (2007).
Bendig, "Humanization of Rodent Monoclonal Antibodies by CDR Grafting," Methods: A Companion to Methods in Enzymology, 8:83-93 (1995).
Bessos et al., "The characterization of a panel of monoclonal antibodies to human coagulation factor IX," Thrombosis Research, Dec. 15, 1985, 40:863-7.
Bian et al., "Discovery of promiscuous HLA-II-restricted T cell epitopes with TEPITOPE," Methods, Dec. 2004, 34(4):468-75.
Binz et al., "Engineering novel binding proteins from nonimmunoglobulin domains," Nat Biotechnol, 23:1257-68 (2005).
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J Immunol, 157:3250-59 (1996).
Bokemeyer, "Catumaxomab-trifunctional anti-EpCAM antibody used to treat malignant ascites," Expert Opin Biol Ther, 10(8):4259-69 (2010).
Bolton-Maggs et al., "Haemophilias A and B," The Lancet, May 24, 2003, 361:1801-9.
Borrebaeck et al., "Antibody evolution beyond Nature," Nat Biotechnol, Dec. 2002, 20(12):1189-90.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992, 11:41-51.
Bowen, Haemophilia A and haemophilia B: molecular insights, Mol Pathol, Feb. 2002, 55(1):1-18.
Bowie et al., "Deciphering the Message in Protein Sequences: Tolerance to Amino Acid Substitutions," Science, 247:1306-1310 (1990).
Branden and Tooze, "Recognition of Foreign Molecules by the Immune System," Introduction to Protein Structure, 2d Ed., Garland Publishing, 1999, pp. 299-323.
Brandstetter et al., "X-ray structure of clotting factor IXa: active site and module structure related to Xase activity and hemophilia B," Proc Natl Acad Sci USA, Oct. 10, 1995, 92(21):9796-800.
Brennan et al., "Preparation of Bispecific Antibodies by Chemical Recombination of Monoclonal Immunoglobulin G1 Fragments," Science, Jul. 5, 1985, 229:81-3.
Brenner et al., "Errors in genome annotation," Trends in Genetics, Apr. 1999, 15:132-133.
Brinkman et al. "Phospholipid-binding domain of factor VIII is involved in endothelial cell-mediated activation of factor X by factor IXa," Arterioscler Thromb Vase Biol, Mar. 1, 2002, 22(3):511-6.
Brinkmann et al., "FTY720: targeting G-protein-coupled receptors for sphingosine 1-phosphate in transplantation and autoimmunity," Curr Opin Immunol, 14:569-575 (2002).
Brown et al., "Tolerance of single, but not multiple, amino acid replacements in antibody $V_H$ CDR2: a means of minimizing B cell wastage from somatic hypermutation?," J Immunol, 156(9):3285-91 (1996).
Bruenke et al., "A recombinant bispecific single-chain Fv antibody against HLA class II and FcγRIII (CD 16) triggers effective lysis of lymphoma cells," Br J Haematol, 125:167-179 (2004).
Burges et al., "Effective relief of malignant ascites in patients with advanced ovarian cancer by a trifunctional anti-EpCAM x anti-CD3 antibody: a phase I/II study," Clin Cancer Res, 13(13):3899-905 (2007).
Burgess, "Possible dissociation of the heparin-binding and mitogenic activities of heparin-binding (acidic fibroblast) growth factor-1 from its receptor-binding activities by site-directed mutagenesis of a single lysine residue," J Cell Biol, 111:2129-2138 (1990).
CALBIOCHEM® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Campoli et al., "Immunotherapy of malignant disease with tumor antigen-specific monoclonal antibodies," Clin Cancer Res, Jan. 1, 2010, 16(1):11-20, Epub Dec. 22, 2009.
Canfield et al., "The Binding Affinity of Human IgG for its High Affinity Fc Receptor Is Determined by Multiple Amino Acids in the $C_H2$ Domain and Is Modulated by the Hinge Region," J Exp Med, Jun. 1, 1991, 173(6):1483-91.
Carter, "Bispecific human IgG by design," J. Immunol Methods, 248:7-15 (2001).
Casset et al., "A peptide mimetic of an anti-CD4 monoclonal antibody by rational design," Biochemical and Biophysical Research Communications, 307:198-205 (2003).

(56) References Cited

OTHER PUBLICATIONS

Cekaite et al., "Protein Arrays: A versatile toolbox for target identification and monitoring of patient immune responses," Methods Mol Biol, 360:335-348 (2007).
Chamow et al., "A humanized, bispecific immunoadhesin-antibody that retargets CD3+ effectors to kill HIV-1-infected cells," J Immunol, 153(9):4268-80 (1994).
Chappel et al., "Identification of a secondary Fc gamma RI binding site within a genetically engineered human IgG antibody," J Biol Chem, Nov. 25, 1993, 268(33):25124-31.
Chappel et al., "Identification of the Fc gamma receptor class I binding site in human IgG through the use of recombinant IgGl/IgG2 hybrid and point-mutated antibodies," Proc Natl Acad Sci USA, Oct. 1, 19915, 88(20):9036-40.
Chatellier et al., "Functional mapping of conserved residues located at the VL and VH domain interface of a Fab," J Mol Biol, 264(1):1-6 (1996).
Chau et al., "HuM291(Nuvion), a humanized Fc receptor-nonbinding antibody against CD3, anergizes peripheral blood T cells as partial agonist of the T cell receptor," Transplantation, 71(7):941-50 (2001).
Chen et al., "Defective secretion of an immunoglobulin caused by mutations in the heavy chain complementarity determining region 2," J Exp Med, 180(2):577-86 (1994).
Chen et al., "Generation and analysis of random point mutations in an antibody CDR2 sequence: many mutated antibodies lose their ability to bind antigen," J Exp Med, 176(3):855-66 (1992).
Chen et al., "Selection and analysis of an optimized anti-VEGF antibody: crystal structure of an affinity-matured Fab in complex with antigen," Journal of Molecular Biology, 293:865-881 (1999).
Chirino et al., "Minimizing the immunogenicity of protein therapeutics," Drug Discov Today, 9:82-90 (2004).
Choi et al., "Engineering of Immunoglobulin Fc Heterodimers Using Yeast Surface-Displayed Combinatorial Fc Library Screening," PLoS One, Dec. 16, 2015, 10(12):e0145349. doi: 10.1371/journal.pone.0145349, eCollection 2015.
Chowdhury et al., "Engineering scFvs for improved stability," Methods Mol Biol, 207:237-54 (2003).
Chu et al., "Accumulation of succinimide in a recombinant monoclonal antibody in mildly acidic buffers under elevated temperatures," Pharm Res, 24(6): 1145-56 (2007).
Chugai Seiyaku Kabushiki Kaisha's letter dated Jun. 12, 2013, regarding oral proceedings scheduled on Jun. 26, 2013, in App. Ser. No. EP 06 73 0769.4-1412.
Clackson et al., "Making antibody fragments using phage display libraries," Nature, 352:624-628 (1991).
Clark, "CD22, a B Cell-Specific Receptor, Mediates Adhesion and Signal Transduction," J Immunol, 150:4715-4718 (1993).
Co et al., "A Humanized Antibody Specific for the Platelet Integrin gpIIb/IIIa," J Immunol, 152:2968-2976 (1994).
Cochlovius et al., "Treatment of human B cell lymphoma xenografts with a CD3 x CD19 diabody and T cells," The Journal of Immunology, 2000, 165:888-895.
Cole et al., "Human IgG2 variants of chimeric anti-CD3 are nonmitogenic to T cells," J Immunol, 1997, 159(7):3613-21.
Coloma et al., "Position effects of variable region carbohydrate on the affinity and in vivo behavior of ananti-(1—>6) dextran antibody," J Immunol, Feb. 15, 1999, 162(4):2162-70.
Comper et al., "Charge selectivity in kidney ultrafiltration," Kidney Int, 1995, 47:1242-51.
Cordoba et al., "Non-enzymatic hinge region fragmentation of antibodies in solution," J. Chromatogr B Analyt Technol Biomed Life Sci, 2005, 818(2):115-21.
Couto et al., "Anti-BA46 Monoclonal Antibody Mc3: Humanization Using a Novel Positional Consensus and in Vivo and in Vitro Characterization," Cancer Research, 55:1717-1722 (1995).
Creighton, "Protein folding," Biochem. J., 270(1): 1-16 (1990).
Cruse et al., Atlas of Immunology, CRC Press LLC, 2004, excerpt from Chapter 3, "Antigens and Immunogens", p. 109.
Dahlback, "Blood coagulation," Lancet, 355(9215):4627-32 (2000).

Dall'Acqua et al., "Antibody humanization by framework shuffling," Methods, 36(1):43-60 (2005).
Dall'Acqua et al., "Increasing the affinity of a human IgG1 for the neonatal Fc receptor: biological consequences," J. Immunol., Nov. 1, 2002, 169(9):5171-80.
Dall'Acqua et al., "Modulation of the effector functions of a human IgG1 through engineering of its hinge region," J. Immunol., 177(2):1129-38 (2006).
Dall'Acqua et al., "Properties of human IgG1s engineered for enhanced binding to the neonatal Fc receptor (FcRn)," J. Biol. Chem., Aug. 18, 2006, 281(33):23514-24, Epub Jun. 21, 2006.
Damschroder et al., "Framework shuffling of antibodies to reduce immunogenicity and manipulate functional and biophysical properties," Mol. Immunol., 44(11):3049-60 (2007).
Daniel et al., "Induction of Apoptosis in Human Lymphocytes by Human Anti-HLA Class I Antibodies," Transplantation, 75:1380-1386 (2003).
Datta-Mannan et al., "Monoclonal antibody clearance. Impact of modulating the interaction of IgG with the neonatal Fc receptor," J Biol Chem., 282(3):4709-17 (2007).
Davie et al., "The coagulation cascade: Initiation, maintenance, and regulation," Biochemistry, Oct. 29, 1991, 30(43):10363-70.
Davies et al., "Antibody VH domains as small recognition units," Biotechnology (N.Y.), 13(5):475-9 (1995).
Decision of the Opposition Division for EP 2 006 381 on Jul. 25, 2018, 17 pages.
De Felice et al., "Differential regulatory role of monomorphic and polymorphic determinants of histocompatibility leukocyte antigen class I antigens in monoclonal antibody OKT3-induced T cell proliferation," J. Immunol., 139:2683-2689 (1987).
De Gast et al., "CD8 T cell activation after intravenous administration of CD3 x CD19 bispecific antibody in patients with non-Hodgkin lymphoma," Cancer Immunol Immunother, Jun. 1995, 40(6):390-6.
De Groot et al., "De-immunization of therapeutic proteins by T-cell epitope modification," Dev. Biol. (Basel), 122:171-94 (2005).
De Jonge et al., "Production and Characterization of Bispecific Single-Chain Antibody Fragments," Mol. Immunol., 32:1405-1412 (1995).
De Pascalis et al., "Grafting of 'abbreviated' complementary-determining regions containing specificity-determining residues essential for ligand contact to engineer a less immunogenic humanized monoclonal antibody," Journal of Immunology, Sep. 15, 2002, 169(6):3076-3084.
Deen et al., "Structural determinants of glomerular permeability," Am. J. Physiol. Renal. Physiol., 281:F579-F596 (2001).
De Jonge et al., "In vivo retargeting of T cell effector function by recombinant bispecific single chain Fv (anti-DC3 x anti-idiottype) induces long term survival of the murine BCL1 lymphoma model," J. Immunol., 161(3):1454-1461 (1998).
Del Rio et al., "An Engineered Penicillin Acylase with Altered Surface Charge Is More Stable in Alkaline pH," Ann. NY Acad. Sci., 799:61-64 (1996).
Denardo et al., "Anti-HLA-DR/anti-DOTA Diabody Construction in a Modular Gene Design Platform: Bispecific Antibodies for Pretargeted Radioimmunotherapy," Cancer Biother. Radiopharm,, 16:525-535 (2001).
Deng et al., "An Agonist Murine Monoclonal Antibody to the Human c-Mpl Receptor Stimulates Megakaryocytopoiesis," Blood, 92:1981-1988 (1998).
Desplancq et al., "Multimerization behaviour of single chain Fv variants for the tumour-binding antibody B72.3," Protein Engineering, 7(8): 1027-1033 (1994).
Dhiman et al., "Gene expression microarrays: a 21st century tool for directed vaccine design," Vaccine, Oct. 12, 2001, 20(1-2):22-30.
Diaz et al., "Effects of engineering charged amino acids in the CH3 domains on antibody heavy chain dimerization," Philippine Science Letters, 2011, 4(1):48-55.
Dillon et al., "Structural and functional characterization of disulfide isoforms of the human IgG2 subclass," J. Biol. Chem., 283(23):16206-15 (2008).

(56) References Cited

OTHER PUBLICATIONS

Dufner et al., "Harnessing phage and ribosome display for antibody optimization," Trends Biotechnol., Nov. 2006, 24(11):523-9. Epub Sep. 26, 2006.
Dumont et al., "Monomeric Fc fusions: impact on pharmacokinetic and biological activity of protein therapeutics," BioDrugs., May 1, 2006, 20(3):151-60.
Ebert et al., "Expression of Metallothionein II in Intestinal Metaplasia, Dysplasia, and Gastric Cancer," Cancer Res., 60:1995-2001 (2000).
Eijsink et al., "Rational engineering of enzyme stability," Journal of Biotechnology, 113:105-120 (2004).
Ejima et al, "Effects of Acid Exposure on the Conformation, Stability, and Aggregation of Monoclonal Antibodies," Proteins, Mar. 1, 2007, 66(4):954-62.
Elliott et al., "Activation of the Erythropoietin (EPO) Receptor by Bivalent Anti-EPO Receptor Antibodies," J. Biol. Chem., 271:24691-24697 (1996).
EPO Register Extract EP 1915397 (document submitted in EP opposition and posted by EPO on Feb. 2, 2018); 4 pages.
Ewert et al., "Biophysical properties of human antibody variable domains," J. Mol. Biol., 325:531-553 (2003).
Ewert et al., "Stability improvement of antibodies for extracellular and intracellular applications: CDR grafting to stable frameworks and structure-based framework engineering," Methods, 34:184-199 (2004).
Ewert et al., "Structure-based improvement of the biophysical properties of immunoglobulin $V_H$ domains with a generalizable approach," Biochemistiy, 42:1517-1528 (2003).
Fay et al., "Chapter 2B Nonenzymatic cofactors: factor VIII," Comprehensive Biochemistry, 13:35-37 (1986).
Fay et al., "The size of human factor VIII heterodimers and the effects produced by thrombin," Biochim Biophys Acta., 871(3):268-78 (1986).
Fay, "Activation of factor VIII and mechamsms of cofactor action," Blood Rev., Mar. 2004, 18(1):1-15.
Fayen et al., "Negative signaling by anti-HLA class I antibodies is dependent upon two triggering events," Int. Immunol., 10:1347-1358 (1998).
Figini et al., "In vitro assembly of repertoires of antibody chains on the surface of phage by renaturation," J Mol Biol., May 27, 1994, 239(1):68-78.
Francois et al., "Construction of a Bispecific Antibody Reacting with the +- and β-Chains of the Human IL-2 Receptor," J. Immunol., May 15, 1995, 150:4610-9.
Fujii, "Antibody affinity maturation by random mutagenesis," Methods Mol. Biol., 248:345-59 (2004).
Funaro et al., "Monoclonal antibodies and therapy of human cancers," Biotechnol. Adv., 18:385-401 (2000).
GE Healthcare Life Sciences, Dynamic binding capacity study on MabSelect SuReTM LX for capturing high-titer monoclonal antibodies, Application note 28-9875-25-AA, 2011, [online], (retrieved on Feb. 17, 2017], retrieved from the internet:<URL:http://www.processdevelopmentforum.com/images/articles/28-9875-25_AA_AN_DBC_study_on_MabSelect_SuRe_LX_final.pdf.
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., 82(4):483-93 (2002).
Geneseq Accession No. AEM45140, Feb. 22, 2007, "Light chain constant region of therapeutic human IgG antibody".
Geneseq Accession No. ARZ17615, Aug. 21, 2008, "Human antibody IgG2 heavy chain constant region SEQ ID No. 36".
Gen Bank Accession No. AAG00910.2, "recombinant IgG2 heavy chain, partial [*Homo sapiens*]," May 14, 2001, 1 page.
Genestier et al., "Caspase-dependent Ceramide Production in Fas- and HLA Class I-mediated Peripheral T Cell Apoptosis," J. Biol. Chem., 273:5060-5066 (1998).
Genestier et al., "Antibodies to HLA Class 1 α1 Domain Trigger Apoptosis of CD40-Activated Human B Lymphocytes," Blood, 90:726-735 (1997).

Genestier et al., "Fas-Independent Apoptosis of Activated T Cells Induced by Antibodies to the HLA Class I α1 Domain," Blood, 90:3629-3639 (1997).
Genestier et al., "T cell sensitivity to HLA class I-mediated apoptosis is dependent on interleukin-2 and interleukin-4," Eur. J. Immunol., 27:495-499 (1997).
Gerstner et al., "Sequence plasticity in the antigen-binding site of a therapeutic anti-HER2 antibody," J. Mol, Biol., 321(5):851-62 (2002).
Gessner et al., "The IgG Fc receptor family," Ann. Hematol., 76:231-248 (1998).
Ghetie et al., "FcRn: the MHC class I-related receptor that is more than an IgG transporter," Immunol. Today, 18:592-598 (1997).
Ghetie et al., "Homodimerization of tumor-reactive monoclonal antibodies markedly increases their ability to induce growth arrest or apoptosis of tumor cells," Proc. Natl. Acad. Sci. USA, 94:7509-7514 (1997).
Ghetie et al., "Increasing the serum persistence of an IgG fragment by random mutagenesis," Nature Biotechnology, 15:637-640 (1997).
Ghetie et al., "Multiple roles for the major histocompatibility complex class I-related receptor FcRn," Annu. Rev. Immunol., 18:739-766 (2000).
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Goding, "Monoclonal Antibodies: Principles and Practice," Academic Press, second Ed., 125:129 (1986).
Goel et al., "$^{99m}$Tc-Labeled Divalent and Tetravalent CC49 Single-Chain Fv's: Novel Imaging Agents for Rapid In Vivo Localization of Human Colon Carcinoma," J. Nucl. Med., 42:1519-1527 (2001).
Goel et al., "Genetically Engineered Tetravalent Single-Chain Fv of the Pancarcinoma Monoclonal Antibody CC49: Improved Biodistribution and Potential for Therapeutic Application," Cancer Res., 60:6964-6971 (2000).
Golay et al., "Mechanism of action of therapeutic monoclonal antibodies: Promises and pitfalls of in vitro and in vivo assays" Archives of Biochemistry and Biophysics, Feb. 25, 2012, 526:146-153.
Goldstein et al., "Cytolytic and Cytostatic Properties of an Anti-Human FcγRI (CD64) x Epidermal Growth Factor Bispecific Fusion Protein," J. Immunol., 158:872-879 (1997).
Gonzales et al., "Minimizing the immunogenicity of antibodies for clinical application," Tumour Biol., Jan.-Feb. 2005, 26(1):31-43.
Goode et al., "The glomerular basement membrane charge-selectivity barrier: an oversimplified concept?," Nephrol. Dial. Transplant., 11:1714-16 (1996).
Goto et al., "A Novel Membrane Antigen Selectively Expressed on Terminally Differentiated Human B Cells," Blood, 84:1922-1930 (1994).
Gramer et al., "Production of stable bispecific IgG1 by controlled Fab-arm exchange: scalability from bench to large-scale manufacturing by application of standard approaches," mAbs., Nov.-Dec. 2013, 5(6):962-73, doi: 10,4161/mabs.26233. Epub Aug. 22, 2013.
Graves et al., "Molecular modeling and preclinical evaluation of the humanized NR-LU-13 antibody," Clin. Cancer Res., 5:899-908 (1999).
Greenwood et al., "Structural motifs involved in human IgG antibody effector functions," Eur J Immunol., May 1993, 23(5):1098-104.
Griffin et al., "Analysis of heavy and light chain sequences of conventional camelid antibodies from *Camelus dromedarius* and *Camelus bactrianus* species," J Immunol Methods, Mar. 2014, 405:35-46, doi: 10.1016/j.jim.2014.01.003, Epub Jan. 18, 2014.
Grosse-Hovest et al., "A recombinant bispecific single-chain antibody induces targeted, supra-agonistic CD28-stimulation and tumor cell killing", European Journal of Immunology, May 2003, 33(5):1334-40.
Gruber et al., "Efficient tumor cell lysis mediated by a bispecific single chain antibody expressed in *Escherichia coli*," Journal of Immunology, 152:5368-5374 (1994).

(56) References Cited

OTHER PUBLICATIONS

Gunasekaran et al., "Enhancing antibody Fc heterodimer formation through electrostatic steering effects: applications to bispecific molecules and monovalent IgG," J. Biol. Chem., 285(25):19637-46 (2010).
Gunawardane et al., "Agonistic Human Antibodies Binding to Lecithin-Cholesterol Acyltransferase Modulate High Density Lipoprotein Metabolism," J Biol Chem, Feb. 5, 2016, 291(6):2799- 811, doi: 10. 1074/j bc. Ml 15.672790. Epub Dec. 7, 2015.
Gupta et al., "Affinity chromatography and co-chromatography of bispecific monoclonal antibody immunoconjugates," J. Biochem. Biophys. Methods, 51:203-216 (2002).
Guyre et al., "Increased potency of Fc-receptor-targeted antigens," Cancer Immunol. Immunother., 45(3-4):146-8 (1997).
Haagen et al., "Unprimed CD4+ and CD8+ T cells can be rapidly activated by a CD3 x CD19 bispecific antibody to proliferate and become cytotoxic," Cancer Immunol Immunother., Dec. 1994, 39(6):391-6.
Hamers-Casterman et al., "Naturally occurring antibodies devoid of light chains," Nature, Jun. 3, 1993, 363(6428):446-8.
Hämmerling et al., "Use of Hybrid Antibody with Anti-γG and Anti-Ferritin Specificities in Locating Cell Surface Antigens by Electron Microscopy," J. Exp. Med., Dec. 1, 1968, 128:1461-73.
Hanson et al., "Catalytic antibodies and their applications," Curr. Opin. Biotechnol., 16:631-636 (2005).
Hattori, "Introduction of ART-Ig and application to hemophilia A treatment," Chugai Seiyaku ni Okeru Dokuji no Kakushinteki Kotai Gijutsu. Dec. 2012; 18:42-57 (with English translation).
He et al., "Humanization and pharmacokinetics of a monoclonal antibody with specificity for both E- and P-selectin," J. Immunol., 160:1029-35 (1998).
Helfrich et al., "A rapid and versatile method for harnessing scFv antibody fragments with various biological effector functions," J. Immunol. Methods, 237(1-2):131-45 (2000).
Hinton et al., "An engineered human IgG1 antibody with longer serum half-life," J. Immunol., Jan. 1, 2006, 176:346-56.
Hinton et al., "Engineered human IgG antibodies with longer serum half-lives in primates," J Biol Chem., Feb. 20, 2004, 279(8):6213-6. Epub Dec. 29, 2003.
Hird et al., "Tumour localisation with a radioactively labelled reshaped human monoclonal antibody," Br J Cancer, Nov. 1991, 64(5):911-4.
Hoad et al. "Characterization of monoclonal antibodies to human factor X.Xa: Initial observations with a quantitative ELISA procedure," J. Immunol. Methods, Feb. 15, 1991, 136(2):269-78.
Holliger et al., "'Diabodies': Small bivalent and bispecific antibody fragments," Proc. Natl. Acad. Sci. USA, 90:6444-6448 (1993).
Hombach et al., "A CD16/CD30 bispecific monoclonal antibody induces lysis of Hodgkin's cells by unstimulated natural killer cells in vitro and in vivo," Int J Cancer, 55:830-6 (1993).
Hong et al., "Enhanced cellular uptake and transport of polyclonal immunoglobulin G and fab after their cationization," J Drug Target., 2000, 8(2):67-77.
Hoogenboom et al., "Multi-subunit proteins on the surface of filamentous phage: methodologies for displaying antibody (Fab) heavy and light chains," Nucleic Acids Res., 19:4133-4137 (1991).
Hotzel et al., "A strategy for risk mitigation of antibodies with fast clearance," mAbs, Nov./Dec. 2012, 4(6):753-60. doi: 10.4161/mabs. 22189.
Hoyer, L.W., "The factor VIII complex: structure and function," Blood, 58(1):1-13 (1981).
Hozumi et al., "Evidence for somatic rearrangement of immunoglobulin genes coding for variable and constant regions," Proc. Natl. Acad. Sci. USA, 73(10):3628-3632 (1976).
Hsia et al., "Treatment of acquired factor X inhibitor by plasma exchange with concomitant intravenous immunoglobulin and corticosteroids," Am. J. Hematol., Apr. 2008, 83, 318-20.
Hu et al., "Development and characterization of a novel fusion protein composed of a human IgG1 heavy chain constant region and a single-chain fragment variable antibody against Venezuelan equine encephalitis virus," J Biochem., 133(1):59-66 (2003).
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," Cancer Res., 56:3055-3061 (1996).
Hudson et al., "High avidity scFv multimers; diabodies and triabodies," J. Immunol. Methods, 231:177-189 (1999).
Huse et al., "Generation of a Large Combinatorial Library of the Immunoglobulin Repertoire in Phage Lambda," Science, Dec. 8, 1989, 246:1275-81.
Hwang et al., "Use of human germline genes in a CDR homology-based approach to antibody humanization," Methods, 36:35-42 (2005).
Igawa et al., "Antibody recycling by engineered pH-dependent antigen binding improves the duration of antigen neutralization," Nat. Biotechnol., 28(11):1203-7 (2010).
Igawa et al., "Engineering the variable region of therapeutic IgG antibodies," mAbs, 3(3):243-52 (2011).
Igawa et al., "Reduced elimination of IgG antibodies by engineering the variable region," Protein Eng. Des. Sel., 23(5):385-92 (2010).
Igawa et al., "VH/VL interface engineering to promote selective expression and inhibit conformational isomerization of thrombopoietin receptor agonist single-chain diabody," Protein Eng Des Sel., Aug. 2010, 23(8):667-77, doi: 10.1093/protein/gzq034. Epub Jun. 24, 2010.
IMGT Scientific charts depicting the correspondence between Eu and Kabat numberings for the human IgG constant region, created May 17, 2001 and last updated Aug. 13, 2014.
Ito et al., "The His-probe method: effects of histidine residues introduced into the complementarity-determining regions of antibodies on antigen-antibody interactions at different pH values," FEBS Lett., 309:85-88 (1992).
Iwahashi et al., "CDR substitutions of a humanized monoclonal antibody (CC49): contributions of individual CDRs to antigen binding and immunogenicity," Mol Immunol., Oct.-Nov. 1999, 36(15-16):1079-91.
Jackman et al., "Development of a two-part strategy to identify a therapeutic human bispecific antibody that inhibits IgE receptor signaling," J Biol Chem., Jul. 2, 2010, 285(27): 20850-9. doi: 10.1074/jbc.M110.113910. Epub May 5, 2010.
Jäger et al., "Folding and assembly of an antibody Fv fragment, a heterodimer stabilized by antigen," Journal of Molecular Biology, 285:2005-2019 (1999).
Jain et al., "Engineering antibodies for clinical applications," Trends Biotechnol., 25(7):307-16 (2007).
Janeway et al., "Structure of the Antibody Molecule and Immunoglobulin Genes," Immunobiology, 3rd Edition, Garland Press, 3:1-3:11 (1997).
Janeway et al., Immunobiology, 5th edition. 2001 Extract from Chapter 3, pp. 93-122.
Janeway et al., Immunobiology, 5th edition. 2001 Extract from Chapter 4, pp. 123-154.
Jefferis et al., "Recognition sites on human IgG for Fc gamma receptors: the role of glycosylation," Immunol. Lett., 44(2-3):111-7 (1995).
Jendeberg et al., "Engineering of Fc(1) and Fc(3) from human immunoglobulin G to analyse subclass specificity for staphylococcal protein A," J. Immunol. Methods., 201(1):25-34 (1997).
Jirholt et al., "Exploiting sequence space: shuffling in vivo formed complementarity determining regions into a master framework," Gene., Jul. 30, 1998, 215(2):471-6.
Johnson et al., "Cation exchange-HPLC and mass spectrometry reveal C-terminal amidation of an IgG1 heavy chain," Anal. Biochem., 360:75-83 (2007).
Johnson et al., "Kabat database and its applications: 30 years after the first variability plot," Nucleic Acids Res., Jan. 1, 2000, 28(1):214-8.
Jones et al., "Identification and removal of a promiscuous CD4+ T cell epitope from the C1 domain of factor VIII," Thromb. Haemost., 3:991-1000 (2005).

(56) References Cited

OTHER PUBLICATIONS

Ju et al., "Conversion of the interleukin 1 receptor antagonist into an agonist by site-specific mutagenesis," Proc. Natl. Acad. Sci. USA, 88:2658-2662 (1991).

Jung et al., "The importance of framework residues H6, H7 and H10 in antibody heavy chains: experimental evidence for a new structural subclassification of antibody V(H) domains," J. Mol. Biol., 309(3):701-16 (2001).

Kabat et al., Sequence of Proteins of Immunological Interest, 5$^{th}$ Edition 1991, p. 690 and p. 693.

Kabat, et al., National Institute of Health, Publ'n No. 91-3242, Sequences of Proteins of Immunological Interest, vol. 1, p. 647-60 (5th ed. 1991).

Kabsch et al., "On the use of sequence homologies to predict protein structure: identical pentapeptides can have completely different conformations," Proc Natl Acad Sci USA, Feb. 1984, 81(4):1075-8.

Kai et al., "Switching constant domains enhances agonist activities of antibodies to a thrombopoietin receptor," Nat. Biotechnol., 26(2):209-11 (2008).

Kang et al., "Linkage of recognition and replication functions by assembling combinatorial antibody Fab libraries along phage surfaces," Proc. Natl. Acad. Sci. USA, May 15, 1991, 88:4363-6.

Karpovsky et al., "Production of Target-Specific Effector Cells Using Hetero-Cross-Linked Aggregates Containing Anti-Target Cell and Anti-Fcγ Receptor Antibodies," J. Exp. Med., Dec. 1, 1984, 160:1686-701.

Kashmiri et al., "Generation, characterization, and in vivo studies of humanized anticarcinoma antibody CC49," Hybridoma, 14:461-473 (1995).

Katayose et al., "MUC1-specific targeting immunotherapy with bispecific antibodies: inhibition of xenografted human bile duct carcinoma growth," Cancer Res., 56(18):4205-12 (1996).

Kenanova et al., "Tailoring the pharmacokinetics and positron emission tomography imaging properties of anti-carcinoembryonic antigen single-chain Fv-Fc antibody fragments," Cancer Res., Jan. 15, 2005, 65(2):622-31.

Kerschbaumer et al., "An antibody specific for coagulation factor IX enhances the activity of the intrinsic factor X-activating complex," J. Biol. Chem., 279(39):40445-50 (2004).

Khalifa et al., "Effects on interaction kinetics of mutations at the VH-VL interface of Fabs depend on the structural context," J. Mol. Recognit., 13(3):127-39 (2000).

Khawli et al., "Improved tumor localization and radioimaging with chemically modified monoclonal antibodies," Cancer Biother. Radiopharm., 11:203-215 (1996).

Kikuchi et al., "A bivalent single-chain Fv fragment against CD47 induces apoptosis for leukemic cells," Biochem. Biophys. Res. Commun., 315:912-918 (2004).

Kim et al., "Antibody Engineering for the Development of Therapeutic Antibodies," Mol. Cells, 20:17-29 (2005).

Kim et al., "Chemical modification to reduce renal uptake of disulfide-bonded variable region fragment of anti-tac monoclonal antibody labeled with 99mTc," Bioconjugate Chem., 10:447-453 (1999).

Kim et al., "Lowering of pI by acylation improves the renal uptake of 99mTc-labeled anti-Tac dsFv: effect of different acylating reagents," Nucl. Med. Biol., 29:795-801 (2002).

Kim et al., "Mammalian type I interferon receptors consists of two subunits: IFNaR1 and IFNaR2," Gene, Sep. 1, 1997, 196:279-86.

Kim et al., "Mapping the site on human IgG for binding of the MHC class I-related receptor, FcRn," Eur. J. Immunol,, Sep. 1999, 29(9):2819-25.

Kimura et al., "2D7 diabody bound to the α2 domain of HLA class I efficiently induces caspase-independent cell death against malignant and activated lymphoid cells," Biochem. Biophys. Res. Commun., 325:1201-1209 (2004).

Kipriyanov et al., "Generation of Recombinant Antibodies," Molecular Biotechnology, 12:173-201 (1999).

Kipriyanov et al., "Bispecific CD3 x CD19 diabody for T cell-mediated lysis of malignant human B cells," In. J. Cancer, 77:763-772 (1998).

Kipriyanov et al., "Bispecific tandem diabody for tumor therapy with improved antigen binding and pharmacokinetics," Journal of Molecular Biology, 293:41-56 (1999).

Kipriyanov et al., "Effect of Domain Order on the Activity of Bacterially Produced Bispecific Single-chain Fv Antibodies," J. Mol. Biol., 330:99-111 (2003).

Kitazawa et al., "A bispecific antibody to factors IXa and X restores factor VIII hemostatic activity in a hemophilia A model," Nat Med, Oct. 2012, 18(10):1570-4. doi: 10.1038/nm.2942. Epub Sep. 30, 2012.

Klein et al., "Progress in overcoming the chain association issue in bispecific heterodimeric IgG antibodies," mAbs., Nov.-Dec. 2012, 4(6):653-63, doi: 10.4161/mabs.21379. Epub Aug. 27, 2012.

Kobayashi et al., "A monoclonal antibody specific for a distinct region of hen egg-white lysozyme," Mol. Immunol., 19:619-30 (1982).

Kobayashi et al., "The pharmacokinetic characteristics of glycolated humanized anti-Tac Fabs are determined by their isoelectric points," Cancer Res., 59:422-430 (1999).

Komissarov et al., "Site-specific mutagenesis of a recombinant anti-single-stranded DNA Fab. Role of heavy chain complementarity-determining region 3 residues in antigen interaction," J. Biol. Chem., 272(43):26864-70 (1997).

Kong et al., "A Single Residue, Aspartic Acid 95, in the δ Opioid Receptor Specifies Selective High Affinity Agonist Binding," The Journal of Biological Chemistry, 268(31):23056-23058 (1993).

Kontermann, R., "Recombinant bispecific antibodies for cancer therapy," Acta Pharmacol. Sin., 26(1):1-9 (2005).

Korn et al., "Recombinant bispecific antibodies for the targeting of adenoviruses to CEA-expressing tumour cells: a comparative analysis of bacterially expressed single-chain diabody and tandem scFv," The Journal of Gene Medicine, 6:642-651 (2004).

Kortt et al., "Dimeric and trimeric antibodies: high avidity scFvs for cancer targeting," Biomol. Eng., 18:95-108 (2001).

Kranenborg et al., "Development and characterization of anti-renal cell carcinoma x antichelate bispecific monoclonal antibodies for two-phase targeting of renal cell carcinoma," Cancer Res., 55:5864s-5867s (1995).

Krebber et al., "Reliable cloning of functional antibody variable domains from hybridomas and spleen cell repertoires employing a reengineered phage display system," J. Immunol. Methods, 201:35-55 (1997).

Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," Clin. Cancer Res., 6:1476-1487 (2000).

Kreutz et al., "Efficient bispecific monoclonal antibody purification using gradient thiophilic affinity chromatography," J. Chromatogr. B, 714:161-170 (1998).

Kriangkum et al., "Bispecific and bifunctional single chain recombinant antibodies," Biomol. Eng., 18(2):31-40 (2001).

Kroesen et al., "Phase I study of intravenously applied bispecific antibody in renal cell cancer patients receiving subcutaneous interleukin 2," Br. J. Cancer, Oct. 1994, 70:652-61.

Kufer et al., "A revival of bispecific antibodies," Trends Biotechnol., 22(5):238-44 (2004).

Kulkarni et al., "Construction of a Single-Chain Antibody Derived From 5H7, A Monoclonal Antibody Specific for a Death Signaling Domain of Human Class I Major Histocompatibility Complex," Transplant. Proc., 30:1081 (1998).

Kulkarni et al., "Programmed Cell Death Signaling Via Cell-Surface Expression of a Single-Chain Antibody Transgene," Transplantation, 69:1209-1217 (2000).

Kumagai et al., "Humanized bispecific antibodies that recognize lymphocytes and cancer cells," Drug Delivery System, 23(5):518-25 (2008) (with English translation).

Kumar et al., "Molecular cloning and expression of the Fabs of human autoantibodies in *Escherichia coli*. Determination of the

(56) References Cited

OTHER PUBLICATIONS heavy or light chain contribution to the anti-DNA/-cardiolipin activity of the Fab," J Biol Chem., Nov. 10, 2000, 275(45):35129-36.
Kumar et al., "The second PDZ domain of INAD is a type I domain involved in binding to eye protein kinase C. Mutational analysis and naturally occurring variants," J. Biol. Chem., 276(27):24971-24977 (2001).
Kurfis et al., "Role of Arg182 in the second extracellular loop of angiotensin II receptor AT2 in ligand binding," Biochem. Biophys. Res. Commun., 263:816-819 (1999).
Kurokawa et al., "Enhanced Fibrinolysis by a Bispecific Monoclonal Antibody Reactive to Fibrin and Tissue Plasminogen Activator," Bio/Technology, Nov. 1989, 7:1163-7.
Kurucz et al., "Retargeting of CTL by an efficiently refolded bispecific single-chain Fv dimer produced in bacteria," The Journal of Immunology, 154:4576-4582 (1995).
Labrijn et al., "Controlled Fab-arm exchange for the generation of stable bispecific IgG1," Nat Protoc. Oct. 2014, 9(10): 2450-63. doi: 10.1038/nprot.2014.169. Epub Sep. 25, 2014.
Labrijn et al., "Efficient generation of stable bispecific IgG1 by controlled Fab-arm exchange," Pro Natl Acad Sci USA, Mar. 26, 2013, 110(13):5145-50. doi: 10.1073/pnas.1220145110. Epub Mar. 11, 2013.
Labrijn et al., "Species-specific determinants in the IgG CH3 domain enable Fab-arm exchange by affecting the noncovalent CH3-CH3 interaction strength," J Immunol., Sep. 15, 2011, 187(6):3238-46. doi: 10.4049/jimmunol.1003336. Epub Aug. 12, 2011.
Lacroix-Desmazes et al., "Dynamics of factor VIII interactions determine its immunologic fate in hemophilia A," Blood, Jul. 15, 2008, 112(2):240-9. doi: 10.1182/blood-2008-02-124941. Epub May 9, 2008.
Lansdorp et al., "Purification and analysis of bispecific tetrameric antibody complexes," Mol. Immunol., 27:659-666 (1990).
Lapan et al., "Interaction of the A1 Subunit of Factor VIIIa and the Serine Protease Domain of Factor X Identified by Zero-length Cross-linking," Thromb. Haemost., Sep. 1998, 80:418-22.
Lazar et al., "Transforming growth factor alpha: mutation of aspartic acid 47 and leucine 48 results in different biological activities," Mol. Cell Biol., 8:1247-1252 (1988).
Lazar et al., Engineered antibody Fc variants with enhanced effector function, Proc Natl Acad Sci USA, Mar. 14, 2006, 103(11):4005-10, Epub Mar. 6, 2006.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J. Nucl. Med., Oct. 1993, 34:1662-71.
Le Gall et al., "Effect of linker sequences between the antibody variable domains on the formation, stability and biological activity of a bispecific tandem diabody," Protein Engineering Design & Selection, 17(4):357-366 (2004).
Lebégue et al., "Production and characterization of hybrid monoclonal antibodies with IgG1/IgG3 double isotype," C R Acad Sci III., 1990, 310(9):377-82.
Lebrun et al., "Antibodies to the Extracellular Receptor Domain Restore the Hormone-insensitive Kinase and Conformation of the Mutant Insulin Receptor Valine 382," J. Biol. Chem., 268:11272-11277 (1993).
Ledbetter et al., "Agonistic Activity of a CD40-Specific Single-Chain Fv Constructed from the Variable Regions of mAb G28-5," Critical Reviews in Immunology, 17:427-435 (1997).
Lenting et al., "The life cycle of coagulation factor VIII in view of its structure and function", Blood, Dec. 1, 1998, 92(11):3983-96.
Leong et al., "Adapting pharmacokinetic properties of a humanized anti-interleukin-8 antibody for therapeutic applications using site-specific pegylation," Cytokine, 16(3):106-19 (2001).
Li et al., "Construction and characterization of a humanized anti-human CD3 monoclonal antibody 12F6 with effective immunoregulation functions," Immunology, Dec. 2005, 116(4):487-98.

Li et al., "The Epitope Specificity and Tissue Reactivity of Four Murine Monoclonal Anti-CD22 Antibodies," Cell. Immunol., 118:85-99 (1989).
Life Technologies (Invitrogen: "ecdysone analogue" andpIND plasmid), Aug. 10, 2012, 2 pages.
Lin et al., "Preclinical pharmacokinetics, interspecies scaling, and tissue distribution of a humanized monoclonal antibody against vascular endothelial growth factor," J Pharmacol Exp Ther., 288(1):371-8 (1999).
Lindhofer et al., "Preferential Species-Restricted Heavy/Light Chain Pairing in Rat/Mouse Quadromas," J. Immunol., 155:219-225 (1995).
Lindsay, "Chapter 4: Determination of the Kinetics and Mechamsm of tg-FIX Activation by Factor XIa," 49-75 (2004).
Link et al., "Production and Characterization of a Bispecific IgG Capable of Inducing T-Cell-Mediated Lysis of Malignant B Cells," Blood, Jun. 15, 1993, 81:3343-9.
Little et al., "Of mice and men: hybridoma and recombinant antibodies," Immunol. Today, 21:364-370 (2000).
Liu et al., "Functional interactions between arginine-133 and aspartate-88 in the human reduced folate carrier: evidence for a charge-pair association," Biochem. J., 358:511-516 (2001).
Liu et al., "Heterogeneity of monoclonal antibodies," J. Pharm. Sci., 97(7):2426-47 (2008).
Lloyd et al., "The production of a bispecific anti-CEA, anti-hapten (4-amino-phthalate) hybrid-hybridoma," J Natl Med Assoc., Oct. 1991, 83(10):901-4.
Lobo et al., "Antibody pharmacokinetics and pharmacodynamics," J. Pharm. Sci., 93:2645-68 (2004).
Löfqvist et al., "Haemophilia prophylaxis in young patients—a long-term follow-up," J. Intern. Med., May 1997, 241:395-400.
Lu et al., "Di-diabody: a novel tetravalent bispecific antibody molecule by design," J. Immunol. Methods, Aug. 2003, 279:219-32.
Lu et al., "Fab-scFv fusion protein: an efficient approach to production of bispecific antibody fragments," J. Immunol. Methods, Sep. 15, 2002, 267:213-26.
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267(24):7246-57 (2000).
MacCallum et al., "Antibody-antigen interactions: contact analysis and binding site topography," J. Mol. Biol., 262:732-45 (1996).
Mack et al., "A small bispecific antibody construct expressed as a functional single-chain molecule with high tumor cell cytotoxicity," Proc. Natl. Acad. Sci. USA, 92(15):7021-7025 (1995).
Maeda et al., "pH-dependent receptor/ligand dissociation as a determining factor for intracellular sorting of ligands for epidermal growth factor receptors in rat hepatocytes," J. Control Release, 82(1):71-82 (2002).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Maity et al., "Equilibrium unfolding of dimeric and engineered monomeric forms of Cro (F58W) repressor and the effect of added salts: evidence for the formation of folded monomer induced by sodium perchlorate," Archives of Biochemistiy and Biophysics, 434:93-107 (2005).
Mallender et al., "Construction, expression and activity of a bivalent bispecific single-chain antibody," J. Biol. Chem., 269(1):199-206 (1994).
Manz et al., Bioanalytical Chemistry, World Scientific Publishing Co., p. 7 (2003).
Manzke et al., "Single-step purification of bispecific monoclonal antibodies for immunotherapeutic use by hydrophobic interaction chromatography," J. Immunol. Methods, 1997, 208:65-73.
Marshall et al., "Rational design and engineering of therapeutic proteins," Drug Discov Today, Mar. 1, 2003, 8(5):212-21.
Marti et al., "Inverse electrostatic effect: electrostatic repulsion in the unfolded state stabilizes a leucine zipper," Biochemistiy, 43(39):12436-47 (2004).

(56) References Cited

OTHER PUBLICATIONS

Martin et al., "Crystal structure at 2.8 A of an FcRn/heterodimeric Fc complex: mechanism of pH-dependent binding," Mol. Cell, 7:867-877 (2001).
Martinez et al., "Disulfide connectivity of human immunoglobulin G2 structural isoforms," Jul. 15, 2008, 47(28):7496-508, doi: 10.1021/bi800576c. Epub Jun. 13, 2008.
Marvin et al., "Recombinant approaches to IgG-like bispecific antibodies," Acta. Pharmacol. Sin., Jun. 2005, 26:649-58.
Marvin et al., "Redesigning an antibody fragment for faster association with its antigen," Biochemistiy, 42:7077-83 (2003).
Massino et al., "Quantitative analysis of the products of IgG chain recombination in hybrid hybridomas based on affinity chromatography and radioimmunoassay," J. Immunol. Methods, Feb. 14, 1997, 201:57-66.
Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model," J. Exp. Med., 198:497-503 (2003).
Matsuoka et al., "A Novel Type of Cell Death of Lymphocytes Induced by a Monoclonal Antibody without Participation of Complement," J. Exp. Med., 181:2007-2015 (1995).
Maxfield et al., "Endocytic recycling," Nat. Rev. Mol. Cell Biol., 5(2):121-32 (2004).
McCafferty et al., "Phage antibodies: filamentous phage displaying antibody variable domains," Nature, Dec. 6, 1990, 348:552-4.
McEarchern et al., "Engineered anti-CD70 antibody with multiple effector functions exhibits in vitro and in vivo antitumor activities," Blood, Feb. 1, 2007, 109(3):1185-92, Epub Oct. 12, 2006.
McGuinness et al., "Phage diabody repertoires for selection of large number of bispecific antibody fragments," Nature Biotechnology, 14(9):1149-1154 (1996).
McPhee et al., "Engineering human immunodeficiency virus 1 protease heterodimers as macromolecular inhibitors of viral maturation," Proc Natl Acad Sci USA, Oct. 15, 1996, 93(21):11477-81.
Medesan et al., "Delineation of the amino acid residues involved in transcytosis and catabolism of mouse IgG1," J Immunol., Mar. 1, 1997, 158(5):2211-7.
Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).
Menegatti et al., "Factor X Deficiency," Semin. Thromb. Hemost., Jun. 2009, 35:407-15.
Meng et al., "The evaluation of recombinant, chimeric, tetravalent antihuman CD22 antibodies," Clinical Cancer Research, 10:1274-1281 (2004).
Merchant et al., "An efficient route to human bispecific IgG," Nat. Biotechnol., Jul. 1998, 16:677-681.
Mertens et al., "Factor VIII-Factor IX Interactions: Molecular Sites Involved in Enzyme-Cofactor Complex Assembly," Thromb. Haemost, Aug. 1999, 82:209-17.
Mezzanzanica et al., "Human ovarian carcinoma lysis by cytotoxic T cells targeted by bispecific monoclonal antibodies: analysis of the antibody components," Int J Cancer, 41(4):609-15 (1988).
Michaelsen et al., "A mutant human IgG molecule with only one C1q binding site can activate complement and induce lysis of target cells," Eur J Immunol., Jan. 2006, 36(1):129-38.
Milstein et al., "Hybrid hybridomas and their use in immunohistochemistry," Nature, Oct. 6-12, 1983, 305:537-40.
Miyazaki et al., "Generation of bispecific IgG, which mimics the cofactor function of blood coagulation factor VIII," Seikagaku, Poster sessions (2P-B-161) (2006).
Molhoj et al., "CD19-/CD3-bispecific antibody of the BiTE class is far superior to tandem diabody with respect to redirected tumor cell lysis," Mol Immunol., 44(8):1935-43 (2007).
Moore et al., "Kinetics and thermodynamics of dimer formation and dissociation for a recombinant humanized monoclonal antibody to vascular endothelial growth factor," Biochemistry, 38:13960-13967 (1999).

Morell et al., "Metabolic properties of IgG subclasses in man," J. Clin. Invest, 49(4):673-80 (1970).
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Methods, 24:107-117 (1992).
Morrison, "Two heads are better than one," Nat Biotechnol. Nov. 2007, 25(11):1233-4.
Murata et al., "Anti-Digoxin Fab Variants Generated by Phage Display," Mol Biotechnol. Jun. 2013, 54 (2) :269-77. doi: 10.1007/s12033-012-9564-1.
Murtaugh et al., "A combinatorial histidine scanning library approach to engineer highly pH-dependent protein switches," Protein Sci., 20(9):1619-31 doi:10.1002/pro 696 (2011).
Nakano et al., "Anti-glypican 3 antibodies cause ADCC against human hepatocellular carcinoma cells," Biochem Biophys Res Commun., Jan. 9, 2009, 378(2):279-84. doi: 10.1016/j.bbrc.2008.11.033. Epub Nov. 18, 2008.
Narhi et al., "Asn to Lys mutations at three sites which are N-glycosylated in the mammalian protein decrease the aggregation of *Escherichia coli*-derived erythropoietin," Protein Eng., Feb. 2001, 14(2):135-40.
Natsume et al., "Improving effector functions of antibodies for cancer treatment: Enhancing ADCC and CPC," Drug Des Devel Ther., 3:7-16 (2009).
Nesterova et al., "Glypican-3 as a novel target for an antibody-drug conjugate," AACR Abstract No. 656, Los Angeles, CA (Apr. 4-18, 2007).
Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol, Feb. 2001, 98(2): 164-74.
Ngo et al., "Computational Complexity, Protein Structure Prediction, and the Levinthal Paradox," The Protein Folding Problem and Tertiary Structure Prediction, Merz, Jr. et al. Editors, Birkhauser Boston, 433-506 (1994).
Nieba et al., "Disrupting the hydrophobic patches at the antibody variable/constant domain interface: improved in vivo folding and physical characterization of an engineered scFv fragment," Protein Engineering, 10(4):435-444 (1997).
Nilsson et al., "Induction of split tolerance and clinical cure in high-responding hemophiliacs with factor IX antibodies," Proc. Natl. Acad. Sci. USA, Dec. 1986, 83:9169-73.
Nilsson et al., "Twenty-five years' experience of prophylactic treatment in severe haemophilia A and B," J. Intern. Med., Jul. 1992, 232:25-32.
Nishii, "CD22 antibody therapy," Current Therapy, 20:47-50 (2001) (with English translation).
Nishimoto et al., "Humanized anti-interleukin-6 receptor antibody treatment of multicentric Castleman disease," Blood, 106:2627-32 (2005).
Nishimoto et al., "Interleukin 6: from bench to bedside," Nat. Clin. Pract. Rheumatol., 2:619-626 (2006).
Nitta et al., "Preliminary trial of specific targeting therapy against malignant glioma," Lancet, Feb. 17, 1990, 335:368-371.
Nohaile et al., "Altering dimerization specificity by changes in surface electrostatics," Proc. Natl. Acad. Sci. USA, 98(6):3109-3114 (2001).
O'Shea et al., "Peptide 'Velcro': design of a heterodimeric coiled coil," Curr Biol., Oct. 1, 1993, 3(10):658-67.
Ohtomo et al., "Molecular Cloning and Characterization of a Surface Antigen Preferentially Overexpressed on Multiple Myeloma Cells," Biochem. Biophys. Res. Commun., 258:583-591 (1999).
Oka, "Development of Novel Immunotoxin Using Recombinant Alpha-Sarcin and Its Application Treatment of Hematopoietic Tumor," Sankyo Seimei Kagaku Kenkyu Shinko Zaidan Kenkyu Hokokushu, 12:46-56 (1998) (with concise explanation of Japanese reference in English).
Okubo et al. "The production and characterization of four monoclonal antibodies to human factor X," Nara Med Assoc., 1987, 38(1):20-28.

(56) References Cited

OTHER PUBLICATIONS

Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Ono et al., "The humanized anti-HM1.24 antibody effectively kills multiple myeloma cells by human effector cell-mediated cytotoxicity," Mol. Immunol., 36:387-395 (1999).
Orita et al., "A novel therapeutic approach for thrombocytopenia by minibody agonist of the thrombopoietin receptor," Blood, 105:562-566 (2005).
Ozaki et al., "A Recombinant HLA Class I-Specific Single Chain Fv Diabody Induces Cell Death in Human Lymphoid Malignancies," Blood, 102:933a, Abstract No. 3474 (2003).
Ozaki et al., "Humanized Anti-HM1.24 Antibody Mediates Myeloma Cell Cytotoxicity That Is Enhanced by Cytokine Stimulation of Effector Cells," Blood, 93:3922-3930 (1999).
Ozaki et al., "Immunotherapy of Multiple Myeloma With a Monoclonal Antibody Directed Against a Plasma Cell-Specific Antigen, HML.24," Blood, 90:3179-3186 (1997).
Ozhegov et al., Tolkovyi Slovar Russkogo iazyka: 2004, p. 292 (with an English translation of the relevant passage defining "control").
Padlan, "X-ray crystallography of antibodies," Adv Protein Chem., 1996, 49:57-133.
Pakula et al., "Genetic Analysis of Protein Stability and Function," Annu. Rev. Genet., 23:289-310 (1989).
Palacios et al., "IL-3-dependent mouse clones that express B-220 surface antigen, contain Ig genes in germ-line configuration, and generate B lymphocutes in vivo," Cell, 41:727-734 (1985).
Pan et al., "Blocking neuropilin-1 function has an additive effect with anti-VEGF to inhibit tumor growth," Cancer Cell, Jan. 2007, 11(1):53-67.
Panka et al., "Variable region framework differences result in decreased or increased affinity of variant anti-digoxin antibodies," Proc. Natl. Acad. Sci. USA, 85(9):3080-4 (1988).
Pardridge et al., "Enhanced cellular uptake and in vivo biodistribution of a monoclonal antibody following cationization," J Pharm Sci., Aug. 1995, 84(8):943-8.
Pardridge et al., "Enhanced endocytosis in cultured human breast carcinoma cells and in vivo biodistribution in rats of a humanized monoclonal antibody after cationization of the protein," J. Pharmacol. Exp, Ther., 286(1):548-54 (1998).
Paul, "Structure and function of immunoglobulins," Fundamental Immunology, Third Edition, 292-295 (1993).
Paul, William ed., Fundamental Immunology, $3^{rd}$ edition, p. 242 (1993).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Peipp et al., "Bispecific antibodies targeting cancer cells," Biochem. Soc. Trans., 30:507-511 (2002).
Pejchal et al., "A Conformational Switch in Human Immunodeficiency Virus gp41 Revealed by the Structures of Overlapping Epitopes Recognized by Neutralizing Antibodies," J Virol., Sep. 2009, 83(17):8451-62, doi: 10. 1128/ JVI. 00685-09, Epub Jun. 10, 2009.
Peters et al., "Engineering an improved IgG4 molecule with reduced disulfide bond heterogeneity and increased Fab domain thermal stability," J Biol Chem, Jul. 13, 2012, 287(29): 24525-33. doi: 10.1074/jbc.M112.369744. Epub May 18, 2012.
Petkova et al., "Enhanced half-life of genetically engineered human IgG1 antibodies in a humanized FcRn mouse model: potential application in humorally mediated autoimmune disease," Int. Immunol, Dec. 2006, 18(12):1759-69, Epub Oct. 31, 2006.

Pettersen et al., "The TCR-Binding Region of the HLA Class I $\alpha_2$ Domain Signals Rapid Fas-Independent Cell Death: A Direct Pathway for T Cell-Mediated Killing of Target Cells?" J. Immunol., 160:4343-4352 (1998).
Piétri-Rouxel et al., "The biochemical effect of the naturally occurring Trp64→Arg mutation on human β3-adrenoceptor activity," Eur. J. Biochem., 247:1174-1179 (1997).
Piper et al., "Interferon therapy in primary care," Primary Care Update for Ob/Gyns, Jul. 2001, 8(4):163-69.
Plückthun et al., "New protein engineering approaches to multivalent and bispecific antibody fragments," Immunotechnology, 3:83-105 (1997).
Poduslo et al., "Polyamine modification increases the permeability of proteins at the blood-nerve and blood-brain barriers," J. Neurochem., 66:1599-1609 (1996).
Pokkuluri et al., "A domain flip as a result of a single amino-acid substitution," Structure, Aug. 15, 1998, 6(8):1067-73.
Pons et al., "Energetic analysis of an antigen/antibody interface: alanine scanning mutagenesis and double mutant cycles on the HyHEL-10/lysozyme interaction," Protein Sci., 8(5):958-68 (1999).
Portolano et al., "Lack of Promiscuity in Autoantigen-Specific H and L Chain Combinations as Revealed by Human H andL Chain "Roulette"," J. Immunol., 150(3):880-887 (1993).
Presta, "Engineering of therapeutic antibodies to minimize immunogenicity and optimize function," Adv. DrugDeliv. Rev., 58(5-6):640-56 (2006).
Presta, "Molecular engineering and design of therapeutic antibodies," Curr Opin Immunol., Aug. 2008, 20(4):460-70. doi: 10.1016/j.coi.2008.06.012.
Price et al., "Tissue factor and tissue factor pathway inhibitor," Anaesthesia, May 2004, 59:483-92.
Queen et al., "A humanized antibody that binds to the interleukin 2 receptor," Proc. Natl. Acad. Sci. USA, 86(24):10029-10033 (1989).
Raffen et al., "Reengineering immunoglobulin domain interactions by introduction of charged residues," Protein Eng., Apr. 1998, 11:303-9.
Rajagopal et al., "A form of anti-Tac (Fv) which is both single-chain and disulfide stabilized: comparison with its single-chain and disulfide-stabilized homologs," Protein Engineering, 10(12):1453-1459 (1997).
Rajpal et al., A general method for greatly improving the affinity of antibodies by using combinatorial libraries, Proc. Natl. Acad. Sci. USA, 102:8466-71 (2005).
Raposo et al., "Epitope-specific antibody response is controlled by immunoglobulin Vh polymorphisms," J Exp Med, Mar. 10, 2014, 211(3):405-11. doi:10.1084/ jem. 20130968. Epub Feb. 17, 2014.
Rathanaswami et al., "Demonstration of an in vivo generated sub-picomolar affinity fully human monoclonal antibody to interleukin-8," Biochem. Biophys. Res. Commun., 334:1004-13 (2005).
Reddy et al., "Elimination of Fc receptor-dependent effector functions of a modified IgG4 monoclonal antibody to human CD4," J. Immunol., 164(4):1925-33 (2000).
Reichert et al., "Development trends for monoclonal antibody cancer therapeutics," Nat. Rev. Drug Discov., 6(5):349-56 (2007).
Reichert et al., "Monoclonal antibody successes in the clinic," Nat. Biotechnol., 23:1073-78 (2005).
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997, 13(11):933-43.
Reist et al., "Human IgG2 constant region enhances in vivo stability of anti-tenascin antibody 81C6 compared with its murine parent," Clin Cancer Res., Oct. 1998, 4(10):2495-502.
Ridgway et al., "'Knobs-into-holes' engineering of antibody CH3 domains for heavy chain heterodimerization," Protein Eng., 9:617-621 (1996).
Rispens et al., "Dynamics of inter-heavy chain interactions in human immunoglobulin G (IgG) subclasses studied by kinetic Fab arm exchange," J Biol Chem., Feb. 28, 2014, 289(9):6098-109. doi: 10.1074/jbc.M113.541813. Epub Jan. 14, 2014.
Roguska et al., "Humanization of murine monoclonal antibodies through variable domain resurfacing," Proc Natl Acad Sci USA, 91:969-73 (1994).

(56) References Cited

OTHER PUBLICATIONS

Roitt et al., Immunology, M., Mir, (2000), pp. 110-111 (i113 (including what are believed to be corresponding pages from an English language edition of Immunology).

Roitt et al., Immunology, M., Mir, 5th Edition (2000), pp. 97-113 (including what are believed to be corresponding pages from an English language edition of Immunology).

Roopenian et al., "FcRn: the neonatal Fc receptor comes of age," Nat Rev Immunol., Sep. 2007, 7(9):715-25. Epub Aug. 17, 2007.

Rossi et al., "Development of New Multivalent-bispecific Agents for Pretargeting Tumor Localization and Therapy," Clin. Cancer Res., 9:3886s-3896s (2003).

Rothe et al., "Ribosome display for improved biotherapeutic molecules," Expert Opin. Biol. Ther., 6:177-187 (2006).

Rousch et al., "Somatostatin displayed on filamentous phage as a receptor-specific agonist," Br. J. Pharmacol., 125:5-16 (1998).

Rudikoff et al., "Single amino acid substitution altering antigen-binding specificity," Proc. Natl. Acad. Sci. USA, 79(6):1979-83 (1982).

Ruef et al., "A bispecific antifibrin-antiplatelet urokinase conjugate (BAAUC) induces enhanced clot lysis and inhibits platelet aggregation," Thromb. Haemost., Jul. 1999, 82(1):109-14.

Ruf et al., "Induction of a long-lasting antitumor immunity by a trifunctional bispecific antibody," Blood, Oct. 15, 2001, 98(8):2526-34.

Ruf et al., "Pharmacokinetics and in vivo stability of intraperitoneally administered therapeutic antibody catumaxomab," J. Clin. Oncol., 26 (May 20 suppl) (2008), abstr 14006.

Ruggeri et al., "von Willebrand Factor and von Willebrand Disease," Blood, Oct. 1987, 70(4):895-904.

Ryman et al., "Pharmacokinetics of Monoclonal Antibodies," CPT Pharmacometrics Syst. Pharmacol., Sep. 2017, 6(9):576-588. doi: 10.1002/psp4.12224, Epub Jul. 29, 2017.

Saito et al., "Establishment of Factor VIII Mimetic Antibodies and Their In Vitro Activities in Hemophilia A," 2006 National Hemophilia Foundation Symposia.

Saito et al., "Factor VIII Mimetic Antibody: (1) Establishment and Characterization of Anti-factor IX/anti-factor X Bispecific Antibodies," 2005 International Society of Thrombosis and Haemostasis, vol. 3, Issue Supplement s1, p. #QR160.

Salfeld et al., "Isotype selection in antibody engineering," Nat. Biotechnol., 25:1369-72 (2007).

Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).

Sampei et al., "Identification and multidimensional optimization of an asymmetric bispecific IgG antibody mimicking the function of factor VIII cofactor activity," PLoS One, 2013, 8(2):e57479. doi: 10.1371/journal.pone.0057479. Epub Feb. 28, 2013.

Sampei et al., "Non-antigen-contacting region of an asymmetric bispecific antibody to factors IXa/X significantly affects factor VIII-mimetic activity," mAbs, 2015, 7(1):120-8. doi: 10.4161/19420862.2015.989028.

Sarkar et al., "Rational cytokine design for increased lifetime and enhanced potency using pH-activated "histidine switching"," Nat Biotechnol., Sep. 2002, 20(9):908-13, Epub Aug. 5, 2002.

Sarmay et al., "Mapping and comparison of the interaction sites on the Fc region of IgG responsible for triggering antibody dependent cellular cytotoxicity (ADCC) through different types of human Fc gamma receptor," Mol. Immunol., 29(5):633-9 (1992).

Sato et al., "CD22 Is Both a Positive and Negative Regulator of B Lymphocyte Antigen Receptor Signal Transduction: Altered Signaling in CD22-Deficient Mice," Immunity, 5:551-562 (1996).

Sato et al., "Properties of Two VEGF Receptors, Flt-1 and KDR, in Signal Transduction," Ann N.Y. Acad. Sci, May 2000, 902:201-207, discussion 205-7.

Sato et al., "Reshaping a human antibody to inhibit the interleukin 6-dependent tumor cell growth," Cancer Res., 53:851-856 (1993).

Schaefer et al., "Immunoglobulin domain crossover as a generic approach for the production of bispecific IgG antibodies," Proc Natl Acad Sci USA, Jul. 5, 2011, 108(27):11187-92. doi: 10.1073/pnas.1019002108. Epub Jun. 20, 2011.

Schaeffer et al., "The Rat Glomerular Filtration Barner Does Not Show Negative Charge Selectivity," Microcirculation, 9:329-342 (2002).

Scheurle et al., "Cancer Gene Discovery Using Digital Differential Display," Cancer Res., 60:4037-4043 (2000).

Schlereth et al., "T-cell activation and B-cell depletion in chimpanzees treated with a bispecific anti-CD19/anti-CD3 single-chain antibody construct," Cancer Immunol Immunother., May 2006, 55(5):503-14, Epub Jul. 20, 2005.

Schmidt et al., "Structure-function relationships in factor IX and factor IXa," Trends Cardiovasc Med., Jan. 2003, 13(1):39-45.

Schmidt et al., "Hemostasis and Coagulation," Human Physiology, Moscow, 2:431-436 (1996) (with English translation).

Schmidt et al., "Enzymes of the pancreatic juice," Human Physiology, Moscow, 3:764 (1996) (with English translation).

Schmitz et al., "Phage display: a molecular tool for the generation of antibodies—a review," Placenta., 21 Suppl A:S106-12 (2000).

Schuurman et al., "Normal human immunoglobulin G4 is bispecific: it has two different antigen-combining sites," Immunology, Aug. 1999, 97(4):693-8.

Schuurman et al., "The inter-heavy chain disulfide bonds of IgG4 are in equilibrium with intra-chain disulfide bonds," Mol Immunol., Jan. 2001, 38(1):1-8.

Sebastian et al., "Treatment of non-small cell lung cancer patients with the trifunctional monoclonal antibody catumaxomab (anti-EpCAM x anti-CD3): a phase I study," Cancer Immunol Immunother., 56(10):1637-44 (2007).

Segal et al., "Bispecific antibodies in cancer therapy," Curr. Opin. Immunol., 11:558-562 (1999).

Segal et al., "Introduction: bispecific antibodies," J. Immunol. Methods, Feb. 1, 2001, 248:1-6.

Seimetz et al., "Development and approval of the trifunctional antibody catumaxomab (anti-EpCAM x anti-CD3) as a targeted cancer immunotherapy," Cancer Treat Rev., 36(6):458-67 (2010).

Sequence alignments and modification scheme (document filed during Oral Proceedings and mentioned in minutes of the Oral Proceedings posted by EPO on Jul. 25, 2018); 3 pages.

Shalaby et al., "Development of Humanized Bispecific Antibodies Reactive with Cytotoxic Lymphocytes and Tumor Cells Overexpressing the HER2 Protooncogene," J. Exp. Med., 175:217-225 (1992).

Sharifi et al., "Improving monoclonal antibody pharmacokinetics via chemical modification," Q J Nucl Med., Dec. 1998, 42(4):242-9.

Shaul, "Exploring the charge space of protein-protein association: a proteomic study," Proteins, 60:341-352 (2005).

Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).

Shima et al., "Factor VIII Mimetic Antibody: (2) In Vitro Assessment of Cofactor Activity in Hemophilia A," 2005 International Society of Thrombosis and Haemostasis, vol. 3, Issue Supplement s1, p. #P0038.

Shima et al., "Factor VIII Taitei Kotai (2), Ketsuyubyo A Kanja Katsueki ni okeru in vitro Gyoko Kassei no Kento", Rinsho Ketsueki, Aug. 30, 2005, 46(8):777 (#WS-36-5) (with English translation).

Shima, M., "Bispecific antibodies to coagulation factors IXa and X mimic the function of factor VIII," 2006 World Federation of Haemophilia (Haemophilia, 12(Suppl. 2):98 (2006)).

Shimba et al., "Comparative thermodynamic analyses of the Fv, Fab* and Fab fragments of anti-dansyl mouse monoclonal antibody," FEBS Letters, 360:247-250 (1995).

Shirahata, Minna ni yakudatsu ketsuyubyo no kiso to rinsho. Iyaku (Medicine and Drug) Journal Co., Ltd., 280-9 (2009) (with English translation).

Shire et al., "Challenges in the development of high protein concentration formulations," Journal of Pharmaceutical Sciences, 93(6):1390-1402 (2004).

(56) References Cited

OTHER PUBLICATIONS

Singer et al., Genes & Genomes, 1998; 1:63-64 (with English translation).
Sinha et al., "Electrostatics in protein binding and function," Curr. Protein Pept. Sci., 3(6):601-14 (2002).
Sinha et al., "Molecular dynamics simulation of a high-affinity antibody-protein complex: the binding site is a mosaic of locally flexible and preorganized rigid regions," Cell Biochem Biophys., 43:253-273 (2005).
Skerra, "Use of the tetracycline promoter for the tightly regulated production of a murine antibody fragment in *Escherichia coli*," Gene, 151:131-135 (1994).
Smans et al., "Bispecific antibody-mediated lysis of primary cultures of ovarian carcinoma cells using multiple target antigens," Int. J. Cancer, 83:270-277 (1999).
Smith et al., "The challenges of genome sequence annotation or 'the devil is in the details'," Nature Biotechnology, Nov. 1997, 15:1222-1223.
Smith et al., "Inhibition of T Cell Activation by a Monoclonal Antibody Reactive Against the α3 Domain of Human MHC Class I Molecules," J. Immunol., 153:1054-1067 (1994).
Smith, "Creative Expression: Mammalian Expression Vectors and Systems," The Scientist Magazine, Feb. 2, 1998, 3 pages.
Smith-Gill et al., "Contributions of immunoglobulin heavy and light chains to antibody specificity for lysozyme and two haptens," The Journal of Immunology, 139:4135-4144 (1987).
Smolen et al., "Interleukin-6: a new therapeutic target," Arthritis Res Ther., 2006, 8 Suppl 2:S5. Epub Jul. 28, 2006.
Soeda et al., "Factor VIII Taitei Kotai (1) Ko FIXa/FX bispecific Kotai no Sakusei oyobi characterization," Rinsho Ketsueki, 46(8):728 (2005) (with English translation).
Soeda et al., "Phage library-ho ni yori Sakusei shita Ko-FIXa/Ko-FX bispecific Kotai no FVIII Taitei Sayo," Jpn J Thromb Hemost., 16(5):526 (2005) (with English translation).
Song et al., "Light chain of natural antibody plays a dominant role in protein antigen binding," Biochemical and Biophysical Research Communications, 268:390-394 (2000).
Souyri, M., "Mpl: from an acute myeloproliferative virus to the isolation of the long sought thrombopoietin," Seminars in Hematology, 35(3):222-231 (1998).
Spiess et al., "Bispecific antibodies with natural architecture produced by co-culture of bacteria expressing two distinct half-antibodies," Nat Biotechnol., Aug. 2013, 31(8):753-8. doi: 10.1038/nbt.2621. Epub Jul. 7, 2013.
Stancovski et al., Mechanistic Aspects of the Opposing Effects of Monoclonal Antibodies to the ERBB2 Receptor on Tumor Growth, Proc. Natl. Acad. Sci. USA, Oct. 1, 1991, 88(19):8691-8695.
Staerz et al., "Hybrid antibodies can target sites for attack by T cells," Nature, 314(6012):628-31 (1985).
Staerz et al., "Hybrid hybridoma producing a bispecific monoclonal antibody that can focus effector T-cell activity," Proc Natl Acad Sci USA, 83:1453-7 (1986).
Stickney et al., "Bifunctional Antibody: A Binary Radiopharmaceutical Delivery System for Imaging Colorectal Carcinoma," Cancer Res., Dec. 15, 1991, 51:6650-5.
Strand et al., "Biologic therapies in rheumatology: lessons learned, future directions," Nat. Rev. Drug Discov., 6:75-92 (2007).
Stroehlein et al., "Induction of anti-tumor immunity by trifunctional antibodies in patients with peritoneal carcinomatosis," J Exp Clin Cancer Res., Feb. 14, 2009, 28:18. doi: 10.1186/1756-9966-28-18.
Strohl, "Optimization of Fc-mediated effector functions of monoclonal antibodies," Curr Opin Biotechnol., Dec. 2009, 20(6):685-91. doi: 10,1016/j.copbio.2009.10.011. Epub Nov. 4, 2009.
Summary of information about antibodies in Examples of EP 2006381 (document submitted in EP opposition and posted by EPO on Apr. 13, 2018), 3 pages.
Sun et al., "Coexpression of Gas6/Axl in human ovarian cancers," Oncology, 66(6):450-7 (2004).
Suresh et al., "Advantages of bispecific hybridomas in one-step immunocytochemistry and immunoassays," Proc. Natl. Acad. Sci. USA, Oct. 1986, 83:7989-93.
Suresh et al., "Bispecific monoclonal antibodies from hybrid hybridomas," Methods Enzymol., 1986, 121:210-228.
Suzuki, "Research and Development of Antibody Pharmaceuticals," NIBS Letter, 56(4):45-51 (2010) (with English translation).
Tabrizi et al., "Elimination mechanisms of therapeutic monoclonal antibodies," Drug Discov Today, Jan. 2006, 11(1-2):81-8.
Tahtis et al., "Biodistribution Properties of $^{111}$ Indium-labeled C-Functionalized trans-Cyclohexyl Diethylenetriaminepentaacetic Acid Humanized 3S193 Diabody and F(ab')$_2$ Constructs in a Breast Carcinoma Xenograft Model," Clin. Cancer Res., 7:1061-1072 (2001).
Taki, The Journal of Japanese Society on Thrombosis and Hemostasis, Feb. 2, 2002; 13:109-113.
Tamura et al., "Structural correlates of an anticarcinoma antibody: identification of specificity-determining residues (SDRs) and development of a minimally immunogenic antibody variant by retention of SDRs only," J Immunol., Feb. 1, 2000, 164(3):1432-41.
Tan et al., "Contributions of a highly conserved $V_H/V_L$ hydrogen bonding interaction to scFv folding stability and refolding efficiency," Biophysical Journal, 75:1473-1482 (1998).
Tan et al., "Engineering the isoelectric point of a renal cell carcinoma targeting antibody greatly enhances scFv solubility," Immunotechnology, 4(2):107-114 (1998).
Tang et al., "Selection of linkers for a catalytic single-chain antibody using phage display technology", The Journal of Biological Chemistry, 271(26):15682-15686 (1996).
Tarditi et al., "Selective high-performance liquid chromatographic purification of bispecific monoclonal antibodies," J. Chromatogr., 599:13-20 (1992).
Tedder et al., "CD22, a B Lymphocyte-Specific Adhesion Molecule That Regulates Antigen Receptor Signaling," Annu. Rev. Immunol., 15:481-504 (1997).
Teeling et al., "The biological activity of human CD20 monoclonal antibodies is linked to unique epitopes on CD20," J. Immunol., 177(1):362-71 (2006).
Teerinen et al., "Structure-based stability engineering of the mouse IgG1 Fab fragment by modifying constant domains," J Mol Biol., 361(4):687-97 (2006).
Ten Kate et al., "Effect of isoelectric point on biodistribution and inflammation: imaging with indium-111-labelled IgG," Eur. J. Nucl. Med., 17:305-309 (1990).
Thakur et al., "Cancer therapy with bispecific antibodies: Clinical experience," Curr Opin Mol Ther., 12(3):340-9 (2010).
Thies et al., "The alternatively folded state of the antibody C(H)3 domain," J Mol Biol., Jun. 22, 2001, 309(5):1077-85.
Thilenius et al., "Agonist antibody and Fas ligand mediate different sensitivity to death in the signaling pathways of Fas and cytoplasmic mutants," Eur. J. Immunol., 27:1108-1114 (1997).
Tsubaki et al., "C-terminal modification of monoclonal antibody drugs: amidated species as a general product-related substance," Int J Biol Macromol., 52:139-47. doi: 10.1016/j.ijbiomac.2012.09.016, Epub Sep. 25, 2012.
Tsuchiya, Credit Suisse Seminar, "Therapeutic Antibody," at Fuji-Gotemba Laboratories, p. 21 (2006) (with English translation).
Tsurushita et al., "Design of humanized antibodies: From anti-Tac to Zenapax," Methods, 36:69-83 (2005).
Turner et al., "Importance of the linker in expression of single-chain Fv antibody fragments: optimization of peptide sequence using phage display technology," Journal of Immunological Methods, 205:43-54 (1997).
Vaccaro et al., "Divergent activities of an engineered antibody in murine and human systems have implications for therapeutic antibodies," Proc Natl Acad Sci USA, Dec. 5, 2006, 103(49):18709-14, Epub Nov. 20, 2006.
Vaisitti et al., "Cationization of monoclonal antibodies: another step towards the 'magic bullet'?," J. Biol. Regul. Homeost. Agents., 19(3-4):105-12 (2005).
Vajdos et al., "Comprehensive functional maps of the antigen-binding site of an anti-ErbB2 antibody obtained with shotgun scanning mutagenesis," J. Mol. Biol., 320(2):415-28 (2002).

(56) References Cited

OTHER PUBLICATIONS

Van Den Abbeele et al., "Antigen-Binding Site Protection During Radiolabeling Leads to a Higher Immunoreactive Fraction," J Nucl Med, Jan. 1991, 32(1):116-22.
Van Den Burg et al., "Selection of mutations for increased protein stability," Curr. Opin. Biotechnol., 13(4):333-337 (2002).
Van Der Neut Kolfschoten et al., "Anti-inflammatory activity of human IgG4 antibodies by dynamic Fab arm exchange," Science, Sep. 14, 2007, 317(5844):1554-7.
Van Loghem et al., "Staphylococcal protein A and human IgG subclasses and allotypes," Scand. J. Immunol., 15(3):275-8 (1982).
Van Walle et al., "Immunogenicity screening in protein drug development," Expert Opin. Biol. Ther., 7(3):405-18 (2007).
Vargas-Madrazo et al., "An improved model of association for VH-VL immunoglobulin domains: asymmetries between VH and VL in the packing of some interface residues," J. Mol. Recognit., 16(3):113-20 (2003).
Vaughan et al., "Human antibodies with sub-nanomolar affinities isolated from a large non-immunized phage display library," Nat Biotechnol., Mar. 1996, 14(3):309-14.
Vehar et al., "Structure of human factor VIII," Nature, 312(5992):337-42 (1984).
Verhoeyen et al., "Construction of a reshaped HMFG1 antibody and comparison of its fine specificity with that of the parent mouse antibody," Immunology, Mar. 1993, 78(3):364-70.
Verhoeyen et al., "Monoclonal Antibodies in Clinical Oncology," 1991, Edited by AA Epenetos, Chapter 5, pp. 37-43, Chapman and Hall.
Vieille et al., "Hyperthermophilic enzymes: sources, uses, and molecular mechanisms for thermostability," Microbiology and Molecular Biology Reviews, 65(1):1-43 (2001).
Volkel et al., "Optimized linker sequences for the expression of monomeric and dimeric bispecific single-chain diabodies," Protein Engineering, 14(10):815-823 (2001).
Wally et al., "Identification of a novel substitution in the constant region of a gene coding for an amyloidogenic kappa1 light chain," Biochim Biophys Acta., May 31, 1999, 1454(1):49-56.
Wang et al., "Conserved amino acid networks involved in antibody variable domain interactions," Proteins, Jul. 2009, 76(1):99-114. doi: 10.1002/prot.22319.
Wang et al., "Polyethylene Glycol-modified Chimeric Toxin Composed of Transforming Growth Factor alpha and Pseudomonas Exotoxin," Cancer. Res., 53:4588-4594 (1993).
Wang et al., "A New Recombinant Single Chain Trispecific Antibody Recruits T Lymphocytes to Kill CEA (Carcinoma Embryonic Antigen) Positive Tumor Cell In Vitro Efficiently," J Biochem. Apr. 2004, 135(4):555-65.
Ward et al., "Binding activities of a repertoire of single immunoglobulin variable domains secreted from *Escherichia coli*," Nature, Oct. 12, 1989, 341(6242):544-6.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987, 26(13):4131-8.
Warnaar et al., "Purification of bispecific F(ab')2 from murine trinoma OC/TR with specificity for CD3 and ovarian cancer," Hybridoma, 13:519-526 (1994).
Weiner et al., "A Human Tumor Xenograft Model of Therapy with a Bispecific Monoclonal Antibody Targeting c-erbB-2 and CD16," Cancer Res., Jan. 1, 1993, 53:94-100.
Weiner et al., "The Role of T Cell Activation in Anti-CD3 x Antitumor Bispecific Antibody Therapy," J. Immunol., Mar. 1, 1994, 152:2385-92.
Wells, "Perspectives in Biochemistry," Biochemistry, 29(37):8509-8517 (1990).
Whitlow et al., "An improved linker for single-chain Fv with reduced aggregation and enhanced proteolytic stability," Protein Engineering, 6(8):989-995 (1993).

Wiens et al., "Mutation of a single conserved residue in VH complementarity-determining region 2 results in a severe Ig secretion defect," J. Immunol., 167(4):2179-86 (2001).
Wiens et al., "Somatic mutation in VH complementarity-determining region 2 and framework region 2: differential effects on antigen binding and Ig secretion," J. Immunol., 159(3):1293-302 (1997).
Wines et al., "The IgG Fc contains distinct Fc receptor (FcR) binding sites: the leukocyte receptors Fc gamma RI and Fc gamma RIIa bind to a region in the Fc distinct from that recognized by neonatal FcR and protein A," J Immunol, May 15, 2000, 164(10):5313-8.
Wolf et al., "BiTEs: bispecific antibody constructs with unique anti-tumor activity," Drug Discov Today, 10(18):1237-44 (2005).
Wood et al., "Expression of active human factor VIII from recombinant DNA clones," Nature, 312(5992):330-7 (1984).
Woodle et al., "Anti-Human Class I MHC Antibodies Induce Apoptosis by a Pathway That Is Distinct from the Fas Antigen-Mediated Pathway," J. Immunol., 158:2156-2164 (1997).
Woodle et al., "Anti-Human Class I α3 Domain-Specific Monoclonal Antibody Induces Programmed Cell Death in Murine Cells Expressing Human Class I MHC Transgenes," Transplant. Proc., 30:1059-1060 (1998).
Woodle et al., "Class I MHC Mediates Programmed Cell Death in Human Lymphoid Cells," Transplantation, 64:140-146 (1997).
Worn et al., "Stability engineering of antibody single-chain Fv fragments," J. Mol. Biol., 305:989-1010 (2001).
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Development of motavizumab, an ultra-potent antibody for the prevention of respiratory syncytial virus infection in the upper and lower respiratory tract," J. Mol. Biol., 368(3):652-65 (2007).
Wu et al., "Multimerization of a chimeric anti-CD20 single-chain Fv-Fc fusion protein is mediated through variable domain exchange," Protein Eng., 14(12):1025-33 (2001).
Wu et al., "Tumor localization of anti-CEA single-chain Fvs: improved targeting by non-covalent dimers," Immunotechnology, 2:21-36 (1996).
Wu et al., "Ultra-potent Antibodies Against Respiratory Syncytial Virus: Effects of Binding Kinetics and Binding Valence on Viral Neutralization," J. Mol. Biol., Jul. 1, 2005, 350(1):126-44.
Wypych et al., "Human IgG2 antibodies display disulfide-mediated structural isoforms," J. Biol. Chem., 283(23):16194-16205 (2008).
Xiang et al., "Production of Murine V-Human Crl Chimeric Anti-TAG72 Antibody Using V Region cDNA Amplified by PCR," Mol. Immunol., Aug. 1990, 27:809-17.
Xiang et al., "Study of B72.3 combining sites by molecular modeling and site-directed mutagenesis," Protein Eng., 13(5):339-44 (2000).
Xiong et al., "Efficient inhibition of human B-cell lymphoma xenografts with an anti-CD20 X anti-CD3 bispecific diabody," Cancer Lett., 177:29-39 (2002).
Xu et al., "Insight into hepatocellular carcinogenesis at transcriptome level by comparing gene expression profiles of hepatocellular carcinoma with those of corresponding noncancerous liver," Proc. Natl. Acad. Sci. USA, 98:15089-15094 (2001).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "CDR walking mutagenesis for the affinity maturation of a potent human anti-HIV-1 antibody into the picomolar range," J. Mol. Biol., Dec. 1, 1995, 254(3):392-403.
Yang et al., "Tailoring structure-function and pharmacokinetic properties of single-chain Fv proteins by site-specific PEGylation," Protein Eng., 16:761-770 (2003).

(56) References Cited

OTHER PUBLICATIONS

Yasukawa et al., "Structure and expression of human B cell stimulatory factor-2 (BSF-2/IL-6) gene," EMBO J., Oct. 1987, 6(10):2939-45.
Yarilin, Principles of immunology: M: Medicina, 1999, pp. 169-172, 354-8 (with English translation), 21 pages.
Yarilin, Principles of immunology: M: Medicina, 1999, pp. 169-174 (with English translation), 8 pages.
Zeidler et al., "Simultaneous Activation of T Cells and Accessory Cells by a New Class of Intact Bispecific Antibody Results in Efficient Tumor Cell Killing," J Immunol, Aug. 1, 1999, 163(3):1246-52.
Zeidler et al., "Simultaneous Activation of T Cells and Accessory Cells by a New Class of Intact Bispecific Antibody Results in Efficient Tumor Cell Killing," Br J Cancer, Jul. 2000, 83(2):261-6.
Zhu et al., "An efficient route to the production of an IgG-like bispecific antibody", Protein Eng., 13:361-367 (2000).
Zhu et al., "MHC class I-related neonatal Fc receptor for IgG is functionally expressed in monocytes, intestinal macrophages, and dendritic cells," J. Immunol., 166(5):3266-76 (2001).
Zhu et al., "Remodeling domain interfaces to enhance heterodimer formation," Protein Science, 6:781-788 (1997).
Zuckier et al., "Chimeric human-mouse IgG antibodies with shuffled constant region exons demonstrate that multiple domains contribute to in vivo half-life," Cancer Res., 58:3905-08 (1998).
Zuo et al., "An efficient route to the production of an IgG-like bispecific antibody," Protein Eng., 13(5):361-7 (2000).
Zwick et al., "The long third complementarity-determining region of the heavy chain is important in the activity of the broadly neutralizing anti-human immunodeficiency virus type 1 antibody 2F5," J. Virol., 78(6):3155-61 (2004).
International Preliminary Report on Patentability for App. Ser. No. PCT/JP2016/088820, dated Jul. 12, 2018, 12 pages.
International Search Report for App. Ser. No. PCT/JP2016/088820, dated Mar. 7, 2017, 7 pages.
U.S. Appl. No. 16/298,032, Igawa et al., filed Mar. 11, 2019.
U.S. Appl. No. 17/336,538, Igawa et al., filed Jun. 2, 2021.
U.S. Appl. No. 16/459,791, Igawa et al., filed Jul. 2, 2019.
U.S. Appl. No. 15/024,063, Igawa et al., filed Mar. 23, 2016.
U.S. Appl. No. 15/562,186, Igawa et al., filed Sep. 27, 2017.
U.S. Appl. No. 15/782,256, Igawa et al., filed Oct. 12, 2017.
U.S. Appl. No. 17/130,736, Hattori et al., filed Dec. 22, 2020.
U.S. Appl. No. 15/725,692, Igawa et al., filed Oct. 5, 2017.
U.S. Appl. No. 13/990,088, Nezu et al., filed Dec. 19, 2013.
U.S. Appl. No. 16/008,486, Igawa et al., Jun. 14, 2018.
U.S. Appl. No. 17/336,538, Igawa et al., Jun. 2, 2021.
Antibodies in Example 29 of EP 2 202 245, 2 pages (cited by the opponent during the opposition proceedings of EP 2 202 245 on May 19, 2020).
Annex from opponent 2's submission of Jun. 7, 2018, 13 pages (cited by the opponent during the opposition proceedings of EP 2 202 245 on May 19, 2021).
Baeuerle et al., "BiTE: Teaching antibodies to engage T-cells for cancer therapy," Curr Opin Mol Ther, Feb. 2009, 11(1):22-30.
Bolt et al., "The generation of a humanized, non-mitogenic CD3 monoclonal antibody which retains in vitro immunosuppressive properties," Eur J Immunol, Feb. 1993, 23(2):403-411.
Brezski et al., "The origins, specificity, and potential biological relevance of human anti-IgG hinge autoantibodies," Scientific World Journal, May 26, 2011, 11:1153-1167.
Brischwein et al., "MT110: A novel bispecific single-chain antibody constmct with high efficacy in eradicating established tumors," Mol Immunol, Mar. 2006, 43(8):1129-1143. doi: 10.1016/j.molimm.2005.07.034. Epub Sep. 1, 2005.
Bugelski et al., "Monoclonal antibody-induced cytokine-release syndrome," Expert Rev Clin Immunol, Sep. 2009, 5(5):499-521.
Carter et al., "Potent antibody therapeutics by design," Nat Rev Immunol, May 2006, 6(5):343-357.
Hammond et al., "Selective Targeting and Potent Control of Tumor Growth Using an EphA2/CD3-Bispecific Single-Chain Antibody Construct," Cancer Res, Apr. 15, 2007, 67(8):3927-3935. doi: 10.1158/0008-5472.CAN-06-2760.
Ho et al., "In vitro antibody evolution targeting germline hot spots to increase activity of an anti-CD22 immunotoxin," J Biol Chem, Jan. 7, 2005, 280(1):607-617. doi: 10.1074/jbc.M409783200. Epub Oct. 18, 2004.
Kontermann, "Strategies to Extend Plasma Half-Lives of Recombinant Antibodies," BioDrugs, 2009, 23(2):93-109. doi: 10.2165/00063030-200923020-00003.
Lutterbuese et al., "Potent tumor killing and inhibition of tumor growth b CEA/CD3-bispecific single chain antibodies that are resistant to inhibition by soluble CEA," Proc Am Assoc Cancer Res, from 98th AACR Annual Meeting, May 2007, vol. 67, Issue 9, Abstract 4106.
Lutterbuese et al., "Conversion of Cetuximab and Trastuzumab into T cell-engaging BiTE antibodies creates novel drug candidates with superior anti-tumor activity," Proc Am Assoc Cancer Res, from 99th AACR Annual Meeting, May 2008, vol. 68, Issue 9, Abstract 2402.
Marchalonis et al., "Antigenic mapping of a human lambda light chain: correlation with three dimensional structure," J Protein Chem, Apr. 1992, 11(2):129-137.
Representative abstracts allegedly showing long-term administration of a variety of anti-cancer antibodies in the prior art, 5 pages (document submitted by the opponents in the opposition proceedings of EP 2 647 707 and reported in the EPO Communication issued Jan. 20, 2021; the document cites publication dates of the abstracts ranging from May 2006 to Feb. 2010).
Rother et al., "Discovery and development of the complement inhibitor eculizumab for the treatment of paroxysmal nocturnal hemoglobinuria," Nat Biotechnol, Nov. 2007, 25(11):1256-1264.
Saunders et al., "Conceptual Approaches to Modulating Antibody Effector Functions and Circulation Half-Life," Front Immunol, Jun. 7, 2019, 10(1296):1-20.
Schneider et al., "In vitro and in vivo properties of a dimeric bispecific single-chain antibody IgG-fusion protein for depletion of CCR2+ target cells in mice," Eur J Immunol, Mar. 2005, 35(3):987-995.
Screenshots of Genetyx software, 3 pages (document cited by opponent during the opposition proceedings of EP 2 202 245 on May 22, 2020).
Screenshots of the web-based calculator, 9 pages (document cited by opponent during the opposition proceedings of EP 2 202 245 on May 22, 2020).
Sections of the Genetyx manual pertaining to isoelectric point, 5 pages (document cited by opponent during the opposition proceedings of EP 2 202 245 on May 22, 2020, with English translation).
Sequence Alignments (comparison of heavy chain constant region), 1 page (submitted by the Patentee (Chugai Seiyaku Kabushiki Kaisha) in the opposition proceedings of EP 2 647 707 on Dec. 23, 2020).
Taylor et al., "A new era for hemophilia B treatment," Blood, Apr. 7, 2016, 127(14):1734-1736.
Thomas et al., "A Cell-Based Artificial Antigen-Presenting Cell Coated with Anti-CD3 and CD28 Antibodies Enables Rapid Expansion and Long-Term Growth of CD4 T Lymphocytes," Clin Immunol, Dec. 2002, 105(3):259-272.
Weiner et al., "The Role of T Cell Activation in Anti-CD3 x Antitumor Bispecific Antibody Therapy," J Immunol, Mar. 1, 1994, 152(5):2385-2392.
Zhao et al., "Targeting CD37-positive lymphoid malignancies with a novel engineered small modular immunopharmaceutical," Blood, Oct. 1, 2007, 110(7):2569-2577.
International Search Report for App. Ser. No. PCT/JP2018/048409, dated Mar. 26, 2019, 4 pages.
U.S. Appl. No. 10/575,905, Hattori et al., filed Apr. 30, 2007 (abandoned).
U.S. Appl. No. 15/614,842, Igawa et al., filed Jun. 6, 2017.
U.S. Appl. No. 17/530,542, Igawa et al., filed Nov. 19, 2021.
U.S. Appl. No. 16/298,032, Igawa et al., filed Mar. 11, 2019 (abandoned).
U.S. Appl. No. 13/257,145, Igawa et al., filed Nov. 22, 2011 (abandoned).
U.S. Appl. No. 17/574,614, Igawa et al., filed Jan. 13, 2022.

(56) References Cited

OTHER PUBLICATIONS

U.S. Appl. No. 17/336,538, Igawa et al., filed Jun. 2, 2021 (abandoned).
U.S. Appl. No. 17/076,938, Igawa et al., filed Oct. 22, 2020 (abandoned).
U.S. Appl. No. 16/815,089, Igawa et al., filed Mar. 11, 2020 (abandoned).
U.S. Appl. No. 16/448,088, Igawa et al., filed Jun. 21, 2019 (abandoned).
U.S. Appl. No. 16/155,673, Igawa et al., filed Oct. 9, 2018 (abandoned).
U.S. Appl. No. 15/875,847, Igawa et al., filed Jan. 19, 2018 (abandoned).
U.S. Appl. No. 15/617,008, Igawa et al., filed Jun. 8, 2017 (abandoned).
U.S. Appl. No. 13/518,861, Igawa et al., filed Oct. 4, 2012 (abandoned).
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Appl. No. 15/288,965, Igawa et al., filed Oct. 7, 2016 (abandoned).
U.S. Appl. No. 16/459,791, Igawa et al., filed Jul. 2, 2019 (abandoned).
U.S. Appl. No. 17/485,818, Igawa et al., filed Sep. 27, 2021.
U.S. Appl. No. 17/483,898, Igawa et al., filed Sep. 24, 2021.
U.S. Appl. No. 16/093,495, Saeki et al., filed Oct. 12, 2018.
U.S. Appl. No. 16/496,089, Shima et al., filed Sep. 20, 2019.
U.S. Appl. No. 16/758,128, Hosoguchi et al., filed Apr. 22, 2020.
U.S. Appl. No. 17/520,368, Igawa et al., filed Nov. 5, 2021.
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019 (abandoned).
U.S. Appl. No. 16/825,513, Hattori et al., filed Mar. 20, 2020 (abandoned).
U.S. Appl. No. 17/130,736, Hattori et al., filed Dec. 22, 2020 (abandoned).
U.S. Appl. No. 17/389,534, Hattori et al., filed Jul. 30, 2021.
U.S. Appl. No. 11/910,836, Hattori et al., filed Jan. 12, 2009 (abandoned).
U.S. Appl. No. 17/359,867, Igawa et al., filed Jun. 28, 2021.
U.S. Appl. No. 17/578,524, Igawa et al., filed Jan. 19, 2022.
U.S. Appl. No. 17/367,909, Nezu et al., filed Jul. 6, 2021.
U.S. Appl. No. 16/061,429, Igawa et al., filed Jun. 12, 2018.
U.S. Appl. No. 16/330,269, Yoneyama et al., filed Mar. 4, 2019.
U.S. Appl. No. 16/936,575, Teranishi et al., filed Jul. 23, 2020.
Aalberse et al., "IgG4 breaking the rules," Immunology, Jan. 2002, 105(1):9-19.
Glatter, "Evaluation of Small-Angle Scattering Data from Lamellar and Cylindrical Particles by the Indirect Transformation Method," J Appl Cryst, 1980, 13:577-584.
Golay et al., "Design and Validation of a Novel Generic Platform for the Production of Tetravalent IgG1-like Bispecific Antibodies," J Immunol, Apr. 1, 2016, 196 (7):3199-3211.
Grapentin et al., "Protein-Polydimethylsiloxane Particles in Liquid Vial Monoclonal Antibody Formulations Containing Poloxamer 188," J Pharm Sci, Aug. 2020, 109(8):2393-2404.
Hessell et al., "Fc receptor but not complement binding is important in antibody protection against HIV," Nature, Sep. 6, 2007, 449(7158):101-104.
Janeway et al., "The interaction of the antibody molecule with specific antigen," Immunobiology: The Immune System in Health and Disease, 2001, section 3.6, 5 pages.
Joshi et al., "Avoiding antibody aggregation during processing: establishing hold times," Biotechnol J, Sep. 2014, 9(9):1195-1205, doi: 10.1002/biot.201400052, Epub May 12, 2014.
Kraft et al., "Fc∈RI-Mediated Activation of Transcription Factors in Antigen-Presenting Cells," Int Arch Allergy Immunol, May 2001, 125(1):9-15.
Marme et al., "Intraperitoneal Bispecific Antibody (HEA125XOKT3) Therapy Inhibits Malignant Ascites Production in Advanced Ovarian Carcinoma," Int J Cancer, Sep. 10, 2002, 101(2):183-189.
Mazor et al., "Improving target cell specificity using a novel monovalent bispecific IgG design," mAbs, Mar./Apr. 2015, 7(2):377-389.
Muller et al., "The first constant domain ($C_H1$ and $C_L$) of an antibody used as heterodimerization domain for bispecific miniantibodies," FEBS Lett, Jan. 30, 1998, 422(2):259-264.
Ogiwara et al., "Anti FIXa/FX Bispecific Antibody (Emicizumab) Enhances Plasma Procoagulant Activity in Hemophilia B in the Presence of Very Low Level of Factor IX," Res Pract Thromb Haemost, 2017, 1.suppl 1:749.
Rajagopal et al., "Trehalose Limits Fragment Antibody Aggregation and Influences Charge Variant Formation in Spray-Dried Formulations at Elevated Temperatures," Mol Pharm, Jan. 7, 2019, 16(1):349-358, doi: 10.1021/acs.molphamiaceut.8b01002. Epub Dec. 17, 2018.
Tian et al., "In-depth analysis of subclass-specific conformational preferences of IgG antibodies," IUCrJ, Jan. 1, 2015, 2(Pt 1):9-18. doi: 10.1107/S205225251402209X. eCollection Jan. 1, 2015.
Yada et al., "Spotlight on emicizumab in the management of hemophilia A: patient selection and special considerations," J Blood Med, Jul. 2, 2019, 10:171-181.
U.S. Appl. No. 17/720,937, Igawa et al., filed Apr. 14, 2022.
U.S. Appl. No. 17/821,494, Igawa et al., filed Aug. 23, 2022.
U.S. Appl. No. 17/729,471, Igawa et al., filed Apr. 26, 2022.
U.S. Appl. No. 17/699,293, Hattori et al., filed Mar. 21, 2022.
U.S. Appl. No. 17/915,834, Sato et al., filed Sep. 29, 2022.

\* cited by examiner

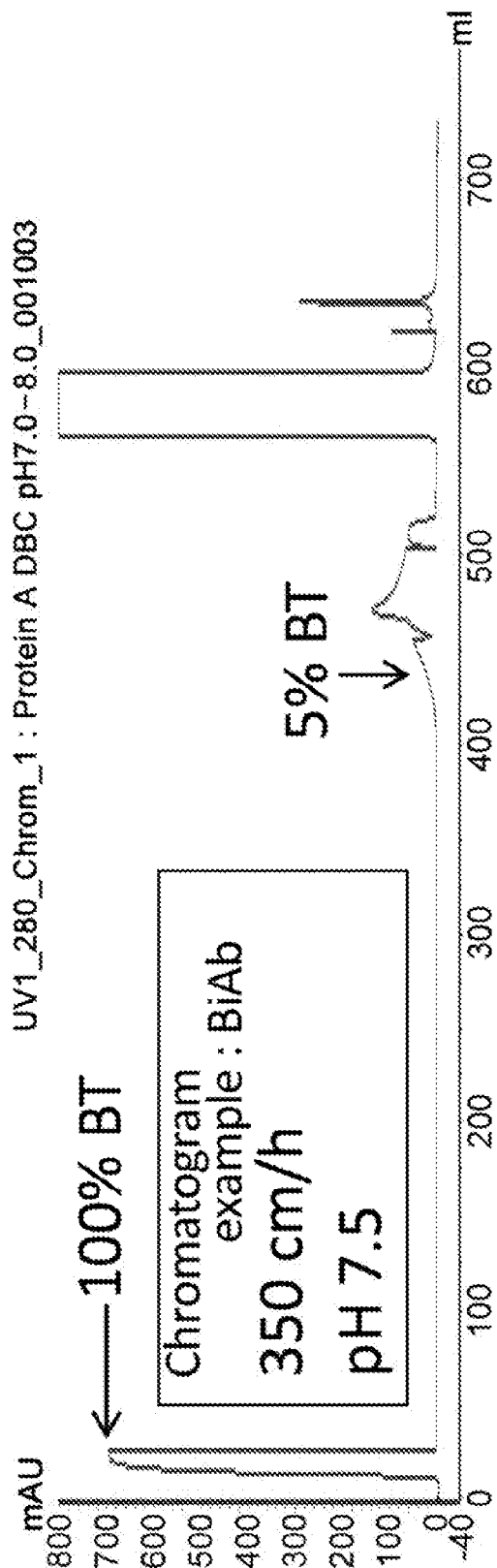

METHOD FOR PROMOTING EFFICIENCY OF PURIFICATION OF FC REGION-CONTAINING POLYPEPTIDE

CROSS-REFERENCE TO RELATED APPLICATIONS

This application is the National Stage of International Application Serial No. PCT/JP2016/088820, filed on Dec. 27, 2016, which claims the benefit of Japanese Application Serial No. 2015/255726, filed on Dec. 28, 2015.

TECHNICAL FIELD

The present invention relates to methods for increasing the dynamic binding capacity of an Fc region-containing polypeptide for a Protein A resin in Protein A column chromatography, purification methods that use such methods, and the like.

BACKGROUND ART

In the production of antibody pharmaceuticals, purification steps that use Protein A columns, ion exchange columns, and such, greatly affect the production efficiency (yield) of antibodies; therefore, it is desired that the efficiency of such steps be increased. Means for accomplishing the efficiency include the following two methods: (1) increasing the binding capacity per unit volume of resin; and (2) reducing the time required for purification by high-flow treatment.

Recently, the improvement of Protein A resins has advanced, and more antibodies can bind to Protein A resins, and accordingly, efficient antibody purification is being achieved. For example, for rProtein A sepharose Fast Flow manufactured by GE Healthcare, which is a typical first-generation Protein A resin, the ordinary antibody-binding capacity is 15 to 20 g/L resin; whereas, for the second-generation Protein A resin manufactured by the same company, Mab Select SuRe, which is currently most commonly used worldwide, the generally observed binding capacity is approximately 30 g/L resin. In addition, compared to the former resin, the latter can accommodate a linear flow rate approximately 1.5- to 2-times higher, and a more efficient Protein A purification of antibody molecules has been possible.

Bispecific antibodies have properties of recognizing two different types of antigens, and accordingly, they carry two types of H chains. Therefore, culture supernatants containing bispecific antibodies contain not only the bispecific antibodies comprising the two types of H chains, but also antibodies comprising only one type of H chain. To separate these antibodies from the bispecific antibodies, Fc region variants with modified binding activities to Protein A resins have been used (Patent Documents 1 and 2). It was concerned that such molecular modification could have an effect of decreasing the efficiency of Protein A purification of bispecific antibodies.

Under such circumstances, new means for performing more efficient bispecific antibody purification using Protein A resin columns have been desired.

CITATION LIST

Patent Documents

[Patent Document 1] US20100331527
[Patent Document 2] US20130018174

SUMMARY OF THE INVENTION

Problems to be Solved by the Invention

An objective of the present invention is to provide methods for efficiently purifying an Fc region-containing polypeptide, in particular a bispecific antibody, using a Protein A resin column.

Means for Solving the Problems

As a result of dedicated research to solve the above-mentioned problems, the present inventors discovered that, by preparing an Fc region whose first polypeptide chain and second polypeptide chain have binding activities to a Protein A resin that are different from each other, the dynamic binding capacity of the antibody is increased, and the antibody purification efficiency is increased, and completed the present invention.

Specifically, the present invention provides the following:
[1] a method for increasing the dynamic binding capacity of an Fc region-containing polypeptide for a Protein A resin in Protein A column chromatography;
[2] The method of [1], comprising the step of preparing a first polypeptide chain and a second polypeptide chain having binding activities to the resin that are different from each other, as the first polypeptide chain and the second polypeptide chain of the Fc region;
[3] The method of [1] or [2], comprising the steps of preparing a first polypeptide chain that binds to the resin as the first polypeptide chain of the Fc region, and preparing a second polypeptide chain that does not bind to the resin or shows weaker binding to the resin compared to the first polypeptide chain, as the second polypeptide chain of the Fc region;
[4] The method of any one of [1] to [3], comprising the step of modifying the Fc region of the Fc region-containing polypeptide so that the first polypeptide chain of the Fc region binds to the resin, and the second polypeptide chain of the Fc region does not bind to the resin or shows weaker binding to the resin compared to the first polypeptide chain;
[5] The method of any one of [1] to [4], wherein the first polypeptide chain of the Fc region comprises a CH3 of IgG1, IgG2, or IgG4, and the second polypeptide chain of the Fc region comprises a CH3 of IgG3;
[6] The method of any one of [1] to [5], wherein the amino acid at position 435 according to EU numbering in the first polypeptide chain of the Fc region is His, and the amino acid at position 435 according to EU numbering in the second polypeptide chain of the Fc region is Arg;
[7] The method of any one of [1] to [6], wherein the increase in the binding capacity is 5 g/L resin or more;
[8] The method of any one of [1] to [7], wherein the dynamic binding capacity after the increase is 45 g/L resin or more;
[9] The method of any one of [1] to [8], wherein the Fc region-containing polypeptide is an antibody;
[10] The method of [9], wherein the antibody is a bispecific antibody;
[11] A method for purifying an Fc region-containing polypeptide using the method of any one of [1] to [10];
[12] An Fc region-containing polypeptide purified by the method of [11];
[13] A Protein A resin bound by an Fc region-containing polypeptide, wherein the dynamic binding capacity of the Fc region-containing polypeptide for the Protein A resin in Protein A column chromatography is 45 g/L resin or more;

[14] An Fc region-containing polypeptide in which the dynamic binding capacity for a Protein A resin in Protein A column chromatography has been increased;

[15] A method for producing an Fc region-containing polypeptide using a Protein A resin, which comprises the steps of:

(a) preparing a first polypeptide chain and a second polypeptide chain of an Fc region having binding activities to said resin that are different from each other;

(b) comparing the dynamic binding capacity of the Fc region-containing polypeptide of step (a) for the Protein A resin in Protein A column chromatography with the dynamic binding capacity of an Fc region-containing polypeptide comprising two polypeptide chains having substantially the same binding activity to said resin for the Protein A resin in Protein A column chromatography;

(c) contacting a sample comprising a polypeptide comprising the first polypeptide chain of the Fc region and a polypeptide comprising the second polypeptide chain of the Fc region with said resin; and (d) collecting an Fc region-containing polypeptide binding to the resin and comprising a heterologous polypeptide which comprises the polypeptide comprising the first polypeptide chain of the Fc region and the polypeptide comprising the second polypeptide chain of the Fc region;

[16] The method of [15], wherein said step (a) is preparing a first polypeptide chain that binds to the resin as the first polypeptide chain of the Fc region, and preparing a second polypeptide chain that does not bind to the resin or shows weaker binding to the resin compared to the first polypeptide chain, as the second polypeptide chain of the Fc region;

[17] The method of [15] or [16], wherein said step (a) is modifying the Fc region of the Fc region-containing polypeptide for purification, so that the first polypeptide chain of the Fc region binds to the resin, and the second polypeptide chain of the Fc region does not bind to the resin or shows weaker binding to the resin compared to the first polypeptide chain;

[18] the method of any one of [15] to [17], wherein the sample in step (c) comprises a common L chain polypeptide that can provide binding ability for both a polypeptide comprising the first polypeptide chain of the Fc region and a polypeptide comprising the second polypeptide chain of the Fc region;

[19] the purification method of [11], wherein the Fc region-containing polypeptide is an antibody;

[20] the purification method of [19], wherein the antibody is a bispecific antibody;

[21] an antibody purified by the method of [19];

[22] a bispecific antibody purified by the method of [20]; and

[23] a column containing the resin of [13].

Effects of the Invention

The present invention provides methods for more efficient purification of Fc region-containing polypeptides, in particular bispecific antibodies, using Protein A resins.

BRIEF DESCRIPTION OF THE DRAWINGS

FIG. 1 shows a breakthrough curve chromatogram detecting proteins discharged from the column when a BiAb solution was continuously loaded onto a Protein A resin column.

MODE FOR CARRYING OUT THE INVENTION

Herein below, the present invention will be described in detail.

The Fc region-containing polypeptides to be used in the present invention may contain an antibody Fc region, and they include polypeptides formed by fusing an Fc region with another polypeptide, for example, antibodies.

"Polypeptides" of the present invention generally refers to peptides and proteins approximately ten amino acids or more in length. Furthermore, they are generally polypeptides derived from organisms, but are not particularly limited, and for example, they may be polypeptides comprising an artificially designed sequence. Furthermore, they may be any of naturally-occurring polypeptides, synthetic polypeptides, recombinant polypeptides, or such.

"Fc region" generally refers to the region comprising two polypeptide chains which consist of a hinge portion or a portion thereof, CH2 domain, and CH3 domain in an antibody molecule, but is not particularly limited thereto, and there are also cases where the hinge portion or portion thereof is not included. According to EU numbering by Kabat, a human IgG-class Fc region refers to, for example, the region from cysteine at position 226 to the C terminus, or from proline at position 230 to the C terminus, but not limited thereto. Furthermore, the human CH2 domain refers to positions 231 to 340 according to EU numbering by Kabat, and the human CH3 domain refers to positions 341 to 447 according to EU numbering by Kabat, but not limited thereto.

The Fc region may be obtained preferably by partially digesting IgG1, IgG2, IgG3, Fc region-containing monoclonal antibodies or such using a protease such as pepsin, and then re-eluting the fraction adsorbed onto protein A resins. The protease is not particularly limited as long as it can digest a full-length antibody so that Fab and F(ab')2 will be produced in a restrictive manner by appropriately setting the enzyme reaction conditions such as pH, and examples include pepsin and papain.

Examples of the Fc region include human IgG-type Fc, and for example, they may be any of the IgG1, IgG2, IgG3, and IgG4 isotypes.

The Fc region of the present invention comprises the first polypeptide chain and the second polypeptide chain mentioned above.

An embodiment of the present invention is a method for increasing the dynamic binding capacity of an Fc region-containing polypeptide for a Protein A resin in Protein A column chromatography. The first polypeptide chain and the second polypeptide chain comprised in the Fc region preferably have binding activities to the Protein A resin that are different from each other. For example, when using a polypeptide chain that binds to a Protein A resin as the first polypeptide chain, a polypeptide chain that does not bind to or shows weaker binding to the Protein A resin compared to the first polypeptide chain can be used as the second polypeptide chain. As the first polypeptide chain, a polypeptide chain comprising the CH3 of IgG1, IgG2, or IgG4 may be used, and as the second polypeptide chain, a polypeptide chain comprising the CH3 of IgG3 may be used. In this case, IgG1, IgG2, IgG3, and IgG4 may be naturally-occurring, or they may include mutations within a range that allows the objective of the present invention to be accomplished. Furthermore, as the first polypeptide chain, a polypeptide chain in which position 435 according to EU numbering is His (H) can be used. As the second polypeptide chain, a polypeptide chain in which position 435 according to EU numbering is Arg (R) can be used. Furthermore, a polypeptide chain in which positions 435 and 436 according to EU numbering are His (H) and Tyr (Y), respectively, can be used as the first polypeptide chain. A polypeptide chain in which positions 435 and 436 according to EU numbering are Arg (R) and Phe (F), respectively, can be used as the second polypeptide chain. The positions other than position 435 or 436 according to EU numbering may be the same as or different from those of the naturally-occurring IgGs.

In this embodiment, increasing the dynamic binding capacity of an Fc region-containing polypeptide for the resin in Protein A column chromatography can be accomplished by modifying the Fc region of the Fc region-containing polypeptide that binds to the resin, so that the binding activities of the first polypeptide chain of the Fc region and the second polypeptide chain of the Fc region to the resin will be different from each other.

In another embodiment of the present invention, increasing the dynamic binding capacity of an Fc region-containing polypeptide for the resin in Protein A column chromatography can be accomplished by modifying the Fc region of the Fc region-containing polypeptide that binds to the resin, so that the first polypeptide chain of the Fc region binds to the resin, but the second polypeptide chain of the Fc region does not bind to the resin or shows weaker binding to the resin compared to the first polypeptide chain.

Examples of the modification include, but are not limited to, modifications performed so that the first and second polypeptide chains of the Fc region will contain CH3 regions such as those mentioned above, for example, modifications performed so that the above-mentioned specific amino acid resides at specified positions are contained.

On the other hand, the regions other than the Fc region in the Fc region-containing polypeptides used in the present invention may be in a homologous or heterologous form.

The homologous form has one or two or more, uniform or the same antigen-binding activities (i.e., when the Fc region-containing polypeptide is an antigen-binding molecule, it refers to an antigen-binding molecule having one or two or more, uniform or the same antigen-binding activity, which is, for example, an IgG-type antibody having two identical antigen-binding sites).

The heterologous form preferably has different antigen-binding activities (i.e., the Fc region-containing polypeptide is a bispecific antigen-binding molecule, for example, a bispecific antibody). When the Fc region-containing polypeptide used in the present invention is a bispecific antibody, while the H chains may be heterologous, the L chains may be common L chains, and the common L chains preferably provide binding abilities for both H chains. When the bispecific antibody is an IgG-type antibody, it is composed of two heterologous H chains and two identical common L chains.

Binding capacities include static binding capacity (SBC) and dynamic binding capacity (DBC). Static binding capacity refers to the upper limit of the amount of polypeptides that a resin can adsorb, and dynamic binding capacity refers to the degree to which polypeptides can be collected when a polypeptide-containing solution is flowing through the column. A resin having a large dynamic binding capacity allows efficient polypeptide adsorption even under high linear flow rate, and polypeptide purification can be accomplished in a short time.

For example, dynamic binding capacity (DBC) can be determined by the following method. First, a column loaded with a resin is placed in a chromatography apparatus, and a polypeptide-containing sample solution is allowed to flow through the column at a specified linear flow rate. Then, the absorbance of the eluate is measured, and DBC is determined by identifying the mass of the added polypeptide when breakthrough (BT) for a specified proportion (for example, 5%) of absorbance of the added sample solution is measured.

The following apparatus and such can be used for the DBC calculation:
LC apparatus: AKTAAVANT25 manufactured by GE Healthcare
Software: Unicorn version 6.1 manufactured by GE Healthcare
Protein A resin: Mab Select SuRe (Cat No. 17-5438-05) or Hitrap Mab Select SuRe (Cat No. 11-0034-93) manufactured by GE Healthcare
Buffers:
equilibration/preliminary washing—20 mmol/L Na-phosphate, pH 7.5
elution—50 mmol/L Acetic acid
regeneration—0.1 mol/L NaOH
The method for calculating the DBC can be carried out as follows.

The above-mentioned apparatus, software, and resins are used, and by performing the chromatography operation by the following procedure, the DBC is calculated. A calculation method when using 5% BT as the indicator is shown below.

(1) The load fraction (IgG concentration: P g/L) is allowed to flow through the LC apparatus without passing it through the column, and the value of $OD_{280\ nm}$ for 100% leakage (=100% BT) was confirmed. This value is denoted as a.

(2) The value obtained by multiplying 0.05 to a is defined as the $OD_{280\ nm}$ at 5% BT. This value is denoted as $b_{5\%}$.

(3) The load fraction is allowed to flow continuously through a set amount of equilibrated resin (r L), and when the $OD_{280\ nm}$ value reaches $b_{5\%}$, the volume of the load fraction is read from the chromatogram. This value is denoted as $c_{5\%}$ L.

(4) The value obtained by the equation $(P \times c_{5\%})/r$ is calculated as $DBC_{5\%}$ which is the dynamic binding capacity at 5% BT.

$$DBC_{5\%} = (P \times c_{5\%})/r (\text{unit:g/L resin})$$

When determining $DBC_{10\%}$, the calculation is possible by determining $c_{10\%}$ in a similar manner.

In an embodiment of the present invention, the increase in the dynamic binding capacity of an Fc region-containing polypeptide for a Protein A resin in Protein A column chromatography is at least 5 g/L resin, preferably 10 g/L resin or more, 15 g/L resin or more, 20 g/L resin or more, and 25 g/L resin or more, when taking 5% BT as the standard.

In a specific embodiment of the present invention, the increase in the dynamic binding capacity of an Fc region-containing polypeptide for a Protein A resin in Protein A column chromatography is at least 5 g/L resin, preferably 10 g/L resin or more, 15 g/L resin or more, 20 g/L resin or more, and 25 g/L resin or more, at contact time of 3.4 minutes, when taking 5% BT as the standard.

In an embodiment of the present invention, according to the method of the present invention, the dynamic binding capacity of an Fc region-containing polypeptide for a Protein A resin in Protein A column chromatography is at least 45 g/L resin or more, preferably 50 g/L resin or more, 55 g/L resin or more, and 60 g/L resin or more, when taking 5% BT as the standard.

In a specific embodiment of the present invention, according to the method of the present invention, the dynamic binding capacity of an Fc region-containing polypeptide for a Protein A resin in Protein A column chromatography is at least 50 g/L resin or more, preferably 51 g/L resin or more, 52 g/L resin or more, 53 g/L resin or more, 54 g/L resin or more, and 55 g/L resin or more, at contact time of 3.4 minutes, when taking 5% BT as the standard.

In one embodiment of the present invention, the Fc region-containing polypeptide may be a polypeptide in which an Fc region is linked to another protein, bioactive peptide, or such. Examples of other proteins and bioactive peptides include receptors, adhesion molecules, ligands (cytokines, chemokines, and such), and enzymes, but are not limited thereto. They may be blood coagulation factors, and examples include FIX, FIXa, and FX.

In one embodiment of the present invention, the Fc region-containing polypeptide may be an immunoadhesin.

In another embodiment of the present invention, the Fc region-containing polypeptides may be antibodies. Antibodies of the present invention are not particularly limited, as long as they bind to antigens of interest, and they may be polyclonal or monoclonal antibodies. Monoclonal antibodies are preferred because they can be stably produced as homogeneous antibodies.

The monoclonal antibodies used in the present invention include not only those derived from animals such as humans, mice, rats, hamsters, rabbits, sheep, camels, and monkeys, but also artificially modified, gene recombinant antibodies such as chimeric antibodies, humanized antibodies (also referred to as reshaped human antibodies), and bispecific antibodies. Furthermore, they also include gene recombinant antibodies produced by artificially modifying the antibody constant region and such to alter the physical properties of the antibody molecule, specifically, alteration of the isoelectric point (pI), modification of affinity for Fc receptor, etc., for the purpose of improving retention in blood and in vivo kinetics.

The immunoglobulin class of the antibodies used in the present invention is not particularly limited; and the class may be any class, including IgG such as IgG1, IgG2, IgG3, and IgG4, IgA, IgD, IgE, and IgM. However, IgG is preferred.

The antibodies used in the present invention also include not only whole antibodies but also antibody fragments such as Fv, Fab, and F(ab)2, and minibodies (low molecular weight antibodies) such as monovalent or bivalent or higher valency single-chain Fv formed by linking antibody variable regions via a linker such as a peptide linker (scFv, sc(Fv)2, diabodies such as scFv dimer, etc).

The above-described antibodies used in the present invention can be prepared by methods well known to those skilled in the art.

Basically, monoclonal antibody-producing hybridomas can be prepared using known techniques as described below. Specifically, immunization is carried out according to a conventional immunization method using a desired antigen or cells expressing the desired antigen as a sensitizing antigen. The yielded immunocytes are fused with known parental cells by a conventional cell fusion method. The fused cells are screened for monoclonal antibody-producing cells (hybridomas) by conventional screening methods to produce the hybridomas. Hybridomas can be produced, for example, according to the method by Milstein et al. (Kohler, G. and Milstein, C., Methods Enzymol. (1981) 73:3-46).

Amino acid residues can be modified by modifying one or more bases in a DNA encoding a polypeptide and expressing the DNA in a host cell, as described below. Those skilled in the art can easily determine the number, positions, and types of nucleotides that should be modified depending on the types of amino acid residues after the modification.

In the present invention, "modification" refers to substitution, deletion, addition, insertion, or a combination thereof.

Antibodies used in the present invention can also include additional alterations, besides the above-mentioned amino acid sequence modifications. The additional modifications can be selected from any of amino acid substitution, deletion, and modification, or a combination thereof. Specifically, polypeptides containing the following modifications in their amino acid sequences are all included in the present invention:

amino acid modifications for increasing the rate of heterologous association of two types of H chains of a bispecific antibody;

amino acid modifications for stabilizing a disulfide bond formed between a first polypeptide having antigen-binding activity and a second polypeptide with or without antigen-binding activity;

amino acid modifications for improving antibody retention in plasma;

modifications for improving the stability under acidic conditions;

modifications for decreasing the heterogeneity;

modifications for suppressing deamidation reactions;

modifications for introducing a difference in the isoelectric points between two types of polypeptides; and modifications for changing the affinity towards an Fcγ receptor.

Methods for obtaining human antibodies are also known. For example, desired human antibodies having antigen-binding activity can be obtained by sensitizing human lymphocytes with an antigen of interest or cells expressing an antigen of interest in vitro; and fusing the sensitized lymphocytes with human myeloma cells. Alternatively, desired human antibodies can also be obtained by immunizing transgenic animals having the entire repertoire of human antibody genes with an antigen. Furthermore, techniques for obtaining human antibodies by panning using a human antibody library are known. For example, the variable regions of human antibodies can be expressed as single-chain antibodies (scFvs) on the surface of phages using a phage display method, and then phages that bind to the antigen can be selected to obtain human antibodies. The antibodies used in the present invention also include such human antibodies.

When the antibody genes are isolated and introduced into appropriate hosts to produce antibodies, hosts and expression vectors can be used in appropriate combinations. When eukaryotic cells are used as a host, animal cells, plant cells, and fungal cells can be used. The animal cells include mammalian cells such as CHO, COS, myeloma, baby hamster kidney (BHK), HeLa, and Vero cells. Antibodies can be obtained by introducing the antibody genes of interest into these cells by transformation and then culturing the transformed cells in vitro.

The antigen of the antibody used in the present invention is not particularly limited, and it may be any antigens. Examples of antigens preferably include ligands (cytokines, chemokines, and such), receptors, cancer antigens, MHC antigens, differentiation antigens, immunoglobulins, and immune complexes partly containing immunoglobulins. Examples include blood coagulation factors such as FIX, FIXa, and FX.

For collection of expression products, the medium is collected when the polypeptides are secreted into the medium. When the polypeptides are produced within cells, the cells are dissolved, and then the polypeptides are collected.

The polypeptides can be collected and purified from recombinant cell cultures by using known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. In the present invention, Protein A affinity chromatography is preferred. Herein, purification methods using a column, separation methods using a column, and chromatography may be used synonymously. Examples of columns that use Protein A resins include POROS A (manufactured by Applied Biosystems), rProtein A Sepharose F. F. (manufactured by GE), ProSep vA (manufactured by Millipore), but are not limited thereto. Furthermore, resins to which ligands produced by modifying the amino acid sequence of intact Protein A, and such, can be used for Protein A affinity chromatography. When such modified Protein A resins are used, amino acid modifications of the present invention produce differences in the binding activities, and polypeptide multimers of interest can be separated and purified. Examples of resins to which modified Protein A are bound include mabSelect SuRE (manufactured by GE Healthcare) and Hitrap MabSelect Sure (manufactured by GE Healthcare), but are not limited thereto. Herein, a column packed with a Protein A resin, a column that uses a Protein A resin, a Protein A resin column, and a Protein A column are synonymous. Furthermore, a purification method that uses a Protein A resin and a purification method that uses a Protein A column may also be used synonymously.

An embodiment of the present invention is a method for purifying an Fc region-containing polypeptide which uses the method for increasing dynamic binding capacity of an Fc region-containing polypeptide for a Protein A resin in Protein A column chromatography. More specifically, an embodiment is a method for purifying an antibody, and another embodiment is a method for purifying a bispecific antibody.

Another embodiment of the present invention is an Fc region-containing polypeptide purified by the above-mentioned purification method. More specifically, an embodiment is an antibody purified by the above-mentioned purification method, and another embodiment is a bispecific antibody purified by the above-mentioned purification method.

Furthermore, another embodiment of the present invention is a Protein A resin to which an Fc region-containing polypeptide is bound at 45 g/L resin or more, when taking 5% BT as the standard; and a column containing the resin. The dynamic binding capacity of the Fc region-containing polypeptide for the resin and the column containing the resin is preferably 50 g/L resin or more, 55 g/L resin or more, 60 g/L resin or more, and 65 g/L resin or more, when taking 5% BT as the standard.

Furthermore, a specific embodiment of the present invention is a Protein A resin to which an Fc region-containing polypeptide is bound, where the dynamic binding capacity of the Fc region-containing polypeptide for a Protein A resin in Protein A column chromatography is 50 g/L resin or more at contact time of 3.4 minutes, when taking 5% BT as the standard; and a column containing the resin. The dynamic binding capacity of the Fc region-containing polypeptide for the resin and the column containing the resin is preferably 51 g/L resin or more, 52 g/L resin or more, 53 g/L resin or more, 54 g/L resin or more, and 55 g/L resin or more, at contact time of 3.4 minutes, when taking 5% BT as the standard.

An embodiment of the present invention is an Fc region-containing polypeptide having an increased dynamic binding capacity for a Protein A resin in Protein A column chromatography. More specifically, in one embodiment, the Fc region-containing polypeptide is an antibody, and in another embodiment, the Fc region-containing polypeptide is a bispecific antibody.

In an embodiment of the present invention, the increase in the dynamic binding capacity of the Fc region-containing polypeptide for a Protein A resin in Protein A column chromatography is, when taking 5% BT as the standard, at least 5 g/L resin, preferably 10 g/L resin or more, 15 g/L resin or more, 20 g/L resin or more, and 25 g/L resin or more.

In a specific embodiment of the present invention, the increase in the dynamic binding capacity of the Fc region-containing polypeptide for a Protein A resin in Protein A column chromatography is, when taking 5% BT as the standard, at least 5 g/L resin, preferably 10 g/L resin or more, 15 g/L resin or more, 20 g/L resin or more, and 25 g/L resin or more, at contact time of 3.4 minutes.

In the Fc region-containing polypeptide having an increased dynamic binding capacity for a Protein A resin in Protein A column chromatography, it is preferred that a first polypeptide chain and a second polypeptide chain contained in the Fc region have different binding activities for the Protein A resin. For example, when using a polypeptide chain that binds to the Protein A resin as the first polypeptide chain, a polypeptide chain that does not bind to the Protein A resin or binds weakly to the Protein A resin compared to the first polypeptide may be used as the second polypeptide chain. As the first polypeptide chain, a polypeptide chain comprising the CH3 of IgG1, IgG2, or IgG4 may be used. As the second polypeptide chain, a polypeptide chain comprising the CH3 of IgG3 may be used. In this case, naturally-occurring IgG1, IgG2, IgG3, and IgG4 may be used, or they may contain mutations within a range that allows the objectives of the present invention to be accomplished. Furthermore, as the first polypeptide chain, a polypeptide chain in which position 435 according to EU numbering is His (H) can be used. As the second polypeptide chain, a polypeptide chain in which position 435 according to EU numbering is Arg (R) can be used. Furthermore, a polypeptide chain in which positions 435 and 436 according to EU numbering are His (H) and Tyr (Y), respectively, can be used as the first polypeptide chain. A polypeptide chain in which positions 435 and 436 according to EU numbering are Arg (R) and Phe (F), respectively, can be used as the second polypeptide chain. The positions other than position 435 or 436 according to EU numbering may be the same as those of the naturally-occurring IgG, or different from those of the naturally-occurring IgGs.

An embodiment of the present invention is a method for producing an Fc region-containing polypeptide using a Protein A resin, which comprises the steps of:

(a) preparing a first polypeptide chain and a second polypeptide chain of an Fc region, which have binding activities to the resin that are different from each other;

(b) comparing the dynamic binding capacity of the Fc region-containing polypeptide of step (a) for the Protein A resin in Protein A column chromatography with the dynamic binding capacity of an Fc region-containing polypeptide comprising two polypeptide chains having substantially the same binding activities to the resin for the Protein A resin in Protein A column chromatography;

(c) contacting a sample comprising a polypeptide comprising the first polypeptide chain of the Fc region and a polypeptide comprising the second polypeptide of the Fc region with the resin; and (d) collecting an Fc region-containing polypeptide comprising a heterologous polypeptide which comprises the polypeptide comprising the first polypeptide chain of the Fc region and the polypeptide comprising the second polypeptide of the Fc region.

The above-mentioned step (a) may be a step of preparing a first polypeptide chain that binds to the resin as the first polypeptide chain of the Fc region, and preparing a second polypeptide chain that does not bind to or shows weaker binding to the resin (compared to binding of the aforementioned first polypeptide chain to the resin) as the second polypeptide chain of the Fc region. Furthermore, the above-mentioned step (a) may be a step of modifying the Fc region of the Fc region-containing polypeptide, which is the target of purification, so that the first polypeptide chain of the Fc region binds to the resin, but the second polypeptide chain of the Fc region does not bind to or shows weaker binding to the resin (compared to binding of the aforementioned first polypeptide chain to the resin). The modification is not particularly limited as long as it is a modification for obtaining an Fc region having the above-described features, and examples include modifying the first polypeptide chain to be a polypeptide chain comprising the CH3 of IgG1, IgG2, or IgG4, and modifying the second polypeptide chain to be a polypeptide chain comprising the CH3 of IgG3. Examples of such modifications include modifying position 435 according to EU numbering in the first polypeptide chain to be His, and position 435 according to EU numbering in the second polypeptide chain to be Arg. Examples of other modifications include modifying positions 435 and 436 according to EU numbering of the first polypeptide chain to be His (H) and Tyr (Y), respectively, and positions 435 and 436 according to EU numbering of the second polypeptide chain to be Arg (R) and Phe (F), respectively. The positions other than position 435 or 436 according to EU numbering may be the same as or different from those of the naturally-occurring IgGs.

In the above-mentioned step (b), the two polypeptide chains may be any polypeptide chains as long as their binding activities to the resin are substantially the same, and the homology between the two polypeptide chains may be high or low. For example, "an Fc region-containing polypeptide comprising two polypeptide chains having substantially the same binding activities to the resin" is an Fc region-containing polypeptide comprising two of the first polypeptide chains, or an Fc region-containing polypeptide comprising two of the second polypeptide chains. Furthermore, examples of two polypeptide chains having substantially the same binding activities to a Protein A resin include: two polypeptides chains which are polypeptide chains each comprising any of the CH3 of IgG1, IgG2, or IgG4; two polypeptides chains which are polypeptide chains each comprising the CH3 of IgG3; two polypeptide chains in which position 435 according to EU numbering in the polypeptide chains are both His (H) or both Arg (R); two polypeptide chains both of which are polypeptide chains in which positions 435 and 436 according to EU numbering are His (H) and Tyr (Y), respectively; two polypeptide chains both of which are polypeptide chains in which positions 435 and 436 according to EU numbering are Arg (R) and Phe (F), respectively.

"Substantially the same" means being not necessarily completely identical as long as this is within a range that can accomplish the objectives of the present invention, and the meaning includes being the "same".

In one embodiment of the present invention, "comparing" in the above-mentioned step (b) may be a step of "confirming the elevated" dynamic binding capacity of the Fc region-containing polypeptide of step (a) for a Protein A resin in Protein A column chromatography compared with the dynamic binding capacity of an Fc region-containing polypeptide comprising two polypeptide chains having substantially the same binding activities to the resin for the Protein A resin in Protein A column chromatography.

By comparing or confirming the dynamic binding capacity, one can know the maximum amount of antibodies that can be loaded onto the Protein A resin column when producing the antibodies, and this enables efficient antibody production.

The sample described in the above-mentioned step (c) may comprise two different L chain polypeptides, or common L chain polypeptides that can provide binding ability to both the H chain of the polypeptide comprising the first polypeptide chain of the Fc region and the H chain of the polypeptide comprising the second polypeptide chain of the Fc region.

In an embodiment of the present invention, in the above-mentioned method for purifying an Fc region-containing polypeptide, the Fc region-containing polypeptide is an antibody, and in another embodiment the Fc region-containing polypeptide is a bispecific antibody.

The aforementioned steps (a) to (d) do not have to be performed in this order, and each step may be included multiple times.

An embodiment of the present invention is a method for purifying an Fc region-containing polypeptide using a Protein A resin, which comprises the steps of (a) to (d) above.

All patents and reference documents explicitly cited herein are incorporated by reference into this specification in their entirety.

The present invention will be further illustrated by the following Examples, but the technical scope of the present invention is not to be construed as being limited thereto.

EXAMPLES

[Example 1] Preparation of Antibody Gene Expression Vectors and Expression of Each Antibody In the Examples, the anti-FIXa/FX bispecific antibody (H1 chain/H2 chain/L chain: SEQ ID NOs: 1/2/3) having activity of substituting for FVIII function, which is described in WO2012/067176, was used (herein below, this is referred to as "BiAb", which is a so-called heterologous antibody). The BiAb comprises four chains consisting of three types of chains. The four chains consist of an H1 chain and an H2 chain which are two types of H chains, and two common L chains which are one type of L chain. This antibody was obtained by the method described in WO2012/067176. An antibody gene was inserted into an animal cell expression vector. By transfecting CHO cells with the vector, the bispecific antibody was expressed. Furthermore, "Q homo" comprising the two L chains and the two H1 chains, and "J homo" comprising the two L chains and the two H2 chains were obtained by the above method.

This antibody is IgG4-type, and His at position 435 according to EU numbering in the Fc region of the H1 chain has been substituted with Arg. This substitution weakens or eliminates the binding activity of the Fc region for the Protein A resin.

[Example 2] Method for Evaluating the Dynamic Binding Capacity (DBC)

Generally, DBC is determined by depicting the behavior in which the continuously loaded protein is discharged from the column as a breakthrough curve (hereinafter, "BTC") in a chromatogram by UV monitoring using a purification device connected to a UV detector. The BTC chromatogram when using BiAb is shown in FIG. 1 as an example.

The DBC was evaluated by comparing the amount of load at the 5% breakthrough point (BT point) among the antibody molecules and their mixtures.

The following apparatus and such were used for the DBC calculations:

LC apparatus: AKTAAVANT25 manufactured by GE Healthcare

Software: Unicorn version 6.1 manufactured by GE Healthcare

Protein A resin: Mab Select SuRe (Cat No. 17-5438-05) or Hitrap Mab Select SuRe (Cat No. 11-0034-93) manufactured by GE Healthcare Buffers:
equilibration/preliminary washing—20 mmol/L Na-phosphate, pH 7.5
elution—50 mmol/L Acetic acid
regeneration—0.1 mol/L NaOH The method for calculating the DBC was carried out as follows.

The above-mentioned apparatus, software, and resins were used, and the DBC was calculated by performing the chromatography operation as follows.

(1) The load fraction (IgG concentration: P g/L) was once allowed to flow through the LC apparatus without passing it through the column, and the value of $OD_{280\ nm}$ for 100% leakage (=100% BT) was confirmed. This value was denoted as a.

(2) The value obtained by multiplying 0.05 and a was defined as the $OD_{280\ nm}$ at 5% BT. This value was denoted as $b_{5\%}$.

(3) The load fraction was allowed to flow continuously through a set amount equilibrated resin (r L), and when the $OD_{280\ nm}$ value reached $b_{5\%}$, the volume of the load fraction was read from the chromatogram. This value was denoted as $c_{5\%}$ L.

(4) The value obtained by the equation $(P \times c_{5\%})/r$ was calculated as $DBC_{5\%}$ which is the dynamic binding capacity at 5% BT.

$$DBC_{5\%} = (P \times c_{5\%})/r \text{(unit:g/L resin)}$$

When determining $DBC_{10\%}$, calculations were carried out by determining $c_{10\%}$ in the same manner.

[Example 3] DBC for Each Antibody Molecule Alone

The DBC of each of Q homo, J homo, and BiAb was determined under the following conditions:

Column: Hitrap MabSelect Sure (hereinafter, referred to as MSS) (GE Healthcare), 0.7×2.5 cm Load material: material mimicking the IgG concentration, pH, and conductivity of actual load CM, using each purified antibody standard. IgG concentration: approximately 2 g/L; pH7.5; conductivity: 1.2 S/m. J homo with a purity of approximately 80%, Q homo with a purity of approximately 85%, and BiAb with a purity of approximately 95% were used.

Contact time: 3.4 min (43.75 cm/h)

The results are shown in Table 1.

TABLE 1

| IgG | 5% BT g/L resin |
|---|---|
| BiAb | 58.0 |
| J Homo | 32.8 |
| Q Homo | 31.2 |

The results showed that the DBC of BiAb is significantly higher than the DBC of J homo and Q homo.

[Example 4] Verification of pH and Contact Time for the DBC of BiAb

Next, the DBC of BiAb alone when changing pH of the load solution and the contact time on the resin was confirmed, and the effects of both of the parameters were verified. The conditions are shown below:

Column: MabSelect Sure (GE Healthcare), 1.0×20 cm

Load material: a diluted preparation of a purified BiAb standard mimicking CM (BiAb: 95%): 2 g/L; pH 6.5-8.0 (verification); Conductivity: 1.2 S/m Contact time: 3-8 min (verification)

The results are shown in Table 2.

TABLE 2

| 5% BT g/L resin | 150 cm/h 8 min | 350 cm/h 3.4 min | 400 cm/h 3 min |
|---|---|---|---|
| pH 6.5 | Not tested | 55.5 | Not tested |
| pH 7.0 | Not tested | 54.2 | Not tested |
| pH 7.5 | 63.2 | 52.3 | 49.2 |
| pH 8.0 | Not tested | 51.7 | Not tested |

[Example 5] the DBC in a Mixture of BiAb and Homo

In the culture supernatant actually loaded onto the Protein A resin (hereinafter, "HCCF"), BiAb, J homo, and Q homo are present as a mixture. More specifically, from the viewpoint of recovering BiAb which is the substance of interest, J homo and Q homo can be regarded as substances that compete with BiAb. Therefore, when considering actual production, the verification of the DBC of BiAb under conditions where certain amounts of J homo and Q homo are present in HCCF is meaningful. For this verification, experiments were carried out under the following conditions:

Column: Hitrap MabSelect Sure (MSS) (GE Healthcare), 0.7×2.5 cm

Load Material: a mixture of purified BiAb and Homo standards mimicking CM: 2 g/L; pH 7.5; Cond: 1.2 S/m

| Control BiAb (95%) | J homo:BiAb:Q homo = 5:95:0 |
| Mimic A | J homo:BiAb:Q homo = 10:83:7 |
| Mimic B | J homo:BiAb:Q homo = 10:68:22 |

Contact time: 3.4 min (43.75 cm/h)

The load of BTC was fractioned, and the BiAb/Homo ratio at each of the BT points was confirmed by Analytical CIEC.

Conditions of Analytical CIEC were as follows:
HPLC apparatus: Alliance 2695/2487 manufactured by Waters
Software: Empower3 manufactured by Waters
CIEC column: ProPac WCX-10, Product No. 054993 manufactured by Thermo scientific
Column temperature: 30° C.
Amount injected: 30 μg/shot
Buffers:
Mobile phase A—9.6 mmol/L Tris, 6.0 mmol/L piperazine, 11.0 mmol/L imidazole, pH 6.0
Mobile phase B—9.6 mmol/L Tris, 6.0 mmol/L piperazine, 11.0 mmol/L imidazole, 150 mmol/L NaCl, pH 10.1
Gradient conditions:

| Time (min) | Flow rate (mL/min) | % A | % B |
|---|---|---|---|
| 0.0 | 1.0 | 100 | 0 |
| 1.0 | 1.0 | 100 | 0 |
| 20.0 | 1.0 | 0 | 100 |
| 35.0 | 1.0 | 0 | 100 |

The results are shown in Table 3

TABLE 3

| Sample | | 5% BT | 10% BT | 15% BT | 20% BT |
|---|---|---|---|---|---|
| Control BiAb 95% | g/L resin J:BiAb:Q | 58.0 4:96:0 | — | — | — |
| Mimic A | g/L resin J:BiAb:Q | 51.0 5:55:40 | 58.2 5:55:40 | 63.1 5:57:38 | 65.5 6:59:36 |
| Mimic B | g/L resin J:BiAb:Q | 38.8 0:3:97 | 42.8 0:3:97 | 45.9 0:2:98 | — |

The following was found from the above results.
DBC: J homo≈Q homo<BiAb
Affinity to MSS: Q homo<BiAb<J homo
Effects of the parameters on BiAb DBC:
pH: In the range of pH 6.5 to 8.0, while lower pH tended to yield higher DBC, the impact was small.
Contact time: In the range of three to eight minutes, while longer contact time tended to yield higher DBC, the DBC was not less than those of Q homo and J homo even at three minutes.
Regarding the affinity to MSS, the results reflected the features of the present invention, and it is manifested by the order of leakage in Example 5
On the other hand, regarding DBC, it is presumed that the differences in the affinity to the MSS resin and the availability of the ligand produced the results. More specifically, since J homo has two sequences where it binds strongly to the MSS ligand, it is bound to the MSS resin at the two sites. That is, the MSS ligands present in the area that is spatially occupied by J homo cannot be used. On the other hand, since BiAb has only one site with a sequence that strongly binds to MSS, it has spatial freedom higher than J homo, and high DBC could be realized by effective utilization of more MSS ligands. The reason why Q homo has a low DBC would be simply that the binding activity of the molecule as the whole is low. Furthermore, it is thought that Q homo and J homo competitively inhibit the binding of BiAb to MSS.

The invention claimed is:

1. A method for producing a protein comprising a heterodimeric Fc region with an increased dynamic binding capacity for a Protein A resin in Protein A column chromatography, compared to the dynamic binding capacity for the Protein A resin of a homodimeric Fc region, the method comprising:
   (a) preparing a heteromultimer protein comprising
      (i) a first polypeptide chain comprising a first human IgG Fc region that binds to the resin, and
      (ii) a second polypeptide chain comprising a second human IgG Fc region different from the first Fc region, wherein the second Fc region does not bind to the resin, or binds more weakly to the resin compared to the first Fc region; and
   (b) measuring the heteromultimer protein's dynamic binding capacity for the resin in Protein A column chromatography, wherein the heteromultimer protein has an increased dynamic binding capacity for the resin in Protein A column chromatography compared to the dynamic binding capacity for the resin in Protein A column chromatography of a protein containing two copies of the first Fc region.

2. The method of claim 1, wherein the first Fc region comprises a CH3 region of human IgG1, human IgG2, or human IgG4, and the second Fc region comprises a CH3 region of human IgG3.

3. The method of claim 1, wherein the first Fc region comprises a His residue at EU numbering position 435, and the second Fc region comprises an Arg residue at EU numbering position 435.

4. The method of claim 1, wherein the heteromultimer protein and the protein containing two copies of the first Fc region are both antibodies.

5. The method of claim 4, wherein the heteromultimer protein is a bispecific antibody.

6. The method of claim 1, wherein the heteromultimer protein's dynamic binding capacity for the resin in Protein A column chromatography is at least 5 g/L resin greater than that of the protein containing two copies of the first Fc region.

7. The method of claim 1, wherein the heteromultimer protein's dynamic binding capacity for the resin in Protein A column chromatography is at least 45 g/L resin at 5% breakthrough.

8. A method for producing a protein having an increased dynamic binding capacity for a Protein A resin in Protein A column chromatography, compared to the dynamic binding capacity for the Protein A resin of a starting protein, the method comprising:
(a) identifying a starting protein comprising a first polypeptide chain and a second polypeptide chain, each chain comprising a human IgG Fc region that binds to the Protein A resin;
(b) preparing a variant protein comprising the first polypeptide chain and a third polypeptide chain identical to the second polypeptide chain except for one or more Fc region alterations that reduce or eliminate the ability of the third polypeptide chain's Fc region to bind to Protein A resin;
(c) measuring the variant protein's dynamic binding capacity on a Protein A chromatography column; and
(d) determining that the variant protein's dynamic binding capacity on the Protein A chromatography column is higher than the starting protein's dynamic binding capacity on the Protein A chromatography column.

9. The method of claim 8, wherein the human IgG Fc region of the second polypeptide chain is a human IgG1, IgG2, or IgG4 Fc region, and the one or more Fc region alterations comprise replacing that human IgG Fc region with a human IgG3 Fc region.

10. The method of claim 8, wherein the human IgG Fc region of the second polypeptide chain comprises a His residue at EU numbering position 435, and the one or more Fc region alterations comprise replacing that His residue at EU numbering position 435 with an Arg residue at EU numbering position 435 in the third polypeptide chain.

11. A method for purifying an Fc region-containing protein, the method comprising:
(a) preparing a first protein comprising
(i) a first polypeptide chain comprising a first Fc region that binds to a Protein A resin, and
(ii) a second polypeptide chain comprising a second Fc region that does not bind to the resin or binds to the resin more weakly than does the first Fc region;
(b) measuring the first protein's dynamic binding capacity for the Protein A resin in Protein A column chromatography;
(c) determining that the dynamic binding capacity measured in step (b) is greater than the dynamic binding capacity of a second protein for the Protein A resin in Protein A column chromatography, wherein the second protein comprises two copies of the first Fc region and no copy of the second Fc region;
(d) preparing a sample comprising a mixture of protein molecules that includes a desired protein comprising the first Fc region and the second Fc region;
(e) passing the sample over a Protein A chromatography column comprising the resin; and
(f) collecting the desired protein from the column.

12. The method of claim 11, wherein the first Fc region is a human IgG1, IgG2, or IgG4 Fc region, and the second Fc region is a human IgG3 Fc region.

13. The method of claim 11, wherein the first Fc region has a His residue at EU numbering position 435, and the second Fc region has an Arg residue at EU numbering position 435.

14. The method of claim 11, wherein the first protein, the second protein, and the desired protein are antibodies.

15. The method of claim 14, wherein the desired protein is a bispecific antibody.

16. The method of claim 11,
wherein the desired protein is a bispecific antibody comprising a first arm comprising the first Fc region and a second arm comprising the second Fc region,
wherein the mixture of protein molecules of step (d) includes a first homodimer comprising two copies of the first arm and a second homodimer comprising two copies of the second arm,
wherein the desired protein has a higher dynamic binding capacity for the Protein A resin than does either the first or the second homodimer, and
wherein step (e) results in separation of the mixture of protein molecules according to their dynamic binding capacity on the Protein A chromatography column, so that the desired protein elutes from the column after the first and second homodimers.

17. The method of claim 16, wherein the first Fc region comprises a CH3 domain of a human IgG1, IgG2, or IgG4 Fc region, and the second Fc region comprises a CH3 domain of a human IgG3 Fc region.

18. The method of claim 16, wherein the first Fc region has a His residue at EU numbering position 435, and the second Fc region has an Arg residue at EU numbering position 435.

19. A method for separating a bispecific antibody from a mixture of antibodies, the method comprising:
(a) providing a mixture of antibodies comprising:
a first homodimer antibody comprising two copies of a first heavy chain comprising a first Fc region having a His residue at EU numbering position 435,
a second homodimer antibody comprising two copies of a second heavy chain comprising a second Fc region comprising an Arg residue at EU numbering position 435, and
a bispecific antibody comprising one copy of the first heavy chain and one copy of the second heavy chain, wherein the dynamic binding capacity of the bispecific antibody for Protein A resin in Protein A chromatography is higher than the dynamic binding capacity of either the first homodimer or the second homodimer for the Protein A resin in Protein A chromatography; and
(b) passing the mixture over a Protein A chromatography column comprising the Protein A resin, thereby separating the bispecific antibody from the first and second homodimer antibodies based on their differing dynamic binding capacity on the Protein A resin.

20. The method of claim 19, wherein the first Fc region comprises a CH3 domain of a human IgG1, IgG2, or IgG4 Fc region, and the second Fc region comprises a CH3 domain of a human IgG3 Fc region.

21. The method of claim 19, wherein each of the first homodimer antibody, the second homodimer antibody, and the bispecific antibody has two copies of a light chain that has the same amino acid sequence for all three antibodies.

* * * * *

SEQUENCE LISTING

```
<160> NUMBER OF SEQ ID NOS: 3

<210> SEQ ID NO 1
<211> LENGTH: 448
<212> TYPE: PRT
<213> ORGANISM: Artificial Sequence
<220> FEATURE:
<223> OTHER INFORMATION: An artificially synthesized peptide sequence

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser Ala Ser Thr Lys Gly
        115                 120                 125
```

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Glu Gly Asn Val Phe Ser Cys Ser Val Met His
            420                 425                 430

Glu Ala Leu His Asn Arg Tyr Thr Gln Lys Ser Leu Ser Leu Ser Pro
            435                 440                 445

<210> SEQ ID NO 2
<211> LENGTH: 444
<212> TYPE: PRT
<213> ORGANISM: Artificial Sequence
<220> FEATURE:
<223> OTHER INFORMATION: An artificially synthesized peptide sequence

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

```
Gly Asp Ile Asn Thr Arg Ser Gly Gly Ser Ile Tyr Asn Glu Glu Phe
     50                  55                  60

Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                 85                  90                  95

Ala Arg Arg Lys Ser Tyr Gly Tyr Tyr Leu Asp Glu Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
            435                 440

<210> SEQ ID NO 3
<211> LENGTH: 214
```

```
<212> TYPE: PRT
<213> ORGANISM: Artificial Sequence
<220> FEATURE:
<223> OTHER INFORMATION: An artificially synthesized peptide sequence

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```